(12) United States Patent
Araki et al.

(10) Patent No.: US 7,649,118 B2
(45) Date of Patent: *Jan. 19, 2010

(54) PROCESS FOR PREPARING FLUORINE-CONTAINING NORBORNENE DERIVATIVE

(75) Inventors: Takayuki Araki, Settsu (JP); Takuji Ishikawa, Settsu (JP); Takuji Kume, Settsu (JP); Akinori Yamamoto, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/649,265

(22) Filed: Jan. 4, 2007

(65) Prior Publication Data

US 2007/0129576 A1      Jun. 7, 2007

Related U.S. Application Data

(60) Division of application No. 10/753,529, filed on Jan. 9, 2004, now Pat. No. 7,186,773, which is a continuation-in-part of application No. PCT/JP02/07112, filed on Jul. 12, 2002.

(30) Foreign Application Priority Data

| Jul. 12, 2001 | (JP) | ............................. 2001-212689 |
| Sep. 14, 2001 | (JP) | ............................. 2001-280548 |
| Feb. 20, 2002 | (JP) | ............................... 2002-43920 |

(51) Int. Cl.
   *C07C 45/00* (2006.01)
(52) U.S. Cl. ..................... 568/354; 526/242; 526/281
(58) Field of Classification Search .................. 568/354; 526/242, 281
   See application file for complete search history.

(56) References Cited

U.S. PATENT DOCUMENTS

| 5,177,166 | A | * | 1/1993 | Kobo et al. ................. 526/249 |
| 6,468,712 | B1 | | 10/2002 | Fedynyshyn |
| 6,548,219 | B2 | | 4/2003 | Ito et al. |
| 6,858,760 | B2 | | 2/2005 | Komoriya et al. |
| 6,884,564 | B2 | | 4/2005 | Feiring et al. |
| 6,908,724 | B2 | * | 6/2005 | Araki et al. .............. 430/270.1 |
| 2001/0038969 | A1 | | 11/2001 | Hatakeyama |
| 2002/0055061 | A1 | | 5/2002 | Taylor et al. |
| 2002/0146638 | A1 | | 10/2002 | Ito et al. |
| 2003/0232276 | A1 | | 12/2003 | Poss et al. |
| 2004/0180287 | A1 | | 9/2004 | Feiring et al. |
| 2004/0225159 | A1 | | 11/2004 | Komoriya et al. |
| 2004/0265738 | A1 | | 12/2004 | Feiring et al. |

FOREIGN PATENT DOCUMENTS

| EP | 157262 A1 | 10/1985 |
| EP | 1 331 216 A1 | 7/2003 |
| EP | 1 398 339 A1 | 3/2004 |
| EP | 1 413 927 A1 | 4/2004 |
| WO | 2001-296662 A | 10/2001 |
| WO | WO 02/36533 A1 | 5/2002 |

OTHER PUBLICATIONS

Pirkle W.H. and Rinaldi P.L., "Use of Liquid-Crystal-Induced Circular Dichroism for Determination of Absolute Configuration of Alcohols and Oxaziridines", J. Org. Chem., 1990, vol. 45, pp. 1379 to 1382.

Krasovsky A.L. et al., "Diels-Alder reactions of N-trifluoroacetylvinylsulfones", Tetrahedron, Jan. 1, 2001, vol. 57, No. 1, pp. 201-209.

* cited by examiner

*Primary Examiner*—Daniel M Sullivan
*Assistant Examiner*—Chukwuma O Nwaonicha
(74) *Attorney, Agent, or Firm*—Sughrue Mion, PLLC

(57) ABSTRACT

There are provided a novel norbornene derivative which is a material for a chemically amplifying type photoresist for $F_2$ laser, possesses excellent transparency and improved dry etching resistivity and has a fluorine-containing ketone unit or fluorine-containing tertiary alcohol unit directly bonded to the norbornene backbone; a fluorine-containing polymer obtained by using the norbornene derivative as a copolymerizable monomer; and a chemically amplifying type photoresist composition comprising the fluorine-containing polymer, a photoacid generator and a solvent.

12 Claims, No Drawings

PROCESS FOR PREPARING FLUORINE-CONTAINING NORBORNENE DERIVATIVE

CROSS-REFERENCE TO RELATED APPLICATION

This application is a divisional of U.S. application Ser. No. 10/753,529 filed Jan. 9, 2004 now U.S Pat. No. 7,186,773, which is a continuation-in-part of PCT international application No. PCT/JP02/07112 filed on Jul. 12, 2002, the above-noted applications incorporated herein by reference in their entirety.

BACKGROUND OF THE INVENTION

The present invention relates to a novel norbornene derivative, a fluorine containing polymer prepared by copolymerizing the norbornene derivative, and a chemically amplifying type photoresist composition which is excellent in transparency and possesses improved dry etching resistance.

As a result of an increasing necessity for high integration of a large scale integrated circuit (LSI), microfabrication technology is required for photolithography. In order to satisfy such requirements, there have been tried to use, as exposure light sources, a deep ultraviolet, a KrF excimer laser (wavelength: 248 nm) and a ArF excimer laser (wavelength: 193 nm) which have a wavelength shorter than conventional g-rays (wavelength: 436 nm) and i-rays (wavelength: 365 nm). Those light sources are put into practical use.

Recently a process using a $F_2$ laser (wavelength: 157 nm) having a wavelength in a vacuum ultraviolet region has been studied in an ultra microfabrication technology and is considered promising as an exposure technology aiming at a technology node of 0.1 µm.

On the other hand, in the pattern formation, a chemically amplifying type resist which becomes advantageous in transparency, resolution, sensitivity and dry etching resistivity in cases of energy rays having various wavelengths has been studied. The chemically amplifying type resist means, for example, in case of a positive resist, an energy-sensitive composition comprising a resin soluble in an alkali developing solution and having an introduced substituent which has an effect of inhibiting dissolution of the resin but is deprotected due to action of an acid, and a compound which generates an acid by irradiation of energy rays such as light and electron beam (hereinafter referred to as a photoacid generator). When the composition is irradiated with light or electron beam, an acid is generated from the photoacid generator, and by heating (post-exposure bake, hereinafter referred to as "PEB") after the exposure of light, the substituent which has been giving a dissolution inhibiting effect on the resin is deprotected due to action of an acid. As a result, the exposed portion becomes soluble in alkali, and by treating the exposed portion with an alkali developing solution, a positive resist pattern can be obtained. In that case, the acid acts as a catalyst and exhibits its effect in a very small amount. Also action of the acid becomes active by the PEB and a chemical reaction is accelerated like a chain reaction, and thus sensitivity is enhanced.

Examples of conventional resins for chemically amplifying resist are phenol resins in which a part or the whole of hydroxyl is protected by a protective group such as acetal or ketal (KrF resist), methacrylic acid resins in which an acid-labile ester group is introduced to carboxyl (ArF resist) and the like.

However those conventional resist polymers have strong absorption in a wavelength range of vacuum ultraviolet region and have a significant problem that transparency against $F_2$ laser having a wavelength of 157 nm which is studied in a process for ultra fine pattern is low (a molecular absorption coefficient is high). Therefore in order to expose with $F_2$ laser, it is necessary to make a resist film thickness very thin and it is substantially difficult to use the polymers as a single layer $F_2$ resist.

R. R. Kunz, T. M. Bloomstein, et al. suggest in Journal of Photopolymer Science and Technology (Vol. 12, No. 4 (1999) 561-569) that fluorocarbons have good transparency at 157 nm as compared with various materials and have possibility of use as a $F_2$ resist.

However in that literature, there is only description that existing fluorocarbon polymers are high in transparency at 157 nm, but there is no description as to preferable structure of fluorine-containing polymers. Also with respect to a fluorine-containing polymer having functional group necessary, for example, for a positive type or negative type chemically amplifying resist, not only evaluation of transparency but also synthesis of the polymer is not made. Moreover the literature does not suggest a fluorine-containing base polymer material being preferable as a chemically amplifying resist and a preferable resist composition obtained therefrom at all, and there is found no possibility of forming a $F_2$ resist pattern by using a fluorine-containing polymer.

Thereafter A. E. Feiring, et al. of E. I. du Pont de Nemours and Company disclosed in PCT Patent Publication WO00/17712 (published Mar. 30, 2000) that a specific fluorine-containing polymer is useful for $F_2$ resist application.

That patent publication describes the use of a fluorine-containing polymer having a structural unit of fluoroolefin and a structural unit having a polycyclic structure.

Further an acid-labile (acid-decomposable) functional group necessary for a positive type resist is introduced to a fluorine-containing polymer by copolymerizing a conventional acrylic, methacrylic, norbornene or vinyl ester monomer with a monomer having an acid-labile (acid-decomposable) functional group. However there is no example of a polymer having a structural unit in which an acid-labile group which is changed to —C(Rf)(Rf')OH is directly bonded to a norbornene backbone.

Also a norbornene derivative is disclosed as one example of a polycyclic structure constituting a fluorine-containing polymer for a resist and a halogen-substituted norbornene is described, but there is no description as to an example of a fluorine-substituted norbornene, a norbornene simultaneously substituted by fluorine atom and an acid-reactive group in one molecule or a norbornene having a fluorine atom or acid-reactive group at specific position.

Further thereafter A. E. Feiring, et al. of E. I. du Pont de Nemours and Company disclosed in PCT Patent Publication WO00/67072 (published Nov. 9, 2000) that a fluorine-containing polymer having —C(Rf)(Rf')OH or —C(Rf)(Rf')O—Rb is useful for $F_2$ resist application.

In that patent publication, a structural unit of norbornene in which —C(Rf)(Rf')OH or —C(Rf)(Rf')O—Rb is bonded through a part of —CH$_2$OCH$_2$—. However there is no description as to an example of —C(Rf)(Rf')OH being directly bonded to a norbornene backbone.

Further there is disclosed norbornene derivatives having —C(Rf)(Rf')OH or —C(Rf)(Rf')O—Rb as an example of a fluorine-containing polymer to be used for a resist. Among them, there is disclosed a halogen-substituted norbornene. However there is concretely no description as to an example of a fluorine-substituted norbornene, a norbornene simultaneously subjected to substitution of fluorine atom and the above-mentioned acid-reactive group in one molecule or a norbornene subjected to substitution at a specific position.

Further Katsuyama, et al. of Matsushita Electric Industrial Co., Ltd. proposed a method of forming a pattern with exposure light having a wavelength of from 1 to 180 nm using a resist material containing halogen atom (JP2000-321774A published Nov. 24, 2000). However there is disclosed only a methacrylic resin having a structural unit of methacrylic ester having —$CH_2CF_3$ group and —$CH(CF_3)_2$ group in its side chain as a base resin having halogen atom for a resist, and no resin containing fluorine atom in its trunk chain is disclosed. Also there is concretely disclosed no polymer which has a structural unit of fluorine-containing monomer having functional group and fluorine atom simultaneously and can act as a chemically amplifying resist (positive type or negative type). Further there is no description as to a polymer having a cyclic structure in its trunk chain.

Also there is generally known that dry etching resistivity of a polymer is enhanced by introducing a norbornene backbone to the polymer. However transparency, particularly transparency in a vacuum ultraviolet region of conventional norbornene derivatives cannot be said to be sufficient. In the present invention, it was found that transparency, particularly transparency in a vacuum ultraviolet region is enhanced by introducing fluorine atom or a fluorine-containing group to a specific position of a norbornene derivative.

Also in conventional resist polymers though an acid-reactive group necessary for a resist polymer is introduced by polymerizing an ethylenic monomer (acrylic monomer, etc.), transparency (particularly transparency in a vacuum ultraviolet region) and dry etching resistivity are lowered by the introduction. In the present invention it was found that when an acid-reactive group necessary for a resist together with fluorine atom or fluoroalkyl group are introduced to one molecule of a norbornene derivative simultaneously, both of good transparency (particularly transparency in a vacuum ultraviolet region) and dry etching resistivity can be imparted to a fluorine-containing polymer obtained by polymerizing the norbornene derivative.

The first object of the present invention is to provide a novel fluorine-containing norbornene derivative and a process for preparation thereof.

The second object of the present invention is to provide a novel fluorine-containing polymer obtained by copolymerizing the novel fluorine-containing norbornene derivative.

The third object of the present invention is to provide a chemically amplifying photoresist composition which comprises a fluorine-containing polymer having a fluorine-containing norbornene unit and acid-labile group, and a photoacid generator, and can be used for a patterning process using $F_2$ laser as light source.

SUMMARY OF THE INVENTION

The present inventors have made intensive studies to achieve the above-mentioned objects and as a result have found a novel fluorine-containing norbornene derivative and a fluorine-containing polymer which is obtained by copolymerizing the derivative and is useful as a polymer for a resist.

Namely, the present invention relates to a process for preparing a fluorine-containing norbornene derivative having a fluorine-containing ketone structure which is represented by the formula (2):

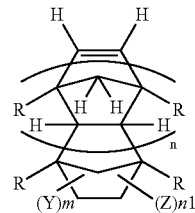

wherein Z is the same or different and each is:

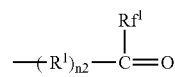

in which $Rf^1$ is a fluorine-containing alkyl group having 1 to 10 carbon atoms or a fluorine-containing alkyl group which has 1 to 10 carbon atoms and ether bond, $R^1$ is a divalent organic group, n2 is 0 or 1; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1 =6. The process is characterized by reacting a norbornene derivative represented by the formula (1):

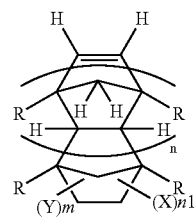

wherein X is the same or different and each is:

—$(R^1)_{n2}$—$X^1$ in which $X^1$ is —$COOR^2$ or:

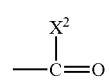

in which $R^2$ is an alkyl group having 1 to 5 carbon atoms, $X^2$ is halogen atom; Y, R, $R^1$, m, n, n1 and n2 are as defined above, with a fluoroalkylation agent introducing $Rf^1$, wherein $Rf^1$ is as defined above, to X in the formula (1).

Examples of preferred fluoroalkylation agent are fluorosilane compounds represented by:

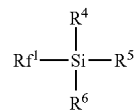

wherein $Rf^1$ is a fluorine-containing alkyl group having 1 to 10 carbon atoms or a fluorine-containing alkyl group which has 1 to 10 carbon atoms and ether bond; $R^4$, $R^5$ and $R^6$ are the same or different and each is a hydrocarbon group having 1 to 10 carbon atoms.

Also the present invention relates to a process for preparing a fluorine-containing norbornene derivative having a fluorine-containing tertiary alcohol structure which is represented by the formula (4):

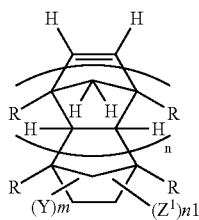

wherein $Z^1$ is the same or different and each is:

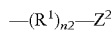

in which $Z^2$ is:

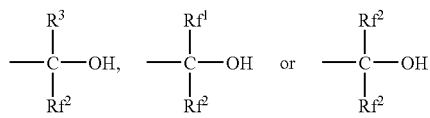

wherein $Rf^1$ is a fluorine-containing alkyl group having 1 to 10 carbon atoms or a fluorine-containing alkyl group which has 1 to 10 carbon atoms and ether bond, $Rf^2$ is a fluorine-containing alkyl group having 1 to 10 carbon atoms or a fluorine-containing alkyl group which has 1 to 10 carbon atoms and ether bond, $R^3$ is H or a hydrocarbon group having 1 to 10 carbon atoms, $R^1$ is a divalent organic group; n2 is 0 or 1; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6. The process is characterized by reacting a norbornene derivative represented by the formula (3):

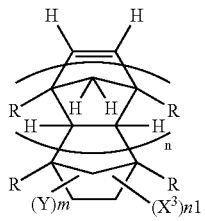

wherein $X^3$ is the same or different and each is:

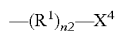

in which $X^4$ is —$COOR^2$,

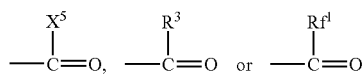

wherein $R^2$ is an alkyl group having 1 to 5 carbon atoms, $X^5$ is halogen atom; $R^3$, $Rf^1$, $R^1$, Y, R, m, n, n1 and n2 are as defined above, with a fluoroalkylation agent introducing $Rf^2$, wherein $Rf^2$ is as defined above, to $X^4$.

Examples of preferred fluoroalkylation agent are fluorosilane compounds represented by:

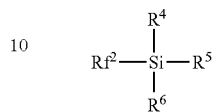

wherein $Rf^2$ is a fluorine-containing alkyl group having 1 to 10 carbon atoms or a fluorine-containing alkyl group which has 1 to 10 carbon atoms and ether bond; $R^4$, $R^5$ and $R^6$ are the same or different and each is a hydrocarbon group having 1 to 10 carbon atoms.

The present invention also relates to novel norbornene derivatives represented by the following formulae.

A norbornene derivative having a fluorine-containing ketone structure represented by the formula (5):

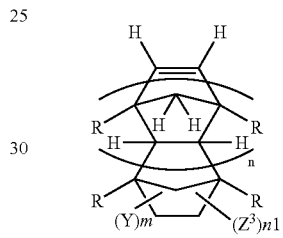

wherein $Z^3$ is the same or different and each is:

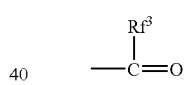

in which $Rf^3$ is a fluorine-containing alkyl group having. 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6.

A norbornene derivative having a fluorine-containing ketone structure represented by the formula (6):

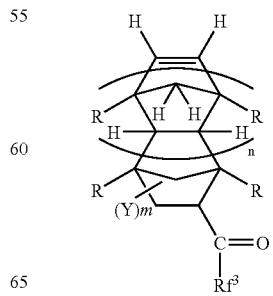

in which $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is 5, or the formula (7):

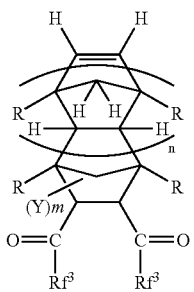

in which $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is 4.

In the derivatives of the formulae (5), (6) and (7), preferred are compounds in which $Rf^3$ is $CF_3$.

A norbornene derivative having a fluorine-containing alcohol structure represented by the formula (8):

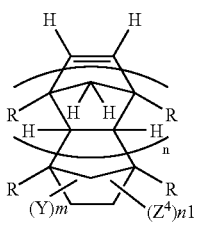

wherein $Z^4$ is the same or different and each is:

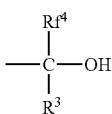

in which $Rf^4$ is the same or different and each is a fluorine-containing alkyl group having 1 to 10 carbon atoms or a fluorine-containing alkyl group which has 1 to 10 carbon atoms and ether bond; $R^3$ is H or a hydrocarbon group having 1 to 10 carbon atoms; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6.

A norbornene derivative having a fluorine-containing alcohol structure represented by the formula (9):

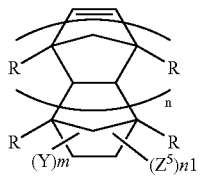

wherein $Z^5$ is the same or different and each is:

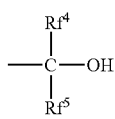

in which $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n6.

A norbornene derivative having a fluorine-containing alcohol structure represented by the formula (10):

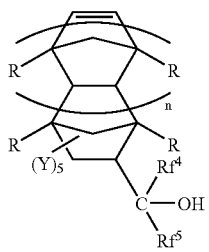

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5.

In the derivatives represented by the formulae (9) and (10), at least one of the substituents Y is preferably F or a fluorine-containing alkyl group which has 1 to 10 carbon atoms and may have ether bond.

A norbornene derivative having a fluorine-containing alcohol structure represented by the formula (11):

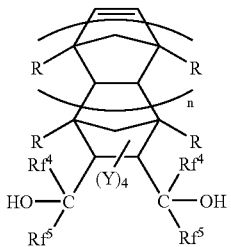

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5.

A norbornene derivative having a fluorine-containing alcohol structure represented by the formula (12):

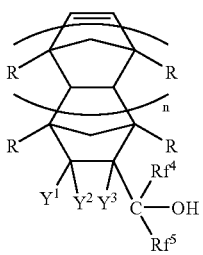

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; at least one of $Y^1$, $Y^2$ and $Y^3$ is F or a fluorine-containing alkyl group which has 1 to 10 carbon atoms and may have ether bond.

In the derivative represented by the formula (12), preferred is a compound in which $Y^1$ and $Y^2$ are H and $Y^3$ is F or $CF_3$ or a compound in which $Y^1$ and $Y^2$ are F and $Y^3$ is F or $CF_3$.

Also in the derivatives represented by the formulae (8) to (12), preferred is a compound in which $Rf^4$ and $Rf^5$ are $CF_3$.

The present invention also relates to novel fluorine-containing polymers obtained by copolymerizing the novel fluorine-containing norbornene derivatives represented by the formulae (5) to (12).

Concretely the present invention relates to a fluorine-containing polymer having a number average molecular weight of from 500 to 1,000,000 which has a ring structure in the polymer trunk chain and is represented by the formula (13):

-(M1)-(M2)-(N)- wherein M1 is a structural unit derived from at least one selected from the novel fluorine-containing norbornene derivatives represented by the formulae (5) to (12) and the norbornene derivatives which are represented by the formulae (5) to (12) and have a protective acid-reactive functional group —$OQ^1$ protecting hydroxyl thereof; M2 is a structural unit obtained from a fluorine-containing ethylenic monomer having 2 or 3 carbon atoms and at least one fluorine atom; N is a structural unit derived from monomer copolymerizable with the structural units M1 and M2, and the structural units M1, M2 and N are contained in amounts of from 1 to 99% by mole, from 1 to 99% by mole and from 0 to 98% by mole, respectively. It is particularly preferable that when M1+M2 is 100% by mole, a percent by mole ratio of M1/M2 is 1/99 to 70/30, further 30/70 to 70/30.

In the fluorine-containing polymer, it is preferable that the structural unit M2 is a structural unit obtained from at least one monomer selected from the group consisting of tetrafluoroethylene, chlorotrifluoroethylene, vinylidene fluoride and vinyl fluoride, particularly a structural unit obtained from tetrafluoroethylene or chlorotrifluoroethylene.

The present invention also relates to a chemically amplifying type photoresist composition which comprises:

(A) a fluorine-containing polymer having OH group and/or a group comprising a protective acid-reactive functional group —$OQ^1$ protecting hydroxyl thereof, (B) a photoacid generator, and (C) a solvent, in which the fluorine-containing polymer (A) having an acid-reactive group is a fluorine-containing polymer represented by the formula (14):

-(M1a)-(M2)-(N)- (14)

wherein M1a is a structural unit derived from the norbornene derivatives of the formulae (8) to (12) having a fluorine-containing alcohol structure and/or the norbornene derivatives having a fluorine-containing alcohol structure which are represented by the formulae (8) to (12) and have a protective acid-reactive functional group —$OQ^1$ protecting hydroxyl thereof; M2 is a structural unit obtained from a fluorine-containing ethylenic monomer having 2 or 3 carbon atoms and at least one fluorine atom; N is a structural unit derived from monomer copolymerizable with the structural units M1a and M2.

In the above-mentioned photoresist composition, it is preferable that the fluorine-containing polymer (A) is a fluorine-containing polymer having a ring structure in the polymer trunk chain which has a number average molecular weight of from 500 to 1,000,000 and is represented by the formula (14)-2:

-(M1a-1)-(M1a-2)-(M2)-(N)- (14)-2 wherein M1a-1 is a structural unit derived from at least one selected from the norbornene derivatives having a fluorine-containing alcohol structure of the formulae (8) to (12); M1a-2 is a structural unit derived from at least one selected from the above-mentioned norbornene derivatives having a protective acid-reactive functional group; M2 and N are as defined in the formula (14); provided that (M1a-1)+(M1a-2)+M2 is 100% by mole, a percent by mole ratio of {(M1a-1)+(M1a-2)}/M2 is 30/70 to 70/30, and the polymer contains M1a-1, M1a-2, M2 and N in amounts of from 1 to 98% by mole, from 1 to 98% by mole, from 1 to 98% by mole and from 0 to 97% by mole, respectively. Further preferred is the fluorine-containing polymer in which provided that (M1a-1)+(M1a-2) is 100% by mole, a percent by mole ratio of (M1a-1)/(M1a-2) is 90/10 to 50/50.

The fluorine-containing polymer (A) may be a fluorine-containing polymer which is represented by the formula (14)-3:

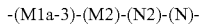
-(M1a-3)-(M2)-(N2)-(N)-         (14)-3 wherein the structural unit M2 is as defined in the formula (14), p0 the structural unit M1a-3 is a structural unit derived from at least one selected from the norbornene derivatives of the formula (8) to (12) or the norbornene derivatives of the formula (8) to (12) having a protective acid-reactive functional group which protects hydroxyl thereof, the structural unit N2 is a structural unit derived from a cyclic aliphatic unsaturated hydrocarbon which is copolymerizable with monomers constituting the structural units M1a-3, M2 and N and has COOH group or an acid-labile functional group being convertible to carboxyl by an acid, the structural unit N is a structural unit derived from monomer copolymerizable with monomers constituting the structural units M1a-3, M2 and N2, provided that (M1a-3)+M2 +N2 is 100% by mole, a percent by mole ratio of {(M1a-3)+(N2)}/M2 is 70/30 to 30/70, and the structural units M1a-3, M2, N2 and N are contained in amounts of from 1 to 98% by mole, from 1 to 98% by mole, from 1 to 98% by mole and from 0 to 97% by mole, respectively.

In the fluorine-containing polymer of the formula (14)-3, the structural unit N2 may be a structural unit derived from a norbornene derivative having COOH group or an acid-labile functional group which is convertible to carboxyl by an acid. It is preferable that the norbornene derivative having COOH group or an acid-labile functional group which is convertible to carboxyl by an acid is one represented by the formula:

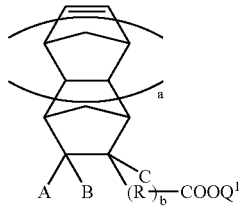

wherein A, B and C are H, F, an alkyl group having 1 to 10 carbon atoms or a fluorine-containing alkyl group having 1 to 10 carbon atoms; R is a divalent hydrocarbon group having 1 to 20 carbon atoms, a fluorine-containing alkylene group having 1 to 20 carbon atoms or a fluorine-containing alkylene group having 2 to 100 carbon atoms and ether bond; a is 0 or an integer of from 1 to 3; b is 0 or 1; $COOQ^1$ is COOH group or an acid-labile functional group which is convertible to carboxyl by an acid; when b is 0 or R does not have fluorine atom, any one of A, B and C is fluorine atom or a fluorine-containing alkyl group.

Further the fluorine-containing polymer (A) may be a fluorine-containing polymer which is represented by the formula (14)-4:

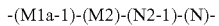
-(M1a-1)-(M2)-(N2-1)-(N)-         (14)-4 wherein the structural units M1a-1 and M2 are as defined in the formula (14)-2, the structural unit N2-1 is a structural unit derived from a norbornene derivative represented by the formula:

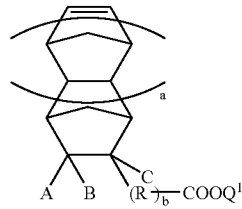

in which $COOQ^1$ is an acid-labile functional group which is convertible to carboxyl by an acid, A, B, C, R, a and b are as defined above, the structural unit N is a structural unit derived from monomer copolymerizable with monomers constituting the structural units M1a-1, M2 and N2-1, provided that (M1a-1)+(M2)+(N2-1) is 100% by mole, a percent by mole ratio of {(M1a-1)+(N2-1)}/(M2) is 70/30 to 30/70, and provided that (M1a-1)+(N2-1) is 100% by mole, a percent by mole ratio of (M1a-1)/(N2-1) is 95/5 to 50/50, and the structural units M1a-1, M2, N2-1 and N are contained in amounts of from 1 to 98% by mole, from 1 to 98% by mole, from 1 to 98% by mole and from 0 to 97% by mole, respectively.

In the fluorine-containing polymer of the formula (14)-4, it is preferable that the structural unit M2 is a structural unit obtained from at least one monomer selected from the group consisting of tetrafluoroethylene, chlorotrifluoroethylene, vinylidene fluoride and vinyl fluoride, particularly a structural unit obtained from tetrafluoroethylene or chlorotrifluoroethylene.

Further the present invention relates to a chemically amplifying type photoresist composition comprising:
(A) a fluorine-containing polymer having OH group or a group which can be dissociated by an acid and converted to OH group,
(B) a photoacid generator, and
(C) a solvent, in which the fluorine-containing polymer (A) is a fluorine-containing polymer having a number average molecular weight of from 500 to 1,000,000 and represented by the formula (14)-1:

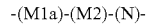
-(M1a)-(M2)-(N)-         (14)-1 wherein the structural unit M1a is a structural unit derived from at least one selected from norbornene derivatives having a fluorine-containing alcohol structure and represented by the formula (15):

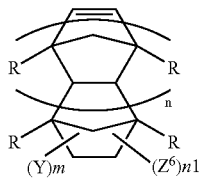

in which $Z^6$ is the same or different and each is:

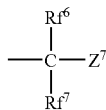

wherein $Rf^6$ and $Rf^7$ are the same or different and each is a fluorine-containing alkyl group having 1 to 10 carbon atoms or a fluorine-containing alkyl group having 1 to 10 carbon atoms and ether bond; $Z^7$ is OH group or a group dissociated due to action of an acid and converted to OH group; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6, the structural unit M2 is a structural unit derived from an ethylenic monomer having 2 or 3 carbon atoms and at least one fluorine atom, the structural unit N is a structural unit derived from monomer copolymerizable with the structural units M1a and M2, and provided that M1a+M2 is 100% by mole, a percent by mole ratio of M1a/M2 is 1/99 to 70/30, and the structural unit M1a, the structural unit M2 and the structural unit N are contained in amounts of from 1 to 99% by mole, from 1 to 99% by mole and from 0 to 98% by mole, respectively.

In the structural unit M1a of the fluorine-containing polymer (A), it is preferable that at least one of the substituents Y in the formula (15) is F or a fluorine-containing alkyl group which has 1 to 10 carbon atoms and may have ether bond.

It is also preferable that in the fluorine-containing polymer (A), the structural unit M1a is a structural unit derived from fluorine-containing norbornene derivatives represented by the formula (16):

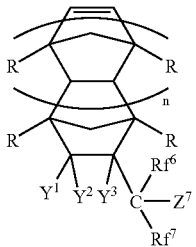

wherein $Rf^6$ and $Rf^7$ are the same or different and each is a fluorine-containing alkyl group having 1 to 10 carbon atoms or a fluorine-containing alkyl group having 1 to 10 carbon atoms and ether bond; $Z^7$ is OH group or a group dissociated due to action of an acid and converted to OH group; $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5.

It is also preferable that in the structural unit M1a of the fluorine-containing polymer (A), $Y^1$ and $Y^2$ are H and $Y^3$ is F or $CF_3$ in the formula (16).

It is also preferable that in the structural unit M1a of the fluorine-containing polymer (A), $Y^1$ and $Y^2$ are F and $Y^3$ is F or $CF_3$ in the formula (16).

It is also preferable that in the structural unit M1a of the fluorine-containing polymer (A), $Rf^6$ and $Rf^7$ in the formula (16) are $CF_3$.

It is also preferable that in the structural unit M1a of the fluorine-containing polymer (A), the group $Z^7$ which is dissociated due to action of an acid and converted to OH group is a group represented by:

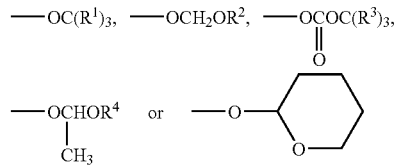

wherein $R^1$, $R^2$, $R^3$ and $R^4$ are the same or different and each is an alkyl group having 1 to 5 carbon atoms.

It is preferable that the structural unit M2 of the fluorine-containing polymer (A) is a structural unit obtained from at least one monomer selected from the group consisting of tetrafluoroethylene and chlorotrifluoroethylene.

DETAILED DESCRIPTION

First, the preparation process of the present invention is explained below.

It is demanded that fluorine-containing norbornenes, particularly norbornene derivatives having a group represented by:

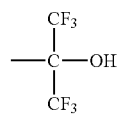

are used on a part of structural units of a resist polymer (particularly resist for $F_2$ laser) since such norbornenes have OH group having high acidity and therefore are soluble in an aqueous alkaline solution (resist developing solution), have functional group having high transparency in ultraviolet region (particularly in a short wavelength region) and have norbornene backbone having excellent dry etching resistivity.

With respect to known methods of preparing norbornene compounds having a group represented by:

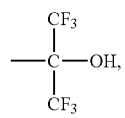

there is (i) a method of synthesizing:

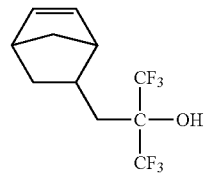

by Diels-Alder reaction of

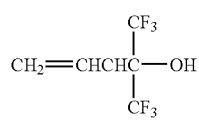

and cyclopentadiene. However it can hardly be said that this method is preferred from industrial point of view because the Diels-Alder reaction in combination of the allyl compound and cyclopentadiene is low in reactivity and the reaction need be carried out at high temperatures of not less than 150° C. and further because of high temperature reaction, there are produced a large amount of dimers and trimers of cyclopentadiene and by-products comprising intended norbornene compound having 1 to 3 molecules of cyclopentadiene added thereto by ring formation, which results in lowering of yield.

Also there is reported (ii) a method of synthesizing:

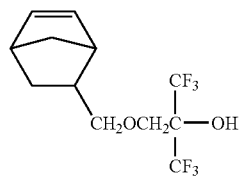

by a reaction of:

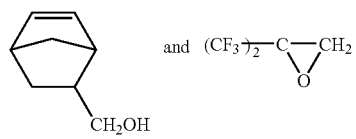

(WO00/66575 Publication).

However this method is not preferred because multiple steps are needed for synthesizing:

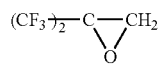

and productivity is not good and also because the process for synthesizing:

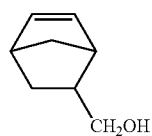

is not good in productivity and high in cost.

The present invention provides the method of introducing a group represented by:

to the norbornene backbone at high yield at low cost.

An object of the preparation process of the present invention is to react a norbornene derivative represented by the formula (1):

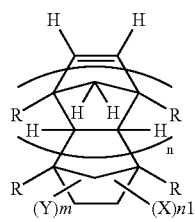

wherein X is the same or different and each is:

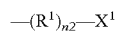

wherein $X^1$ is —COOR$^2$ or:

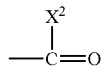

in which $R^2$ is an alkyl group having 1 to 5 carbon atoms; $X^2$ is halogen atom; $R^1$ is a divalent organic group; n2 is 0 or 1; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6, with a fluoroalkylation agent introducing Rf$^1$, wherein Rf$^1$ is a fluorine-containing alkyl group having 1 to 10 carbon atoms or a fluorine-containing alkyl group having 1 to 10 carbon atoms and ether bond, to X in the formula (1), thereby synthesizing a norbornene derivative having carboxylic acid ester or acid halide which is represented by the formula (2):

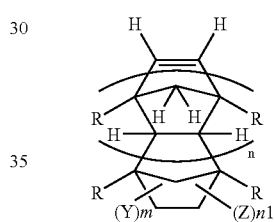

wherein Z are the same or different and each is represented by:

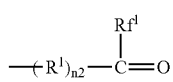

in which Rf$^1$, R$^1$ and n2 are as defined above; Y, R, n, m and n1 are as defined above.

Another object is to convert to a norbornene derivative having Rf$^1$Rf$^2$C—OH group by reacting a norbornene derivative having a ketone structure and represented by the formula (3):

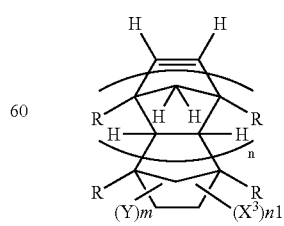

with a fluorine-containing alkylation agent.

The present invention also encompasses the process for preparing a novel norbornene having a ketone structure represented by:

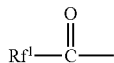

and the process for preparing a novel norbornene having:

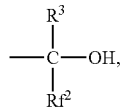

wherein $R^3$ is H or a hydrocarbon group; $Rf^2$ is as defined above.

Namely, the present invention provides the process for preparing the above-mentioned various fluorine-containing norbornenes at high yield by reacting a norbornene having C=O group which can be easily synthesized at high yield by the Diels-Alder reaction, with a fluoroalkylation agent.

The first of the preparation processes of the present invention relates to the process for preparing the novel fluorine-containing norbornene derivative having a fluorine-containing ketone structure which is represented by the formula (2):

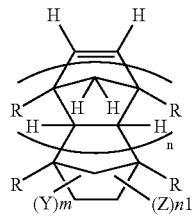

by reacting the norbornene derivative having carboxylic acid ester or acid halide which is represented by the formula (1):

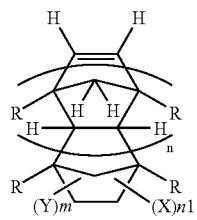

with a fluoroalkylation agent.

Namely, the group represented by:

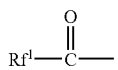

can be introduced by reacting a fluoroalkylation agent ($Rf^1$) in an amount equivalent to the weight of carboxylic acid ester or acid halide of the formula (1) and thereby the novel norbornene compound can be prepared.

Examples of the norbornene derivative (1) as a starting material are preferably:

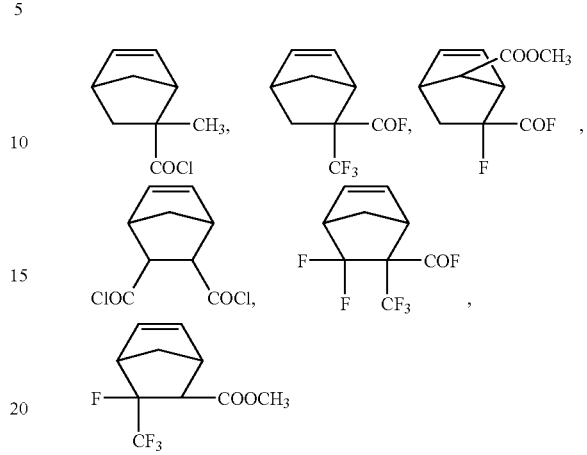

and the like.

According to the preparation process of the present invention, the ketone structure:

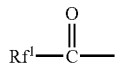

corresponding to the fluoroalkylation agent ($Rf^1$) to be reacted with the norbornene derivative mentioned above as a starting material can be introduced. Concretely there can be obtained the following norbornene derivatives.

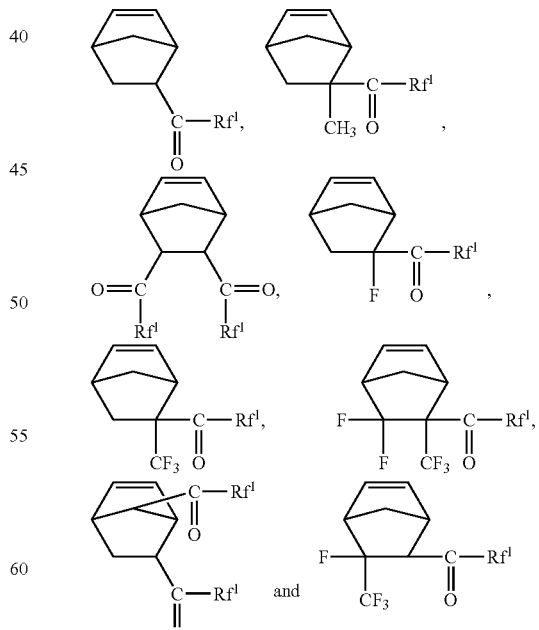

X is selected from alkyl esters such as —COOCH$_3$, —COOC$_2$H$_5$ and —COOC(CH$_3$)$_3$ and acid halides, for example, —COF, —COCl and —COBr.

In the norbornene backbone, one X may be present or a plurality of the same or different X bonded to each other may be present.

Y may be replaced with H, F, Cl, an alkyl group or a fluorine-containing alkyl group, and it is particularly preferable that Y is replaced with F or a fluorine-containing alkyl group because transparency can be enhanced in case of use for a resist.

Examples of preferred norbornene derivative to be used as a starting material (formula (1)) are as follows.

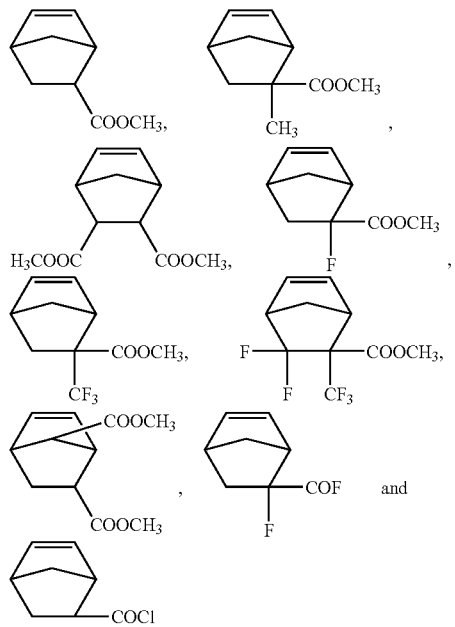

The second preparation process of the present invention relates to the process for preparing the fluorine-containing norbornene 20 derivative having a fluorine-containing tertiary alcohol structure represented by the formula (4):

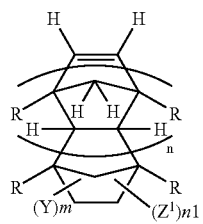

by reacting the norbornene derivative having a ketone structure represented by the formula (3):

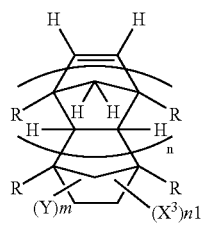

with a fluoroalkylation agent ($Rf^2$).

In this preparation process, $X^3$ in the starting material of the formula (3) is a moiety of ketone structure and may be a fluorine-containing ketone:

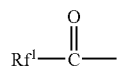

obtained by the above-mentioned first preparation process, or may be a fluorine-containing ketone:

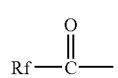

obtained by other preparation process. Also $X^3$ may be a hydrocarbon type ketone structure:

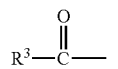

having no fluorine or may be aldehyde:

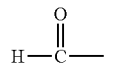

Y is selected from H or the above-mentioned substituent Y and there are preferably the same examples as those of the above-mentioned Y.

Examples of preferred derivative having a fluorine-containing ketone structure:

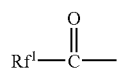

which is used as the starting material (formula (3)) are the same as those of the norbornene derivative having a fluorine-containing ketone structure obtained by the above-mentioned preparation process.

According to the preparation process of the present invention, a moiety of fluorine-containing tertiary alcohol:

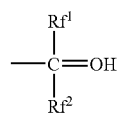

corresponding to the reacted fluoroalkylation agent ($Rf^2$) can be introduced to the norbornene derivative of a starting material.

Concretely there can be obtained the following norbornene derivatives:

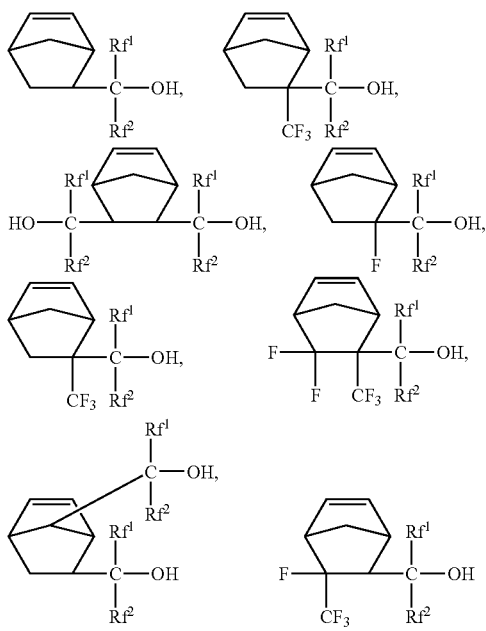

and the like.

Further in order to obtain a norbornene derivative having a moiety of fluorine-containing tertiary alcohol structure:

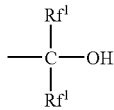

it is possible to react a fluoroalkylation agent with the norbornene having carboxylic acid ester or acid halide represented by the formula (1) in an amount of two equivalents or more to the respective functional group X.

When a norbornene derivative having a hydrocarbon ketone structure:

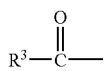

having no fluorine or aldehyde:

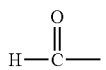

is used as a starting material, preferred examples thereof are as follows.

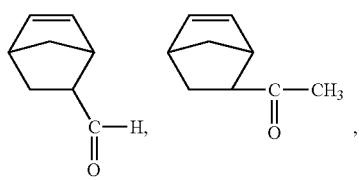

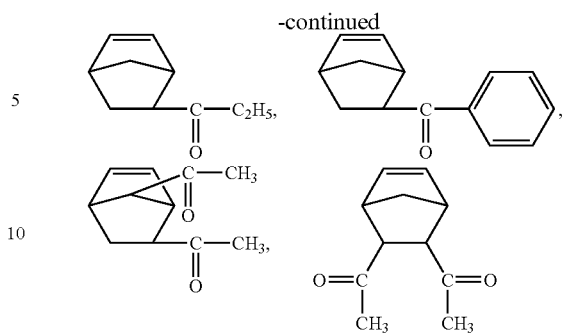

and the like. And novel fluorine-containing norbornenes having tertiary alcohol moiety such as:

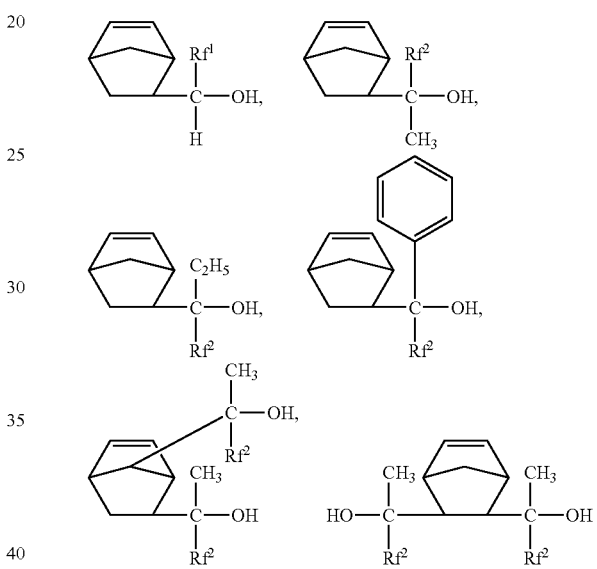

and the like can be obtained.

The fluoroalkylation agent which is reacted with the norbornene derivative as a starting material in the two preparation processes of the present invention is generally selected from organometallic compounds having a fluoroalkyl group.

For example, there are $Rf^1M^1X$ (or $Rf^2M^1X$) or $Rf^1M^2$ (or $Rf^2M^2$), in which $M^1$ is alkali earth metal, $M^2$ is alkali metal, X is halogen atom, $Rf^1$ is a fluoroalkyl group, and concretely there are $Rf^1MgI$, $Rf^1MgBr$, $Rf^1ZnI$, $Rf^1ZnBr$, $Rf^2MgI$, $Rf^2MgBr$, $Rf^2ZnI$, $Rf^2ZnBr$, $Rf^1Li$, $Rf^2Li$ and the like. More concretely there are $C_2F_5MgBr$, $C_2F_5MgI$, $C_4F_9MgI$, $C_4F_9MgBr$, $C_2F_5Li$, $C_4F_9Li$, $CF_3ZnI$, $C_2F_5ZnI$, $C_4F_9ZnI$ and the like.

In the present invention, when reacting the fluoroalkylation agent with the norbornene derivative having carboxylic acid ester or acid halide of the formula (1) or the norbornene derivative having a ketone structure of the formula (3), generally it is preferable to use an aprotic polar solvent or a cyclic or acyclic ether solvent as a reaction solvent. Examples thereof are tetrahydrofuran, dioxane, monoglyme, diglyme, triglyme, tetraglyme, methyl-t-butyl ether, acetonitrile, benzonitrile, sulfolane, N,N-dimethylformamide, N,N-dimethylacetamide and the like.

A reaction temperature and reaction time vary depending on kinds of a norbornene compound as a starting material and a fluoroalkylation agent and are selected optionally. It is preferable that the reaction is carried out at a temperature of from −80° C. to +120° C., particularly at a temperature of not more than +10° C., especially at a low temperature of not more than −10° C.

The reaction time is preferably from 10 minutes to 100 hours, more preferably from 30 minutes to 10 hours.

The intended norbornene derivative having a fluorine-containing ketone structure and norbornene derivative having a fluorine-containing tertiary alcohol structure can be obtained by acting a protonic acid after completion of the above-mentioned reaction. Preferred as a protonic acid are hydrochloric acid, sulfuric acid, nitric acid and the like, and it is preferable that the protonic acid is acted in the form of aqueous solution. A concentration thereof is not limited.

When reacting with a protonic acid, an alcohol such as methanol, ethanol, isopropanol or the like may be used as a solvent.

Examples of secondarily preferred fluoroalkylation agent are trimethyl silyl compounds represented by:

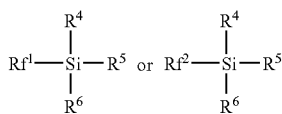

and a trimethyl silyl compound corresponding to the intended fluoroalkyl group can be used.

$Rf^1$ is selected from fluorine-containing alkyl groups having 1 to 10 carbon atoms or fluorine-containing alkyl groups having 1 to 10 carbon atoms and ether bond.

The fluoroalkyl group is one obtained by replacing a part of the whole of hydrogen atoms of an alkyl group or alkyl group having ether bond with fluorine atoms and partly may have other halogen atoms such as Cl or Br. Among them, a perfluoroalkyl group or a perfluoroalkyl group having ether bond is preferred from the point that transparency can be imparted more to norbornene or a polymer prepared using the norbornene and that acidity of OH group in the structure:

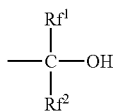

can be enhanced.

Examples thereof are:

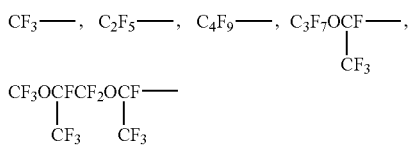

and the like, and among them, $CF_3$ is preferred from the viewpoint of good reactivity.

$R^4$, $R^5$ and $R^6$ are generally selected from hydrocarbons having 1 to 10 carbon atoms, and usually $CH_3$ is preferred from the viewpoint of good reactivity.

Namely, examples of preferred trimethyl silyl compound to be used as a fluoroalkylation agent are:

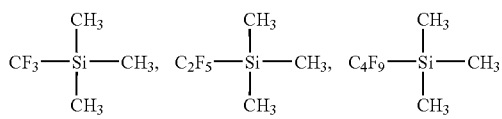

and the like, and particularly preferred is $CF_3Si$—$(CH_3)_3$.

In the present invention, in the reaction of the norbornene compound of the formula (1) or (3) with the above-mentioned trimethyl silyl compound, in addition to the trimethyl silyl compound, it is preferable to add a compound which generates, in a system, $F^-$ in an amount of from a catalytic amount (0.01 equivalent) to twice amount to the starting norbornene and a functional group:

contained therein, for advancing the reaction rapidly.

Therefore such a compound is not limited as far as it generates $F^-$. Generally there are preferably used fluorides of alkali metal such as KF and CsF, quaternary ammonium salts (those having $F^-$ as an anion) such as tributylammonium fluoride, a combination of crown ether and metal fluoride and the like.

It is preferable that $F^-$ ion is added in an equivalent amount or more or in an excessive amount to the functional group:

except the cases of using a starting norbornene having a group:

or using a quaternary ammonium salt (F⊖ salt).

In the preparation process of the present invention using a trimethyl silyl compound (in addition, F⊖ ion), it is generally preferable to use a reaction solvent such as an aprotic polar solvent, a cyclic or acyclic ether solvent, a hydrocarbon solvent or a fluorine-containing solvent.

Examples thereof are tetrahydrofuran, dioxane, monoglyme, diglyme, triglyme, tetraglyme, methyl-t-butyl ether, hexane, HCFC141b, HFC-225, N,N-dimethylformamide and the like.

A reaction temperature and a reaction time vary depending on kinds of a norbornene compound and a fluoroalkylation agent and are optionally selected. It is preferable that the reaction is carried out at a temperature of from −80° C. to +120° C., particularly at a low temperature of from −10° C. to room temperature (especially not more than +10° C.).

The reaction time is preferably from 10 minutes to 100 hours, more preferably from 30 minutes to 10 hours.

The intended norbornene derivative having a fluorine-containing ketone structure and norbornene derivative having a fluorine-containing tertiary alcohol structure can be obtained by acting a protonic acid after completion of the above-mentioned reaction.

Preferred as a protonic acid are hydrochloric acid, sulfuric acid, nitric acid and the like, and it is generally preferable that the protonic acid is acted in the form of aqueous solution. A concentration thereof is not limited particularly.

When reacting with a protonic acid, an alcohol such as methanol, ethanol, isopropanol or the like may be used as a solvent.

Among the fluorine-containing norbornene derivatives which are used in or obtained by the above-mentioned preparation processes, the compounds represented by the formulae (5) to (12) are novel compounds.

The norbornene derivatives of the respective formulae are explained below.

The first of the norbornene derivatives of the present invention is one in which a moiety of fluorine-containing ketone structure:

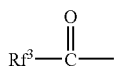

is bonded directly to the norbornene backbone, and is a novel compound which is not disclosed in patent publications and technical literatures.

Such a novel norbornene derivative is one having a fluorine-containing ketone structure represented by the formula (5):

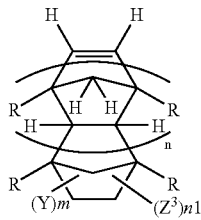

wherein $Z^3$ is the same or different and each is:

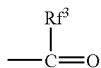

in which $Rf^3$ is a fluorine-containing alkyl group having 1 to 10 carbon atoms or a fluorine-containing alkyl group having 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6.

The norbornene derivative may have one or a plurality of moieties of fluorine-containing ketone represented by:

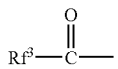

Particularly preferred are the norbornene derivatives having a fluorine-containing ketone structure represented by the formula (6):

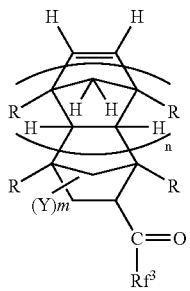

in which $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is 5, or the formula (7):

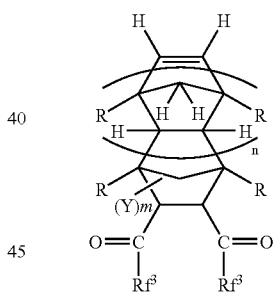

in which $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is 4.

From the viewpoint of enhancement of transparency in case of the use for a resist, Y is preferably H, F, Cl, an alkyl group having 1 to 10 carbon atoms, a fluorine-containing alkyl group having 1 to 10 carbon atoms or a fluorine-containing alkyl group having 1 to 10 carbon atoms and ether bond, and particularly preferred are F, a fluorine-containing alkyl group or a fluorine-containing alkyl group having ether bond.

For example, preferred are norbornene derivatives represented by the formula (17):

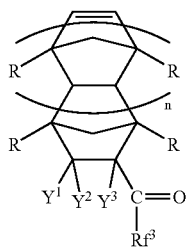

wherein $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; $Rf^3$, R and n are as defined above.

In the formula (17), it is preferable that $Y^1$ and $Y^2$ are H and $Y^3$ is F or $CF_3$, or $Y^1$ and $Y^2$ are F and $Y^3$ is F or $CF_3$.

Examples of the norbornene derivative having a fluorine-containing ketone structure of the present invention are:

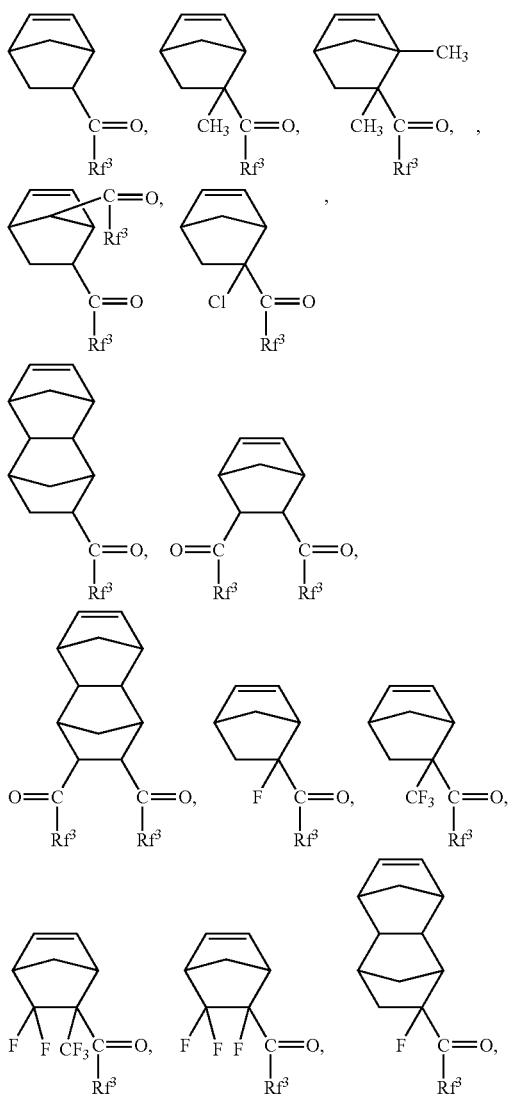

and the like.

In the norbornene derivatives of the formulae (5), (6), (7), (17) and the above-exemplified norbornene derivatives, $Rf^3$ is selected from fluorine-containing alkyl groups having 1 to 10 carbon atoms or fluorine-containing alkyl groups having 1 to 10 carbon atoms and ether bond.

$Rf^3$ is an alkyl group or alkyl group having ether bond in which a part or the whole of hydrogen atoms thereof are replaced with fluorine atoms, and halogen atoms other than fluorine such as Cl or Br may be partly contained therein.

Particularly preferred are perfluoroalkyl groups or perfluoroalkyl groups having ether bond because transparency can be imparted. For example, there are:

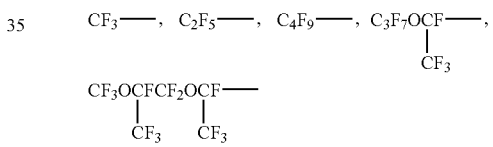

and the like, and among them, $CF_3$ is preferred particularly from the viewpoint of enhancement of transparency.

Those novel norbornene derivatives having a fluorine-containing ketone structure are useful as a starting monomer for a resist polymer when used as a comonomer of a fluorine-containing polymer and contained as a structural unit because dry etching resistivity of the polymer can be enhanced while maintaining transparency.

Those novel norbornene derivatives are also preferred because the ketone structure is hydrated under acidic condition, which makes it possible to generate hemi-acetal:

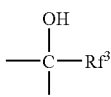

comparatively stably and makes the resist soluble in an alkaline solution.

The second of the norbornene derivatives of the present invention is one in which a moiety of fluorine-containing alcohol structure:

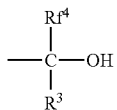

is bonded directly to the norbornene backbone.

The norbornene derivative is one having a fluorine-containing alcohol structure represented by the formula (8):

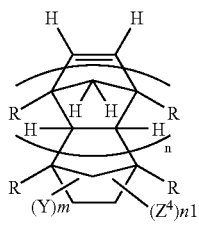

wherein $Z^4$ is the same or different and each is:

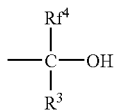

in which $Rf^4$ is the same or different and each is a fluorine-containing alkyl group having 1 to 10 carbon atoms or a fluorine-containing alkyl group which has 1 to 10 carbon atoms and ether bond, $R^3$ is H or a hydrocarbon group having 1 to 10 carbon atoms; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6.

In the norbornene derivative may be contained one or a plurality of moieties $Z^4$ of fluorine-containing alcohol, and it is generally preferable that one or two moieties are bonded. Examples thereof are:

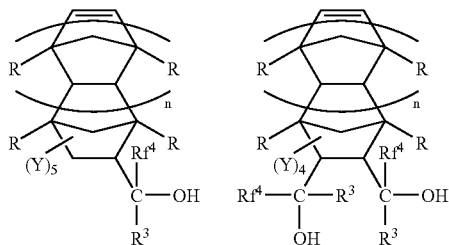

wherein Y, $Rf^4$, $R^3$, R and n are as defined in the formula (8).

In those norbornene derivatives having fluorine-containing alcohol structure, it is preferable that Y is selected from those of the above-mentioned norbornene derivatives having ketone structure, and particularly preferably is F, a fluorine-containing alkyl group or a fluorine-containing alkyl group having ether bond because transparency can be enhanced when used for a resist.

For example, preferred are norbornene derivatives represented by the formula (18):

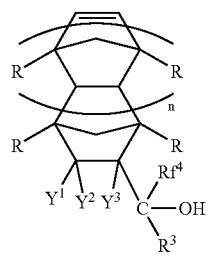

wherein $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; $Rf^4$, $R^3$, R and n are as defined above.

In the norbornene derivatives of the formula (18), it is preferable that $Y^1$ and $Y^2$ are H and $Y^3$ is F or $CF_3$, or $Y^1$ and $Y^2$ are F and $Y^3$ is F or $CF_3$.

Examples of the norbornene derivative having fluorine-containing alcohol structure of the present invention are:

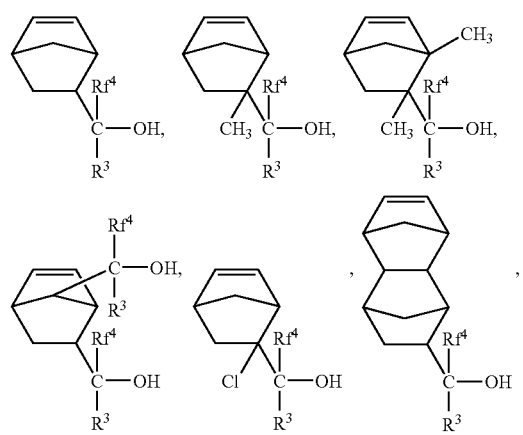

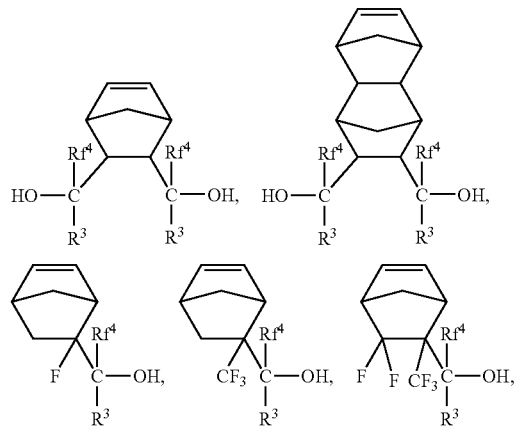

-continued

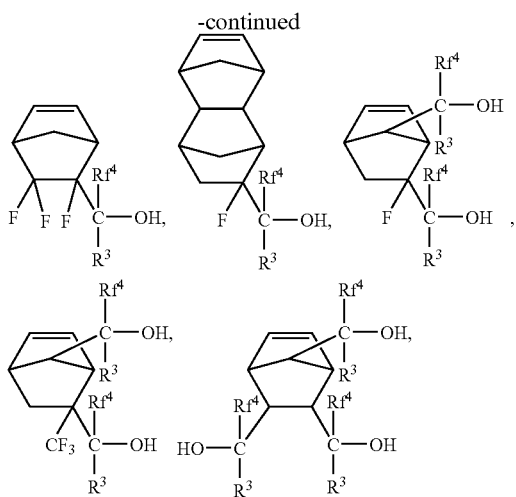

and the like.

In those norbornene derivatives having fluorine-containing alcohol structure, $Rf^4$ is selected from those which are the same as $Rf^3$ mentioned in the above-mentioned norbornene derivatives having fluorine-containing ketone structure. Preferred examples thereof are also the same as those of $Rf^3$.

$R^3$ is selected from H or hydrocarbon groups having 1 to 10 carbon atoms, for example, an alkyl group or aryl group having 1 to 10 carbon atoms or an alkyl group which has 1 to 10 carbon atoms and may have ether bond. Examples of preferred $R^3$ are:

H, $CH_3$, $C_2H_5$, $C_4H_9$,

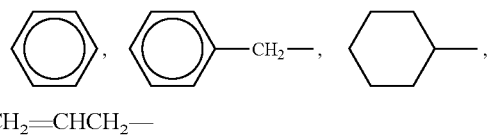

$CH_2$=$CHCH_2$— and the like.

The third of the norbornene derivatives of the present invention is one in which a moiety of fluorine-containing tertiary alcohol structure:

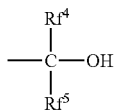

is bonded directly to the norbornene backbone, and is a novel compound which is not disclosed in patent publications and technical literatures.

Such a novel norbornene derivative is one having a fluorine-containing tertiary alcohol structure represented by the formula (9):

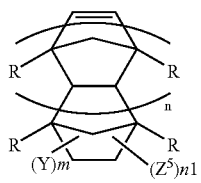

wherein $Z^5$ is the same or different and each is:

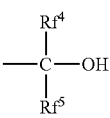

in which $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6.

The norbornene derivative may have one or a plurality of moieties $Z^5$ of fluorine-containing tertiary alcohol structure, and particularly the norbornene derivative having one or two moieties is preferred.

For example, there are a norbornene derivative having a fluorine-containing tertiary alcohol structure represented by the formula (10):

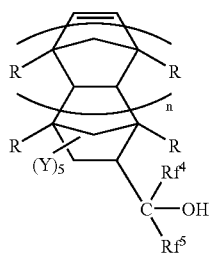

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond;

Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5, and a norbornene derivative having a fluorine-containing alcohol structure represented by the formula (11):

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond;

Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5.

The functional group Y in those norbornene derivatives having a fluorine-containing tertiary alcohol structure is H, F, Cl, an alkyl group or fluorine-containing alkyl group having 1 to 10 carbon atoms or a fluorine-containing alkyl group having 1 to 10 carbon atoms and ether bond, and it is particularly preferable that the functional group Y is F, a fluorine-containing alkyl group or a fluorine-containing alkyl group having ether bond because transparency is enhanced when the norbornene derivative is used for a resist. It is particularly preferable that at least one of Y is F or $CF_3$.

For example, there are preferably norbornene derivatives having fluorine-containing alcohol structure represented by the formula (12):

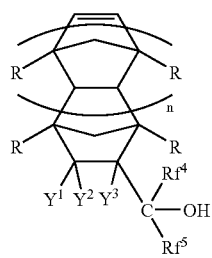

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond;

$Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms;

n is 0 or an integer of from 1 to 5; at least one of $Y^1$, $Y^2$ and $Y^3$ is F or a fluorine-containing alkyl group which has 1 to 10 carbon atoms and may have ether bond.

In the formula (12), it is preferable that $Y^1$ and $Y^2$ are H and $Y^3$ is F or $CF_3$, and $Y^1$ and $Y^2$ are F and $Y^3$ is F or $CF_3$, because transparency can be improved more.

Examples of the preferred norbornene derivative having fluorine-containing tertiary alcohol structure are:

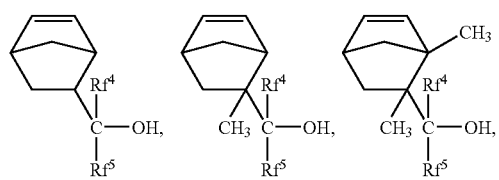

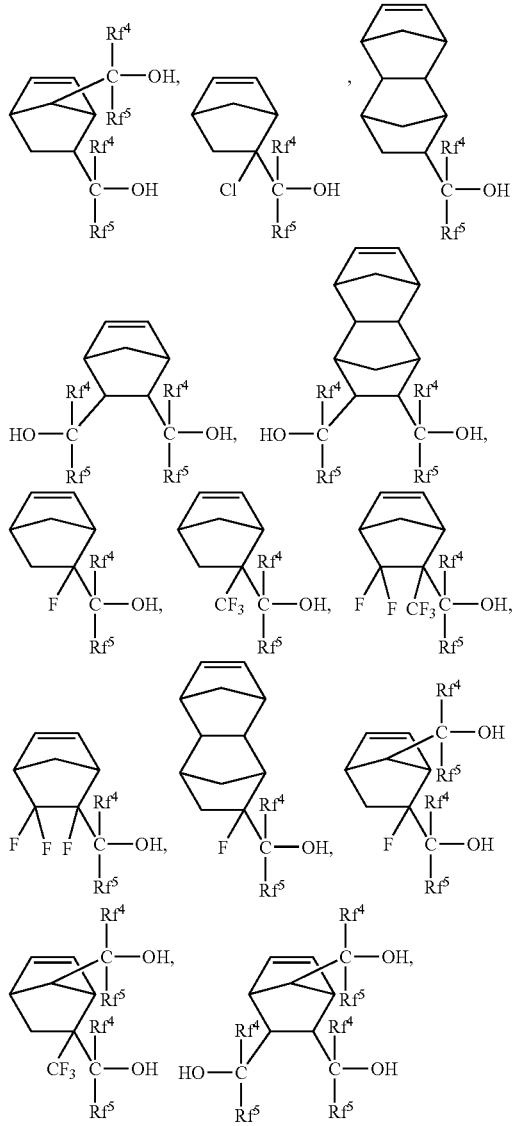

and the like.

In the above examples of the norbornene derivative, $Rf^4$ and $Rf^5$ may be the same or different, and are selected from fluorine-containing alkyl groups having 1 to 10 carbon atoms or fluorine-containing alkyl groups having 1 to 10 carbon atoms and ether bond.

$Rf^4$ and $Rf^5$ are those obtained by replacing a part or the whole of hydrogen atoms of an alkyl group or an alkyl group having ether bond with fluorine atoms and may have partly halogen atoms other than F such as Cl and Br.

It is particularly preferable that $Rf^4$ and $Rf^5$ are perfluoroalkyl groups or perfluoroalkyl groups having ether bond from the point that acidity of OH group can be enhanced and transparency can be imparted. Preferred examples thereof are:

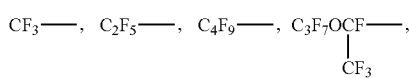

-continued

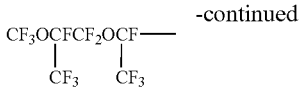

and the like, and among them, $CF_3$ is preferred particularly from the viewpoint of enhancement of transparency.

Those exemplified novel norbornene derivatives having a fluorine-containing tertiary alcohol structure, particularly those having F in the norbornene backbone are useful as a starting monomer for a resist polymer (particularly for $F_2$ resist) because the polymer having high transparency can be provided, acidity of OH group is high due to an effect of $Rf^4$ and $Rf^5$, solubility in an alkaline solution (a developing solution for a resist) can be imparted to the polymer and further dry etching resistivity of the polymer can be enhanced due to an effect of the norbornene backbone.

When used as a starting material for a resist polymer, particularly as a positive type resist, it is preferable to use the above-mentioned norbornene derivatives having a fluorine-containing alcohol structure in which hydroxyl thereof has a protective acid-reactive functional group changing to hydroxyl due to reaction with an acid.

The structure of the above-mentioned norbornene derivatives having a fluorine-containing alcohol structure is concretely one in which OH group is replaced with the protective acid-reactive functional group —$OQ^1$. Examples thereof are the same as those raised as the preferred examples of the norbornene derivative having a fluorine-containing alcohol structure in which OH group is replaced with —$OQ^1$. Those norbornene derivatives having the protective acid-reactive functional group are also novel compounds which have not disclosed in any literatures.

In those norbornene derivatives having the protective acid-reactive functional group, examples of the preferred protective acid-reactive functional group —$OQ^1$ (protective group $Q^1$) are:

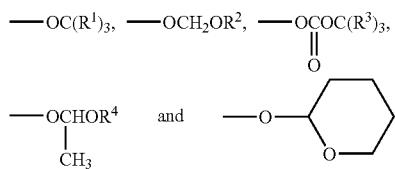

More concretely there are:

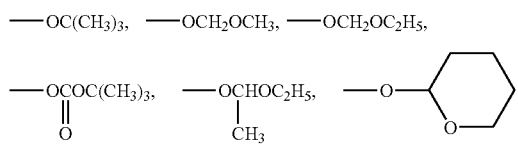

and the like.

More preferable examples are —O—$C(CH_3)_3$, —$OCH_2OCH_3$ and —$OCH_2OC_2H_5$.

Then explained below is the fluorine-containing polymer having a ring structure in its trunk chain which has a number average molecular weight of from 500 to 1,000,000 and is represented by the formula (13):

-(M1)-(M2)-(N)- wherein M1 is a structural unit derived from at least one selected from the fluorine-containing norbornene derivatives represented by the formulae (5) to (12) and the fluorine-containing norbornene derivatives of the formulae (5) to (12) having the protective acid-reactive functional group —$OQ^1$ protecting hydroxyl;

M2 is a structural unit obtained from a fluorine-containing ethylenic monomer which has 2 or 3 carbon atoms and is capable of giving at least one fluorine atom to a trunk chain;

N is a structural unit derived from monomer copolymerizable with the structural units M1 and M2, and the structural units M1, M2 and N are contained in amounts of from 1 to 99% by mole, from 1 to 99% by mole and from 0 to 98% by mole, respectively.

The structural unit M1 is a structural unit derived from the above-mentioned novel fluorine-containing norbornene derivative.

Preferred fluorine-containing ethylenic monomer of the structural unit M2 is a monomer having 2 or 3 carbon atoms and having at least one fluorine atom from the viewpoint of copolymerizability.

Examples thereof are tetrafluoroethylene, chlorotrifluoroethylene, vinylidene fluoride, hexafluoropropylene, vinyl fluoride and the like, and particularly preferred are tetrafluoroethylene and chlorotrifluoroethylene.

A percent by mole ratio of M1/M2 is preferably 1/99 to 70/30, more preferably 30/70 to 70/30 provided that M1+M2 is 100% by mole.

The structural unit N is an optional component and is not limited particularly as far as it is a structural unit derived from monomer copolymerizable with the structural units M1 and M2. The structural unit N may be selected optionally depending on required characteristics of the intended fluorine-containing polymer.

Examples thereof are:

Acrylic Monomer:

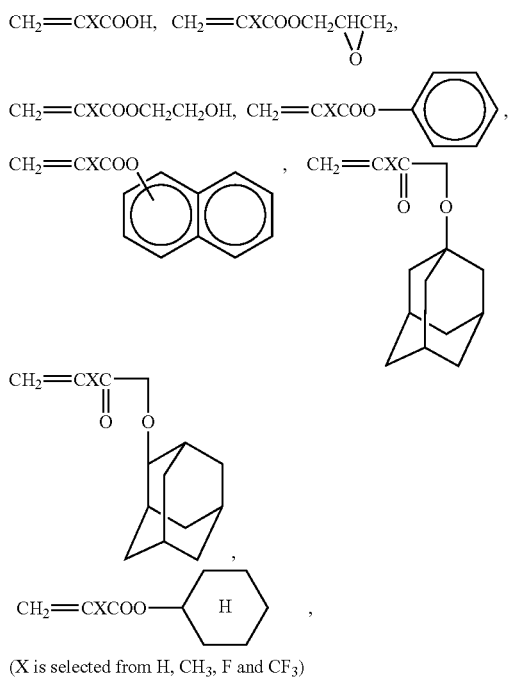

(X is selected from H, $CH_3$, F and $CF_3$)

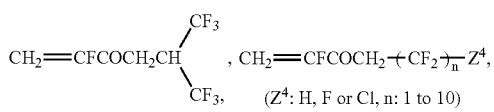

($Z^4$: H, F or Cl, n: 1 to 10)

-continued $$CH_2=CFCOCH_2\underset{CF_3}{\overset{CH_3}{\underset{|}{\overset{|}{C}}}}-CF_3,$$
$$\overset{\parallel}{O}$$

$$CH_2=CFCOCH_2CH_2-(CF_2)_n-Z^5,$$
$$\overset{\parallel}{O}$$

($Z^5$: H, F or Cl, n: 1 to 10)

$$CH_2=CFCOCH_2CF(OCF_2CF)_n-F,$$
$$\overset{\parallel}{O} \quad \overset{|}{CF_3} \quad \overset{|}{CF_3}$$

(n: 1 to 5)

$$CH_2=CFC-OCH_2CF_2(OCF_2CF_2)_n-F,$$
$$\overset{\parallel}{O}$$

(n: 1 to 30)

$$CH_2=\overset{CH_3}{\underset{|}{C}}CO-(CH_2)_m(CF_2)_n-Z^4,$$
$$\overset{\parallel}{O}$$

(m: 1 or 2, $Z^4$: H, F or Cl, n: 1 to 10)

$$CH_2=\overset{CH_3}{\underset{|}{C}}COCH_2CH\overset{CF_3}{\underset{CF_3}{\overset{|}{<}}},$$
$$\overset{\parallel}{O}$$

$$CH_2=CHCO-(CH_2)_m(CF_2)_n-Z^4,$$
$$\overset{\parallel}{O}$$

(m: 1 or 2, $Z^4$: H, F or Cl, n: 1 to 10)

$$CH_2=CHCOCH_2CH\overset{CF_3}{\underset{CF_3}{\overset{|}{<}}}, \quad CH_2=CFCO-\underset{F}{\overset{F}{\bigcirc}}-F,$$
$$\overset{\parallel}{O}$$

$$CH_2=C-CO-\underset{F}{\overset{F}{\bigcirc}}-F,$$
$$\overset{\parallel}{O}$$

$$CH_2=\overset{CH_3}{\underset{|}{C}}CO-\underset{F}{\overset{F}{\bigcirc}}-F,$$
$$\overset{\parallel}{O}$$

$$CH_2=\overset{CF_3}{\underset{|}{C}}-COCH_2CH\overset{CF_3}{\underset{CF_3}{\overset{|}{<}}}, \quad CH_2=\overset{CF_3}{\underset{|}{C}}-CCH_2-(CF_2)_n-Z^4,$$
$$\overset{\parallel}{O} \qquad\qquad\qquad \overset{\parallel}{O}$$

$$CH_2=\overset{CF_3}{\underset{|}{C}}-COCH_2CH_2-(CF_2)_n-Z^5,$$
$$\overset{\parallel}{O}$$

($Z^4$ and $Z^5$: H, F or Cl, n: 1 to 10)

-continued $$CH_2=\overset{CF_3}{\underset{|}{C}}-CO-\underset{F}{\overset{F}{\underset{F}{\bigcirc}}}-F,$$
$$\overset{\parallel}{O}$$

and the like.

Styrene monomer:

$$CH_2=CH-\bigcirc, \quad CH_2=CH-\bigcirc-OH,$$

$$CF_2=CF-\bigcirc, \quad CF_2=CF-\underset{F}{\overset{F}{\underset{F}{\bigcirc}}}-F,$$

$$CF_2=CF-\bigcirc-OH, \quad CH_2=CH-\bigcirc-OH,$$

$$CH_2=CH-\underset{F}{\overset{F}{\underset{F}{\bigcirc}}}-OH,$$

$$CF_2=CF-\underset{F}{\overset{F}{\underset{F}{\bigcirc}}}-OH \quad \text{and}$$

$$CH_2=CH-\bigcirc-(CH_2)_n-\overset{CF_3}{\underset{CF_3}{\overset{|}{C}}}-OH$$

wherein n is 0 or an integer of 1 or 2,
$CH_2=CH_2$, $CH_2=CHCH_3$, $CH_2=CHCl$ and the like.

Maleic Acid Monomer:

$$\underset{\underset{O}{\overset{|}{\diagdown}}/}{\overset{CH=CH}{\overset{|}{\diagup}\underset{|}{\diagdown}}}\underset{C=O,}{\overset{}{}} \quad \overset{CH=CH}{\underset{HOOC\quad COOH,}{}}$$

$$\overset{CH=CH}{\underset{COOR}{\overset{|}{\phantom{X}}\underset{COOR}{\overset{|}{\phantom{X}}}}} \quad \text{and} \quad \overset{CH=CH}{\underset{COOR}{\overset{|}{\phantom{X}}\underset{COOH}{\overset{|}{\phantom{X}}}}}$$

wherein R is a hydrocarbon group having 1 to 20 carbon atoms.

Allyl Monomer:
CH$_2$=CHCH$_2$Cl, CH$_2$=CHCH$_2$OH, CH$_2$=CHCH$_2$COOH,
CH$_2$=CHCH$_2$Br and the like.

Allyl Ether Monomer:
CH$_2$=CHCH$_2$OR (R is a hydrocarbon group having 1 to 20 carbon atoms),
CH$_2$=CHCH$_2$OCH$_2$—(CF$_2$)$_n$X (n: from 1 to 10, X: H, Cl or F),
CH$_2$=CHCH$_2$OCH$_2$CH$_2$COOH,

Preferred are the structural units derived from these ethylenic monomers exemplified above.

Among them, particularly preferred are structural units derived from norbornene derivatives other than the above-mentioned structural unit (M1). Examples thereof are those represented by the formula:

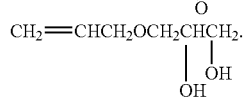

wherein A, B, C and D are H, F, an alkyl group having 1 to 10 carbon atoms or a fluorine-containing alkyl group having 1 to 10 carbon atoms, m is 0 or an integer of from 1 to 3, any one of A, B, C and D has fluorine atom.

Examples thereof are:

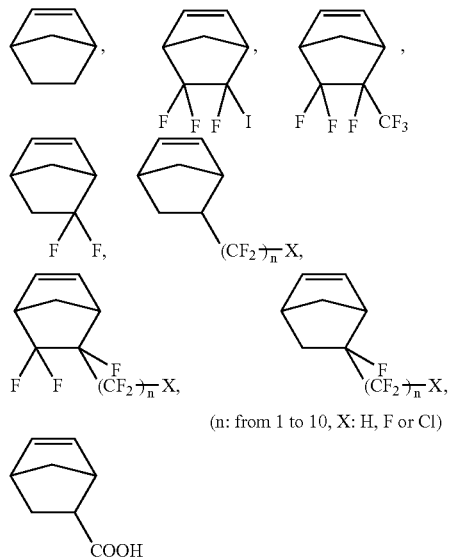

(n: from 1 to 10, X: H, F or Cl)

and the like.

In addition, there are structural units derived from alicyclic monomers such as:

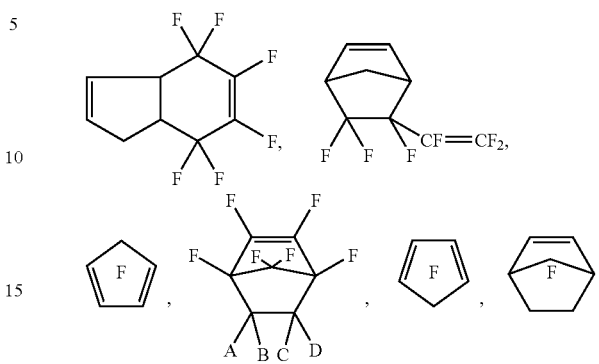

and the like, wherein A, B, C and D are H, F, an alkyl group having 1 to 10 carbon atoms or a fluorine-containing alkyl group having 1 to 10 carbon atoms.

A molecular weight of the fluorine-containing polymer of the formula (13) can be selected in the range of from 500 to 1,000,000 in a number average molecular weight depending on application, purpose and form in use. The molecular weight is preferably from 1,000 to 700,000, more preferably from about 2,000 to about 500,000. If the molecular weight is too low, heat resistance and mechanical properties of the obtained polymer film are apt to be insufficient, and too high molecular weight is disadvantageous from the viewpoint of processability. Particularly in the case of use in the form of coating material for forming a thin coating film, too high molecular weight is disadvantageous from the viewpoint of film forming property. The molecular weight is preferably not more than 200,000, particularly preferably not more than 100,000.

The fluorine-containing polymer of the formula (13) of the present invention can be obtained by copolymerizing, through known method, the novel fluorine-containing norbornene derivative M1 of the present invention, the fluorine-containing ethylenic monomer M2 and as case demands, a monomer corresponding to the optional component N. For the polymerization, radical polymerization method, anion polymerization method, cation polymerization method and the like can be employed. Among them, the radical polymerization method is preferably used from the point that each monomer exemplified below to obtain the polymer of the present invention has good radial polymerizability, control of composition and molecular weight is easy and production in an industrial scale is easy. Namely, in order to initiate the polymerization, means for initiation is not limited particularly as far as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, polymerization temperature, etc. The components of the copolymer to be produced can be controlled by the starting monomer components.

Examples of the preferred fluorine-containing polymer of the formula (13) are, for instance, those mentioned below.

(I) A fluorine-containing copolymer of -(M1)-(M2)- in which the structural unit M2 is a structural unit derived from TFE or CTFE, the structural unit M1 is a structural unit derived from the norbornene derivative having a fluorine-containing alcohol structure of the formula (15) and the structural units M2 and M1 are contained in amount of from 30 to 70% by mole, preferably from 40 to 65% by mole and from 30 to 70% by mole, preferably from 35 to 60% by mole, respectively.

This fluorine-containing copolymer is preferred from the viewpoint of high transparency and excellent dry etching resistivity.

Particularly preferred is a fluorine-containing polymer represented by the formula (13)-1:

-(M1-1)-(M1-2)-(M2)-(N)-        (13)-1 wherein the structural unit M2 is as defined in the formula (13);
the structural unit M1-1 is a structural unit derived from the norbornene derivatives having a fluorine-containing alcohol structure of the formulae (8) to (12);
the structural unit M1-2 is a structural unit derived from the norbornene derivatives having a fluorine-containing alcohol structure of the formulae (8) to (12) having a protective acid-reactive functional group —$OQ^1$ protecting hydroxyl;
the structural unit N is a structural unit derived from monomer copolymerizable with the structural units M1-1, M1-2 and M2, provided that (M1-1)+(M1-2)+(M2) is 100% by mole, a percent by mole ratio of ((M1-1)+(M1-2))/M2 is 30/70 to 70/30, and
the structural units M1-1, M1-2, M2 and N are contained in amounts of from 1 to 98% by mole, from 1 to 98% by mole, from 1 to 98% by mole and from 0 to 97% by mole, respectively. This polymer is preferred because adhesion to a substrate such as a silicon wafer and wettability to a developing solution are enhanced owing to OH group in the structural unit M1-1.

In the formula (13)-1, provided that (M1-1)+(M1-2) is 100% by mole, a percent by mole ratio of (M1-1)/(M1-2) is optionally selected in the range of 90/10 to 40/60. The ratio of (M1-1)/(M1-2) is preferably 90/10 to 50/50, more preferably 85/15 to 60/40. If the proportion of (M1-1) is too large, an un-exposed portion also becomes soluble and a resist pattern cannot be formed. Even if the un-exposed portion does not become soluble, a thickness of the un-exposed portion is decreased too much and the form of resist pattern becomes round and resolution is lowered. If the proportion of (M1-1) is too small, there arise problems that since adhesion to undercoating becomes insufficient, the resist is peeled at developing and a developing solution is apt to be repelled at developing, which makes it difficult to obtain uniform developing.

Preferred structural unit M2 is one derived from tetrafluoroethylene or chlorotrifluoroethylene.

(II) A fluorine-containing copolymer of (M1)-(M2)-(N3)- in which the structural unit M2 is as defined in the formula (13), the structural unit M1 is a structural unit derived from the norbornene derivatives having a fluorine-containing alcohol structure of the formulae (8) to (12), the structural unit N3 is a structural unit derived from monomer selected from cyclic unsaturated aliphatic hydrocarbon compounds of the structural unit N3 explained infra in the chemically amplifying type photoresist composition, and the structural units M2, M1 and N3 are contained in amounts of from 40 to 60% by mole, from 10 to 45% by mole and from 1 to 50% by mole, respectively.

This fluorine-containing copolymer is preferred from the point that the amount of the functional group contained in the structural unit M1 can be adjusted without lowering dry etching resistivity. Particularly preferred N3 are those selected from the above-mentioned norbornene derivatives.

Among them, it is preferable that the structural unit M2 is a structural unit derived from tetrafluoroethylene or chlorotrifluoroethylene.

(III) A fluorine-containing copolymer of -(M1)-(M2)-(N1)- in which the structural unit M2 is as defined in the formula (13), the structural unit M1 is a structural unit derived from the norbornene derivatives having a fluorine-containing alcohol structure of the formulae (8) to (12), the structural unit N1 is a structural unit derived from monomer selected from ethylenic monomers having COOH group or an acid-labile functional group $COOQ^1$ which is converted to carboxyl due to action of an acid, and the structural units M2, M1 and N1 are contained in amounts of from 10 to 60% by mole, from 1 to 50% by mole and from 5 to 70% by mole, respectively.

This fluorine-containing copolymer is preferred from the point that solubility of the fluorine-containing polymer in a developing solution can be enhanced and high sensitivity and high resolution can be obtained. Particularly preferred structural unit N1 is one having fluorine atom. Concretely from the viewpoint of capability of enhancing transparency, preferred is a structural unit derived from a monomer having functional group $COOQ^1$ such as a fluorine-containing acrylic monomer, a fluorine-containing allyl monomer, a fluorine-containing styrene monomer or a monomer explained infra as N1-1 or N1-2 having a fluoroalkyl group in a side chain thereof among the compounds explained infra in the chemically amplifying. type photoresist composition.

(IV) A fluorine-containing polymer represented by:

-(M1-3)-(M2)-(N2)-(N)-        (13)-2 wherein the structural unit M2 is as defined in the formula (13),
the structural unit M1-3 is a structural unit derived from at least one selected from the norbornene derivatives of the formulae (5) to (12) or the norbornene derivatives of the formulae (5) to (12) having a protective acid-reactive functional group —$OQ^1$ protecting hydroxyl thereof,
the structural unit N2 is one which comprises a cyclic aliphatic unsaturated hydrocarbon copolymerizable with the monomers constituting the structural units M1-3, M2 and N and is derived from a cyclic aliphatic unsaturated hydrocarbon having COOH group or an acid-labile functional group —$COOQ^1$ which can be converted to carboxyl due to action of an acid,
the structural unit N is a structural unit derived from monomer copolymerizable with monomers constituting the structural units M1-3, M2 and N2,
provided that (M1-3)+M2+N2 is 100% by mole, a percent by mole ratio of ((M1-3)+N2)/M2 is 70/30 to 30/70, and
the structural unit M1-3, M2, N2 and N are contained in amounts of from 1 to 98% by mole, from 1 to 98% by mole, from 1 to 98% by mole and from 0 to 97% by mole, respectively.

This fluorine-containing copolymer is preferred from the point that solubility of the fluorine-containing polymer in a developing solution can be enhanced, high sensitivity and high resolution can be obtained and further dry etching resistivity can be enhanced. Particularly preferred structural unit N2 is a structural unit derived from norbornene derivative having COOH group or an acid-labile group —$COOQ^1$ which can be converted to carboxyl due to action of an acid, and further preferred are norbornene derivatives having fluorine atom or a fluorine-containing alkyl group. For example, from the point that transparency can be further enhanced, preferred is a structural unit derived from norbornene derivatives represented by the formula:

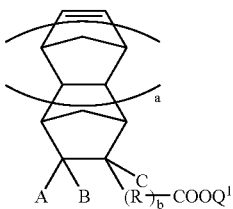

wherein A, B and C are H, F, alkyl groups having 1 to 10 carbon atoms or fluorine-containing alkyl groups having 1 to 10 carbon atoms, R is a divalent hydrocarbon group having 1 to 20 carbon atoms, a fluorine-containing alkylene group having 1 to 20 carbon atoms or a fluorine-containing alkylene group having 2 to 100 carbon atoms and ether bond, a is 0 or an integer of from 1 to 3, b is 0 or 1, —COOQ$^1$ is COOH group or an acid-labile functional group which can be converted to carboxyl due to action of an acid, when b is 0 or R does not have fluorine atom, any one of A, B and C is fluorine atom or a fluorine-containing alklyl group.

Particularly preferred example is a fluorine-containing polymer represented by the formula (13)-3:

-(M1-1)-(M2)-(N2-1)-(N)-                        (13)-3 wherein the structural unit M1-1 and M2 are as defined in the formula (13)-1,
the structural unit N2-1 is a structural unit derived from the norbornene derivatives represented by the formula (3)-1:

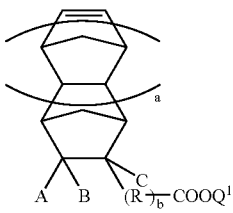

wherein —COOQ$^1$ is an acid-labile functional group which can be converted to carboxyl due to action of an acid, A, B, C, R, a and b are as defined above,
the structural unit N is a structural unit derived from monomer copolymerizable with monomers constituting the structural units M1-1, M2 and N2-1,
provided that (M1-1)+(M2)+(N2-1) is 100% by mole, a percent by mole ratio of ((M1-1)+(N2-1))/(M2) is 70/30 to 30/70, and provided that (M1-1)+(N2-1) is 100% by mole, a percent by mole ratio of (M1-1)/(N2-1) is 95/5 to 60/40, and
the structural unit M1-1, M2, N2-1 and N are contained in amounts of from 1 to 98% by mole, from 1 to 98% by mole, from 1 to 98% by mole and from 0 to 97% by mole, respectively.

Those polymers are preferred because a fine resist pattern having a high resolution can be formed in F2 lithography while maintaining high sensitivity.

In the fluorine-containing polymer of the formula (13)-3, a percent by mole ratio of (M1-1)/(N2-1) is optionally selected in a range of from 95/5 to 40/60, preferably from 90/10 to 50/50, more preferably from 85/15 to 60/40. If the proportion of (M1-1) is too large, an unexposed portion also becomes soluble and a resist pattern cannot be formed. Even if the un-exposed portion does not become soluble, a thickness of the un-exposed portion is decreased, a form of the resist pattern becomes round and resolution is lowered. If the proportion of (M1-1) is too small, there arises a problem that adhesion to undercoating becomes insufficient, peeling occurs at developing, and a developing solution is apt to be repelled at developing, which makes it difficult to obtain uniform developing. Further if the proportion of (N2-1) is too small, swelling of the un-exposed portion easily occurs, inflation of a pattern form occurs and a residue of the resist polymer (un-dissolved portion) is apt to arise at an exposed portion, which are not preferred.

It is particularly preferable that the structural unit M2 is a structural unit derived from tetrafluoroethylene or chlorotrifluoroethylene.

Examples of the preferred structural units N2 and N2-1 are the same as those explained infra in the chemically amplifying type photoresist composition.

A variety of combinations of M1, M2 and as case demands, N of the polymer of the formula (13) of the present invention can be selected from the above-mentioned examples depending on application, physical properties (particularly glass transition point, melting point, etc.) and functions (transparency, refractive index, etc.). Usually functions of a functional group mentioned infra are imparted by M1, and other functions are adjusted by selecting kind and proportion of M2 and N.

The so-obtained fluorine-containing polymer of the formula (13) has good heat resistance, is non-crystalline and has high transparency in a wide wavelength range including a vacuum ultraviolet region and a low refractive index, and therefore can be used for optical applications such as plastic optical fiber and semi-conductor applications such as a resist and interface insulation film.

The present invention also relates to the chemically amplifying type photoresist composition containing, as a binder, a fluorine-containing polymer comprising a specific fluorine-containing norbornene derivative unit having an acid-reactive functional group.

The chemically amplifying type photoresist composition comprises a resin (polymer) component and a photoacid generator, and an acid is generated from the acid generator on an energy-irradiated portion of the photoresist and a catalytic action of the acid is used. In a positive type chemically amplifying type photoresist, the acid generated on the energy-irradiated portion is then dispersed by heat-treatment (post exposure bake: hereinafter abbreviated to PEB) to release acid-labile or acid-decomposable functional group of the resin and regenerate an acid, thereby making the energy-irradiated portion soluble in alkali. Also in a negative type chemically amplifying type photoresist, generally the resin component has a functional group being capable of undergoing condensation reaction due to action of an acid, and is soluble in alkali. The negative type photoresist comprises a crosslinking agent in addition to the resin component and an acid generator.

The chemically amplifying type photoresist composition of the present invention can be used on the above-mentioned positive type and negative type photoresists, and comprises:

(A) a fluorine-containing polymer having OH group and/or a protective acid-reactive functional group —OQ$^1$ protecting hydroxyl group,
(B) a photoacid generator, and
(C) a solvent.

The present inventors have found that the fluorine-containing polymer (A) having a structural unit derived from a specific norbornene derivative having OH group and/or an acid-reactive group and fluorine atom or a fluoroalkyl group in one molecule is especially high in transparency against light in an ultraviolet region and is excellent in properties of resist such as etching resistivity, reactivity with an acid and solubility in a developing solution.

The fluorine-containing polymer (A) having an acid-reactive group which is used on the chemically amplifying type photoresist composition of the present invention is a fluorine-containing polymer represented by the formula (14):

wherein M1a is a structural unit derived from the norbornene derivatives having a fluorine-containing alcohol structure of the formulae (8) to (12) and/or the norbornene derivatives having a fluorine-containing alcohol structure of the formulae (8) to (12) in which hydroxyl group is protected with a protective acid-reactive functional group —OQ$^1$; M2 and N are as defined above.

In the photoresist composition of the present invention, the fluorine-containing polymer (A) contains the above-mentioned structural units M1a and M2 as essential components. Examples of the acid-reactive functional group are functional groups —OQ$^1$ and —COOQ$^1$ undergoing dissociation or decomposition reaction due to action of an acid or cation or functional groups Q$^2$ undergoing condensation reaction due to action of an acid or cation. Those functional groups may be introduced to the structural unit M1a or the optional component N but is contained in at least one of them.

Those reactions may be initiated at low temperature or only by heating to high temperature.

Then the fluorine-containing polymer to be used on the positive type chemically amplifying type photoresist composition is explained below.

When the composition is used on a positive type resist, it is preferable that the functional groups —OQ$^1$ and —COOQ$^1$ are functional groups which can be converted to hydrophilic groups due to action of an acid. Further it is preferable that those functional groups are functional groups which can be converted to groups being capable of making the fluorine-containing polymer soluble in an alkaline solution.

When the acid-labile or acid-decomposable functional group is introduced to the structural unit M1a, the structural unit M1a is a structural unit derived from a monomer selected from the compounds obtained by protecting hydroxyl group of the norbornene derivatives having a fluorine-containing alcohol structure of the formulae (8) to (12) with a protective acid-reactive functional group —OQ$^1$. The protective acid-reactive functional group —OQ$^1$ in the structural unit M1a can be converted to —OH group due to action of an acid.

Examples of the protective acid-reactive functional group —OQ$^1$ contained in the structural unit M1a are:

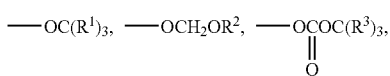

-continued

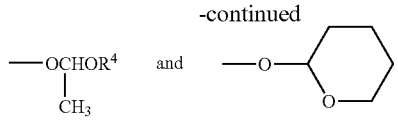

and more concretely there are:

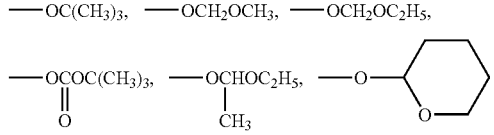

and the like. More preferable examples are —O—C(CH$_3$)$_3$, —OCH$_2$OCH$_3$ and —OCH$_2$OC$_2$H$_5$ from the viewpoint of good transparency.

Therefore in this case, examples of the structural unit M1a which can be used preferably are the same as the preferable examples of the norbornene derivatives having a fluorine-containing alcohol structure of the formulae (8) to (12) in which OH group is replaced with —OQ$^1$ exemplified above.

When the functional group —OQ$^1$ is introduced to the structural unit M1a, OH group after the dissociation or decomposition reaction with an acid is high in acidity and can impart solubility in an alkaline solution (resist developing solution) to the polymer.

When the acid-labile or acid-decomposable functional group is introduced to the structural unit N, examples of preferred acid-labile or acid-decomposable functional group are functional groups which can be converted to —OH group, —COOH group, —SO$_3$H group and the like due to action of an acid.

Examples of the acid-labile or acid-decomposable functional group are:

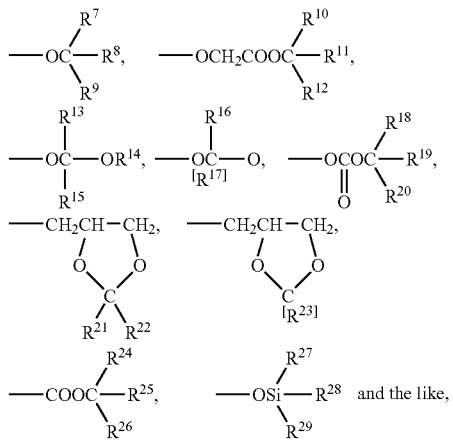

wherein R$^7$, R$^8$, R$^9$, R$^{10}$, R$^{11}$, R$^{12}$, R$^{14}$, R$^{15}$, R$^{18}$, R$^{19}$, R$^{20}$ R$^{21}$, R$^{22}$, R$^{24}$, R$^{25}$, R$^{26}$, R$^{27}$, R$^{28}$ and R$^{29}$ are the same or different and each is a hydrocarbon group having 1 to 10 carbon atoms; R$^{13}$ and R$^{16}$ are H or a hydrocarbon group having 1 to 10 carbon atoms; and R$^{17}$ and R$^{23}$ are divalent hydrocarbon groups having 2 to 10 carbon atoms.

More concretely there are:

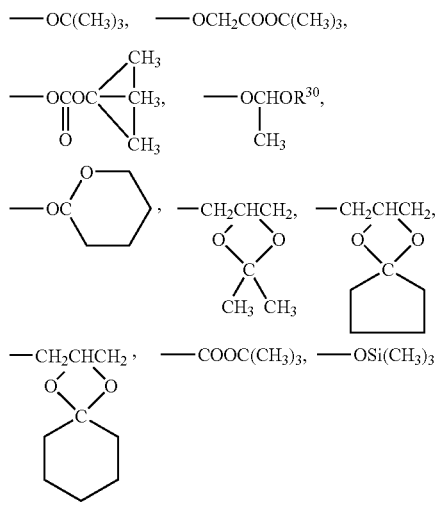

and the like, wherein $R^{30}$ is an alkyl group having 1 to 10 carbon atoms.

Particularly preferred are those converting to —OH group or —COOH group by reaction with an acid, and from the viewpoint of good solubility in a developing solution, those converting to —COOH group is preferred.

Preferred embodiment of the chemically amplifying type photoresist composition of the present invention is one which comprises:

(A) a fluorine-containing polymer having OH group or a group which can be converted to OH group by dissociation with an acid,
(B) a photoacid generator, and
(C) a solvent in which the fluorine-containing polymer (A) has a number average molecular weight of from 500 to 1,000,000 and is represented by the formula (14)-1:

-(M1a)-(M2)-(N)-  (14)-1 wherein the structural unit M1a is a structural unit derived from at least of selected from norbornene derivatives having a fluorine-containing alcohol structure represented by the formula (15):

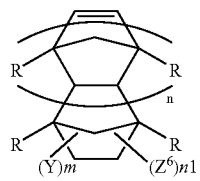

in which $Z^6$ is the same or different and each is:

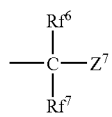

wherein $Rf^6$ and $Rf^7$ are the same or different and each is a fluorine-containing alkyl group having 1 to 10 carbon atoms or a fluorine-containing alkyl group having 1 to 10 carbon atoms and ether bond; $Z^7$ is OH group or a group dissociated due to action of an acid and converted to OH group; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6, the structural unit M2 is a structural unit derived from an ethylenic monomer having 2 or 3 carbon atoms and at least one fluorine atom, the structural unit N is a structural unit derived from monomer copolymerizable with the structural units M1a and M2, provided that M1a+M2 is 100% by mole, a percent by mole ratio of M1a/M2 is 1/99 to 70/30, and the structural unit M1a, the structural unit M2 and the structural unit N are contained in amounts of from 1 to 99% by mole, from 1 to 99% by mole and from 0 to 98% by mole, respectively.

In the structural unit M1a of the fluorine-containing polymer (A) of the formula (14)-1 of the chemically amplifying type photoresist composition, it is preferable that at least one of the substituents Y in the formula (15) is F or a fluorine-containing alkyl group which has 1 to 10 carbon atoms and may have ether bond, from the viewpoint of transparency. More concretely it is preferable that the structural unit M1a is a structural unit derived from a fluorine-containing norbornene derivative represented by the formula (16):

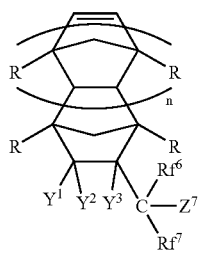

wherein $Rf^6$ and $Rf^7$ are the same or different and each is a fluorine-containing alkyl group having 1 to 10 carbon atoms or a fluorine-containing alkyl group having 1 to 10 carbon atoms and ether bond; $Z^7$ is OH group or a group dissociated due to action of an acid and converted to OH group; $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5.

From the viewpoint of transparency and dry etching resistivity, it is preferable that at least one of $Y^1$, $Y^2$ and $Y^3$ in the formula (16) is F or $CF_3$. It is particularly preferable from the viewpoint of transparency and dry etching resistivity that $Y^1$ and $Y^2$ are H and $Y^3$ is F or $CF_3$, or $Y^1$ and $Y^2$ are F and $Y^3$ is F or $CF_3$.

It is also preferable that in the formulae (15) and (16), $Rf^6$ and $Rf^7$ are a perfluoroalkyl group or a perfluoroalkyl group having ether bond from the viewpoint of transparency and are $CF_3$ particularly from the viewpoint of both transparency and dry etching resistivity.

In the formulae (15) and (16), the group $Z^7$ is a group dissociated due to action of an acid and converted to OH group. Examples of the group dissociated due to action of an acid and converted to OH group are preferably the same as the examples of the above-mentioned acid-labile or acid-decomposable functional group. Particularly preferred are:

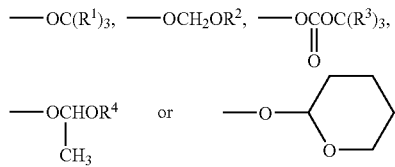

wherein $R^1$, $R^2$, $R^3$ and $R^4$ are alkyl groups having 1 to 5 carbon atoms.

In the fluorine-containing polymers (A) of the formulae (14) and (14)-1, examples of the structural unit M2 are the same as the preferred examples of the structural unit M2 of the above-mentioned novel fluorine-containing polymer, and among them, a structural unit obtained from at least one selected from tetrafluoroethylene and chlorotrifluoroethylene is particularly preferred from the viewpoint of both of transparency and dry etching resistivity.

In the chemically amplifying type photoresist composition of the present invention, in addition to OH group and protective acid-reactive functional group $-OQ^1$ (OH group or a group which can be converted to OH group by dissociation due to action of an acid) protecting hydroxyl which are introduced to the structural unit M1a of the fluorine-containing polymer (A) of the formulae (14) and (14)-1, as the optional structural unit N, a structural unit having OH group, COOH group or an acid-labile or acid-decomposable functional group may be used for the purpose of increasing an amount of the same functional group as above or introducing different kind of functional groups It is particularly preferable to introduce, to the structural unit N, COOH or an acid-labile functional group $-COOQ^1$ converted to carboxyl group due to action of an acid, from the viewpoint of enhancing resolution of a photoresist and from the point that solubility in a developing solution can be enhanced or adjusted. As a result, a good form of a pattern after developing can be obtained and scum can be decreased.

Examples of the structural unit having an acid-labile or acid-decomposable functional group are preferably the following structural units N1 and N2.

The structural unit N1 comprises an ethylenic monomer having COOH or an acid-labile functional group $-COOQ^1$ converted to carboxyl due to action of an acid, and may have or may not have fluorine atom. Example of the structural unit N1 is one represented by the formula:

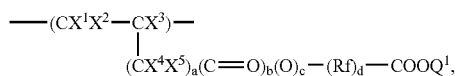

wherein $COOQ^1$ is COOH or an acid-labile functional group converted to carboxyl due to action of an acid; $X^1$ and $X^2$ are the same or different and each is H or F; $X^3$ is H, F, Cl, $CH_3$ or $CF_3$; $X^4$ and $X^5$ are the same or different and each is H, F or $CF_3$; Rf is a fluorine-containing alkylene group having 1 to 40 carbon atoms or a fluorine-containing alkylene group having 2 to 100 carbon atoms and ether bond; a is 0 or an integer of from 1 to 3; b, c and d are the same or different and each is 0 or 1.

Examples of the structural unit N1 having no fluorine atom (d=0) are as follows.

Acrylic Monomer:
$CH_2=CHCOOQ^1$, $CH_2=C(CH_3)COOQ^1$,
$CH_2=CClCOOQ^1$,

Maleic Acid Monomer:

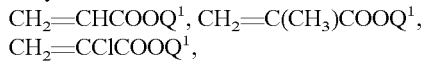

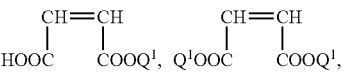

Allyl Monomer:
$CH_2=CHCH_2COOQ^1$, $CH_2=CHCH_2CH_2CH_2COOQ^1$

Styrene Monomer:

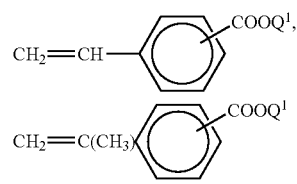

and the like.

Examples of the structural unit N1 having fluorine atom (d=0) in its trunk chain are as follows.

Fluorine-containing Acrylic Monomer:
$CH_2=CFCCOOQ^1$, $CH_2=C(CF_3)COOQ^1$ and $CF_2=CFCOOQ^1$ Fluorine-containing Allyl Monomer:
$CH_2=CFCF_2COOQ^1$, $CF_2=CFCF_2COOQ^1$ and $CH_2=CHCF_2COOQ^1$, Fluorine-containing Styrene Monomer:

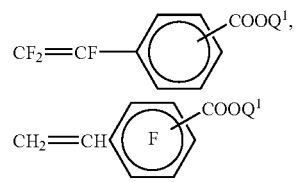

and the like.

Example of the structural unit N1 having a fluoroalkyl group (d=1) in its side chain is preferably N1-1:
$CH_2=CFCF_2O-Rf-COOQ^1$ wherein $Q^1$ and Rf are as defined in the above-mentioned N1, and is concretely:

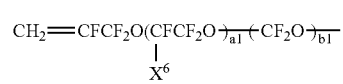

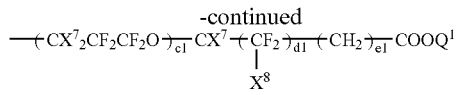

wherein a1+b1+c1 is from 0 to 30, d1 is 0 or 1, e1 is from 0 to 5, $X^6$ is F or $CF_3$, $X^7$ is H or F, $X^8$ is H, F or $CF_3$.

More concretely there are:

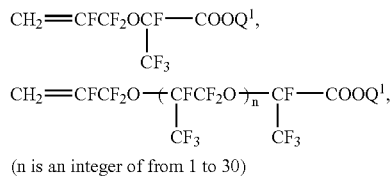

(n is an integer of from 1 to 30)

$CH_2$=$CFCF_2O$-$(CF_2CF_2O)_n$-$CF_2$-$COOQ^1$,
$CH_2$=$CFCF_2O$-$(CF_2CF_2CF_2O)_n$-$CF_2CF_2$-$COOQ^1$,
$CH_2$=$CFCF_2O$-$(CH_2CF_2CF_2O)_n$-$CH_2CF_2$-$COOQ^1$,
(n is an integer of from 1 to 30)
$CH_2$=$CFCF_2O$-$(CF_2CF_2)_n$-$COOQ^1$,
(n is an integer of from 1 to 30)

and the like.

Also the structural unit N2 is preferably N1-2:
$CF_2$=$CFO$—$Rf$—$COOQ^1$ wherein $Q^1$ and Rf are as defined in the above-mentioned N1.

The N1-2 is concretely represented by:

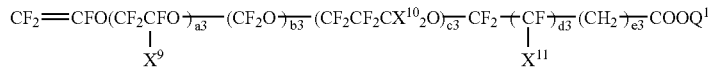

wherein a3+b3+c3 is from 0 to 30, d3 is from 0 to 2, e3 is from 0 to 5, $X^9$ and $X^{11}$ are F or $CF_3$, $X^{10}$ is H or F.

More concretely there are:

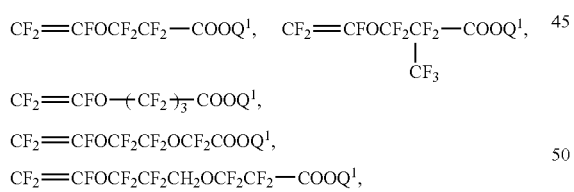

and the like.

Examples of other monomer constituting N1 are:
$CF_2$=$CFCF_2$—O—Rf—$COOQ^1$, $CF_2$=$CF$—Rf—$COOQ^1$,
$CH_2$=$CH$—Rf—$COOQ^1$, $CH_2$=$CHO$—Rf—$COOQ^1$,
(Rf is as defined above)
and the like. More concretely there are:

$CF_2$=$CF$—$CF_2OCF_2CF_2CF_2COOQ^1$,

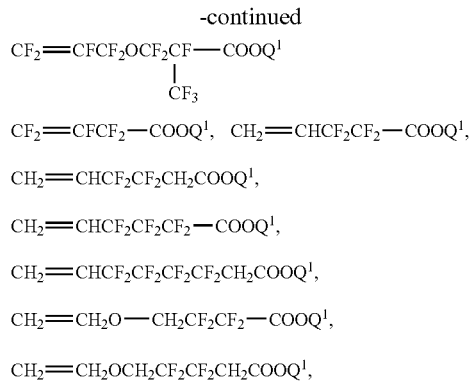

$CF_2$=$CFCF_2$—$COOQ^1$, $CH_2$=$CHCF_2CF_2$—$COOQ^1$, $CH_2$=$CHCF_2CF_2CH_2COOQ^1$, $CH_2$=$CHCF_2CF_2CF_2$—$COOQ^1$, $CH_2$=$CHCF_2CF_2CF_2CF_2CH_2COOQ^1$, $CH_2$=$CH_2O$—$CH_2CF_2CF_2$—$COOQ^1$, $CH_2$=$CH_2OCH_2CF_2CF_2CH_2COOQ^1$, and the like.

The structural unit N2 comprises a cyclic aliphatic unsaturated hydrocarbon copolymerizable with the fluorine-containing ethylenic monomer constituting M2, and further have COOH group or an acid-labile functional group —$COOQ^1$ which can be converted to carboxyl due to action of an acid. The introduction of N2 is preferred since a function of being soluble in an aqueous alkaline solution (developing solution) is enhanced and dry etching resistivity of the whole polymer can be enhanced.

The monomer constituting the structural unit N2 is an aliphatic monomer such as:

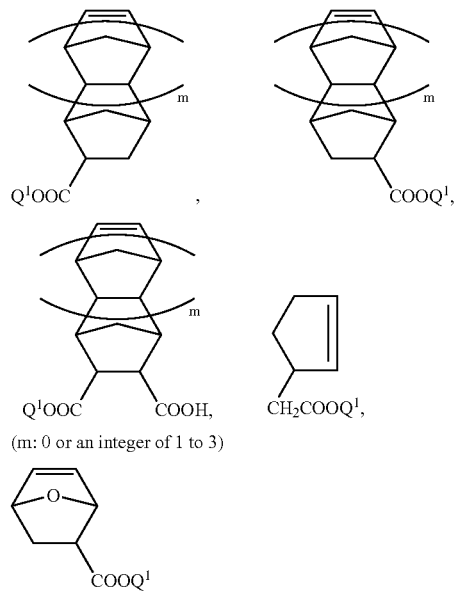

(m: 0 or an integer of 1 to 3)

Further preferred structural unit N2 is one in which a part or the whole of hydrogen atoms are replaced with fluorine atoms, which is preferred because transparency can be further imparted to the polymer.

Concretely there are fluorine-containing monomers represented by:

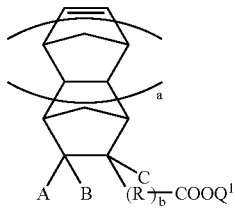

wherein A, B and C are H, F, an alkyl group having 1 to 10 carbon atoms or a fluorine-containing alkyl group having 1 to 10 carbon atoms; R is a divalent hydrocarbon group having 1 to 20 carbon atoms, a fluorine-containing alkylene group having 1 to 20 carbon atoms or a fluorine-containing alkylene group having 2 to 100 carbon atoms and ether bond; a is 0 or an integer of from 1 to 3; b is 0 or 1; $COOQ^1$ is COOH group or an acid-labile functional group; when b is 0 or R does not have fluorine atom, any one of A to C is fluorine atom or a fluorine-containing alkyl group.

In those monomers, it is preferable that any of A, B and C is fluorine atom and that when fluorine atom is not contained in A, B and C, the fluorine content of R is not less than 60%. It is further preferable that A, B and C is a perfluoroalkyl group, because transparency can be imparted to the polymer.

Concretely there are:

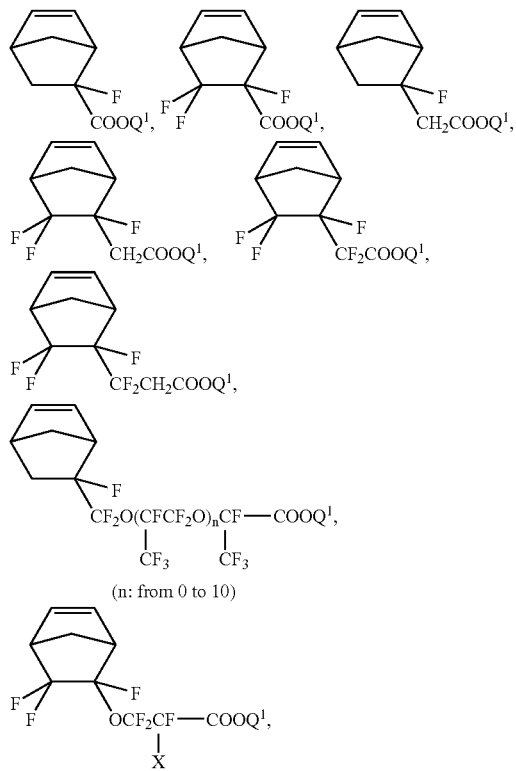

-continued

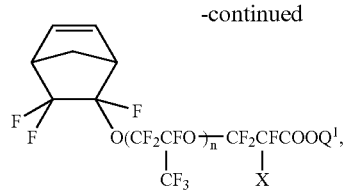

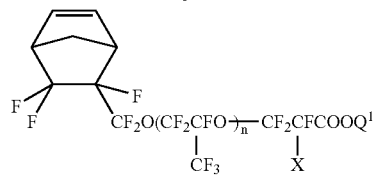

and the like.

Also there are fluorine-containing monomers represented by:

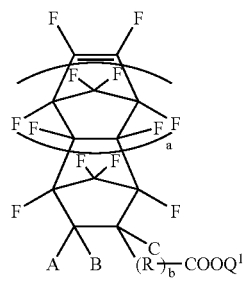

wherein A, B and C are H, F, an alkyl group having 1 to 10 carbon atoms or a fluorine-containing alkyl group having 1 to 10 carbon atoms; R is a divalent hydrocarbon group having 1 to 20 carbon atoms, a fluorine-containing alkylene group having 1 to 20 carbon atoms or a fluorine-containing alkylene group having 2 to 100 carbon atoms and ether bond; a is 0 or an integer of from 1 to 3; b is 0 or 1; —$COOQ^1$ is COOH group or an acid-labile functional group.

Concretely there are monomers having a norbornene backbone such as:

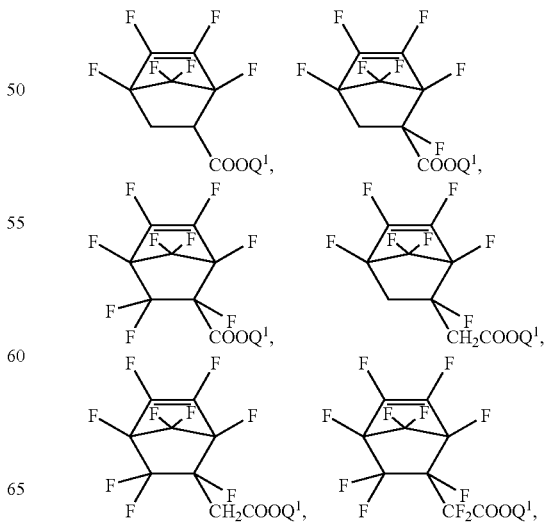

-continued

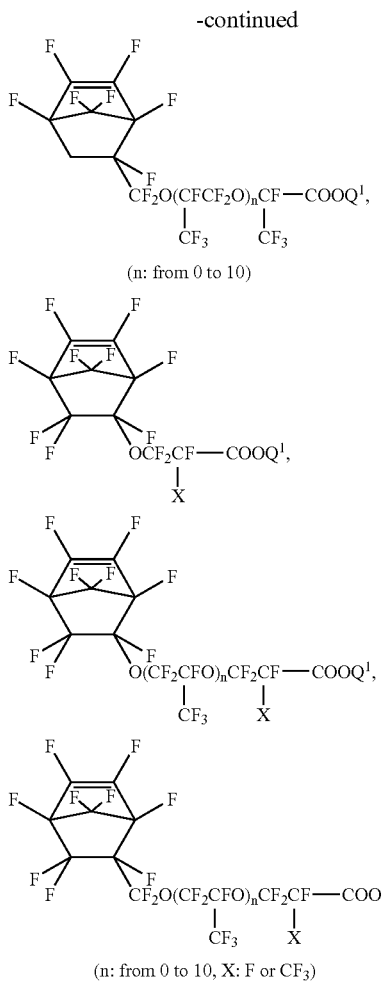

(n: from 0 to 10)

(n: from 0 to 10, X: F or CF$_3$)

and the like
In addition, there are:

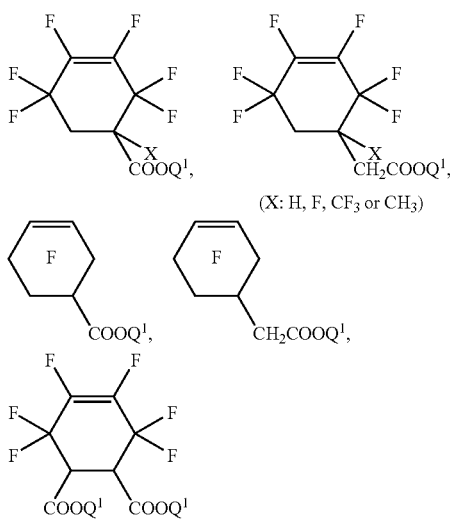

and the like.

In the structural units N1 and N2, $Q^1$ in the acid-labile functional group —COOQ$^1$ is one selected from hydrocarbon groups having tertiary carbon and the structural units are those which can have a structure having the tertiary carbon being bonded directly to carboxyl. For example, there are t-butyl group, 1,1-dimethylpropyl group, adamantyl group, ethyl adamantyl group and the like, and preferred is t-butyl group: —C(CH$_3$)$_3$ from the viewpoint of particularly good acid dissociation reactivity.

In the fluorine-containing polymer of the formula (13), the structural unit M2 comprises a fluorine-containing ethylenic monomer and is preferred from the point that good transparency, particularly enhanced transparency against short wavelength ultraviolet ray (for example, 157 nm) can be imparted to the copolymer.

Examples of the monomer constituting the structural unit M2 are:

$CF_2=CF_2$, $CF_2=CFCl$, $CH_2=CF_2$, $CFH=CH_2$, $CFH=CF_2$, $CF_2=CFCF_3$, $CH_2=CFCF_3$, $CH_2=CHCF_3$ and the like.

Among them, preferred are tetrafluoroethylene ($CF_2=CF_2$) and chlorotrufluoroethylene ($CF_2=CFCl$) from the viewpoint of goof copolymerizability and high effect of imparting transparency.

Examples of the optional structural unit N which does not have an acid-labile or acid-decomposable functional group —OQ$^1$ or —COOQ$^1$ are N3 and N4 mentioned below.

The structural unit N3 comprises a cyclic aliphatic unsaturated hydrocarbon and is selected from those copolymerizable with a fluorine-containing ethylenic monomer constituting the abovementioned M2. The introduction of N3 is preferred from the point that dry etching resistivity in addition to transparency can be enhanced.

It is further preferable from the point that the content of M1 can be adjusted without lowering dry etching resistivity.

Also a part or the whole of hydrogen atoms of the structural unit N3 may be replaced with fluorine atoms, which is preferred because transparency can be imparted more to the polymer.

Examples of the monomer constituting the structural unit N3 are:

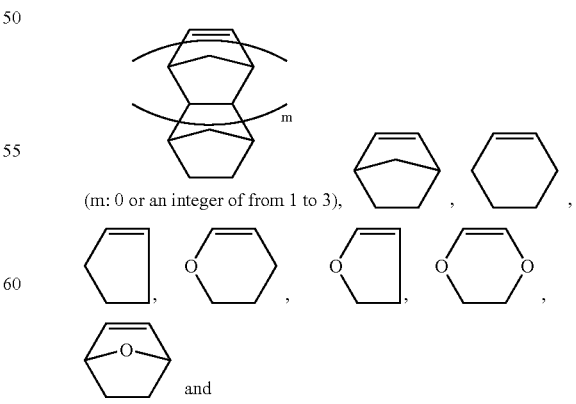

(m: 0 or an integer of from 1 to 3), and fluorine-containing alicyclic monomers of the formula:

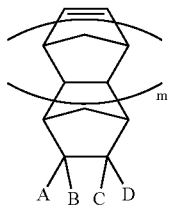

wherein A, B, C and D are H, F, an alkyl group having 1 to 10 carbon atoms or a fluorine-containing alkyl group having 1 to 10 carbon atoms;

m is 0 or an integer of from 1 to 3; any one of A to D has fluorine atom.

There are concretely:

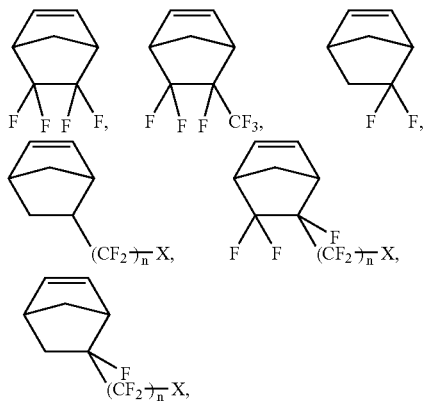

(n: 1 to 10, X: H, F or Cl)

and the like.

In addition, there are:

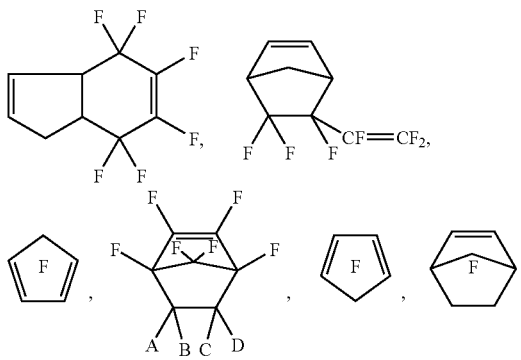

(A, B, C and D are H, F or an alkyl group or fluorine-containing alkyl group having 1 to 10 carbon atoms)

and the like.

Among them, norbornene derivatives are preferred.

The structural unit N4 is selected from those copolymerizable with the monomers constituting the other structural units.

For example, there are:

Acrylic Monomer (Excluding Monomers Giving M2, N1 and N2):

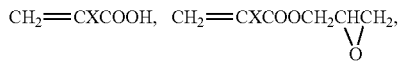

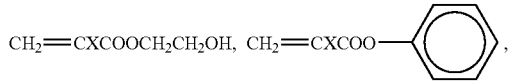

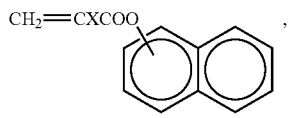

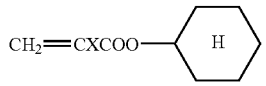

wherein X is selected from H, $CH_3$, F and $CF_3$.

Styrene Monomer:

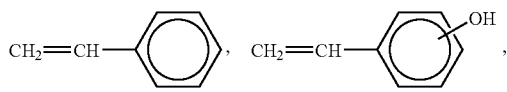

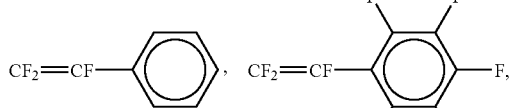

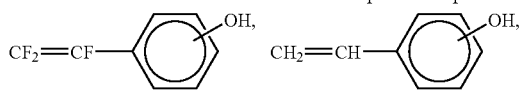

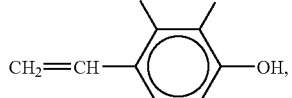

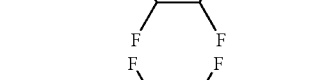

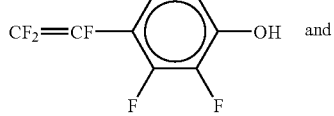

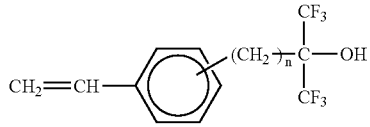

wherein n is 0 or an integer of 1 or 2.

Ethylene Monomer:

$CH_2$=$CH_2$, $CH_2$=$CHCH_3$, $CH_2$=$CHCl$ and the like.

Maleic Acid Monomer:

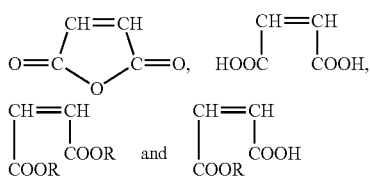

wherein R is a hydrocarbon group having 1 to 20 carbon atoms.

Allyl Monomer:
CH$_2$=CHCH$_2$Cl, CH$_2$=CHCH$_2$OH, CH$_2$=CHCH$_2$COOH, CH$_2$=CHCH$_2$Br and the like.

Allyl Ether Monomer:
CH$_2$=CHCH$_2$OR (R is a hydrocarbon group having 1 to 20 carbon atoms),
CH$_2$=CHCH$_2$OCH(CF$_2$)$_n$X (n: from 1 to 10, X: H, Cl or F),
CH$_2$=CHCH$_2$OCH$_2$CH$_2$COOH,

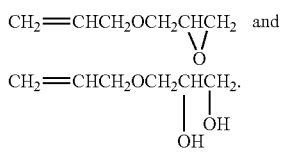

Examples of Other Monomer are:

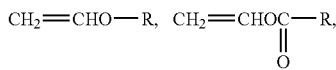

(R is an alkyl group which has 1 to 20 carbon atoms and may be replaced with fluorine.)

More Concretely There Are:

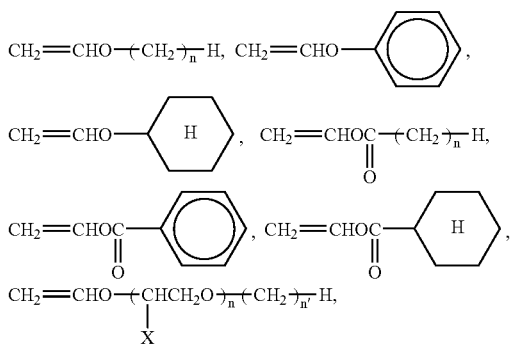

(n: from 1 to 10, n': from 1 to 10, X: H or CH$_3$,)

and the like.

For example, in case of obtaining a polymer having a high Tg or a high melting point for enhancing heat resistance and mechanical properties, it is preferable that the monomer for the optional structural unit N is selected from those having a bulky side chain. For example, the monomer can be preferably selected from:

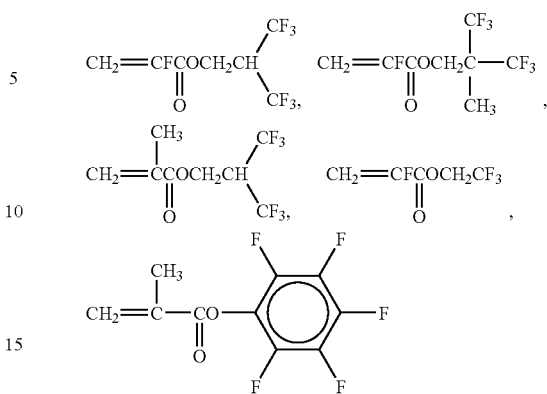

and the like.

Non-limiting examples of the preferred embodiment of the fluorine-containing polymer of the present invention are those mentioned below.

(I) A copolymer of -(M1a)-(M2)- in which the structural unit M2 is a structural unit derived from TFE or CTFE, the structural unit M1 a is a structural unit derived from the norbornene derivative having a fluorine-containing alcohol structure of the formula (15), and the structural units M2 and M1 are contained in amounts of from 30 to 70% by mole, preferably from 40 to 65% by mole and from 30 to 70% by mole, preferably from 35 to 60% by mole, respectively.

This fluorine-containing copolymer is preferred from the viewpoint of high transparency and excellent dry etching resistivity.

Particularly preferred example thereof is a fluorine-containing polymer represented by the formula (14)-2:

wherein the structural unit M2 is a structural unit derived from TFE or CTFE;
the structural unit M1a-1 is a structural unit derived from the norbornene derivatives having a fluorine-containing alcohol structure of the above-mentioned formulae (8) to (12);
the structural unit M1a-2 is a structural unit derived from the norbornene derivatives having a fluorine-containing alcohol structure of the above-mentioned formulae (8) to (12) in which hydroxyl is protected by the protective acid-reactive functional group —OQ$^1$;
the structural unit N is a structural unit derived from monomer copolymerizable with the structural units M1a-1, M1a-2 and M2, provided that (M1a-1)+(M1a-2)+M2 is 100% by mole, a percent by mole ratio of ((M1a-1)+(M1a-2))/M2 is 30/70 to 70/30, and
the structural units M1a-1, M1a-2, M2 and N are contained in amounts of from 1 to 98% by mole, from 1 to 98% by mole, from 1 to 98% by mole and from 0 to 97% by mole, respectively. This polymer is preferred because adhesion to a substrate such as a silicon wafer and wettability to a developing solution are enhanced by OH group in the structural unit M1a-1.

In the formula (14)-2, provided that (M1a-1)+(M1a-2) is 100% by mole, a percent by mole ratio of (M1a-1)/(M1a-2) is optionally selected in the range of 90/10 to 40/60, preferably 90/10 to 50/50, more preferably 85/15 to 60/40. If the proportion of (M1a-1) is too large, the un-exposed portion also becomes soluble and a resist pattern cannot be formed. Even if the un-exposed portion does not become soluble, a thickness of the un-exposed portion is decreased too much and the form of resist pattern becomes round and resolution is lowered. If the proportion of (M1a-1) is too small, there arise problems that since adhesion to undercoating becomes insufficient, the resist is peeled at developing and a developing solution is repelled at developing, which makes it difficult to obtain uniform developing.

(II) A copolymer of -(M1a)-(M2)-(N3)- in which the structural unit M2 is a structural unit derived from TFE or CTFE, the structural unit M1a is a structural unit derived from the norbornene derivative having a fluorine-containing alcohol structure of the formula (15), the structural unit N3 is a structural unit derived from monomer selected from cyclic unsaturated aliphatic hydrocarbon compounds of the above-mentioned structural unit N3, and the structural units M2, M1a and N3 are contained in amounts of from 40 to 60% by mole, from 10 to 45% by mole and from 1 to 50% by mole, respectively.

This fluorine-containing copolymer is preferred since an amount of the functional group contained in the structural unit M1a can be adjusted without lowering dry etching resistivity. Particularly preferred structural unit N3 are those selected from the norbornene derivatives exemplified above.

(III) A copolymer of -(M1a)-(M2)-(N1)- in which the structural unit M2 is a structural unit derived from TFE or CTFE, the structural unit M1a is a structural unit derived from the norbornene derivative having a fluorine-containing alcohol structure of the formula (15), the structural unit N1 is a structural unit derived from monomer selected from ethylenic monomers having COOH group or an acid-labile functional group $COOQ^1$ which is converted to carboxyl due to action of an acid, and the structural units M2, M1a and N1 are contained in amounts of from 10 to 60% by mole, from 1 to 50% by mole and from 5 to 70% by mole, respectively.

This fluorine-containing copolymer is preferred since solubility of the fluorine-containing polymer in a developing solution can be enhanced and a high sensitivity and resolution can be obtained. Especially the preferred structural unit N1 is one having fluorine atom. Concretely among the compounds exemplified above, preferred more are the structural units derived from monomers having the functional group $COOQ^1$ such as fluorine-containing acrylic monomers, fluorine-containing allyl monomers, fluorine-containing styrene monomers and the above-mentioned monomers N1-1 and N1-2 having a fluoroalkyl group in a side chain thereof, since transparency can be further enhanced.

(IV) A fluorine-containing polymer represented by:

-(M1a-3)-(M2)-(N2)-(N)-   (14)-3

wherein the structural unit M2 is as defined in the formula (13), the structural unit M1a-3 is a structural unit derived from at least one selected from the norbornene derivatives represented by the formulae (5) to (12) and the fluorine-containing norbornene derivatives which are represented by the formulae (5) to (12) and have a protective acid-reactive functional group $-OQ^1$ protecting hydroxyl thereof, the structural unit N2 is a structural unit derived from a cyclic unsaturated aliphatic hydrocarbon compound which is copolymerizable with monomers constituting the structural units M1a-3, M2 and N and further has COOH group or an acid-labile functional group $-COOQ^1$ which can be converted to carboxyl due to action of an acid, the structural unit N is a structural unit derived from monomer copolymerizable with monomers constituting the structural units M1a-3, M2 and N2, provided that (M1a-3)+M2+N2 is 100% by mole, a percent by mole ratio of ((M1a-3)+N2)/M2 is 70/30 to 30/70, and the structural units M1a-3, M2, N2 and N are contained in amounts of from 1 to 98% by mole, from 1 to 98% by mole, from 1 to 98% by mole and from 0 to 97% by mole, respectively.

This fluorine-containing copolymer is preferred since solubility of the fluorine-containing polymer in a developing solution can be enhanced, a high sensitivity and resolution can be obtained and further dry etching resistivity can be enhanced. It is particularly preferable that the structural unit N2 is a structural unit derived from norbornene derivatives having COOH group or an acid-labile group $-COOQ^1$ converted to carboxyl due to action of an acid, and further preferred are norbornene derivatives having fluorine atom or a fluorine-containing alkyl group. Concretely preferred are structural units derived from norbornene derivatives represented by the formula:

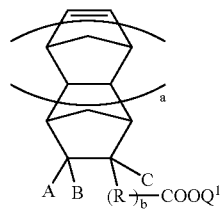

wherein A, B and C are H, F, an alkyl group having 1 to 10 carbon atoms or a fluorine-containing alkyl group having 1 to 10 carbon atoms; R is a divalent hydrocarbon having 1 to 20 carbon atoms, a fluorine-containing alkylene group having 1 to 20 carbon atoms or a fluorine-containing alkylene group having 2 to 100 carbon atoms and ether bond; a is 0 or an integer of from 1 to 3; b is 0 or 1; $-COOQ^1$ is COOH group or an acid-labile functional group which can be converted to carboxyl by an acid; when b is 0 or R does not have fluorine atom, any one of A to C is fluorine atom or a fluorine-containing alkyl group, since transparency can be further enhanced.

Among them, preferred examples are fluorine-containing polymers represented by the formula (14)-4:

-(M1a-1)-(M2)-(N2-1)-(N)-   (14)-4

wherein the structural unit M1a-1 and M2 are as defined in the formula (14)-2, the structural unit N2-1 is a structural unit derived from norbornene derivatives represented by the formula (3)-1:

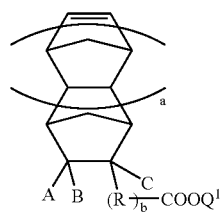

wherein —COOQ$^1$ is an acid-labile functional group which can be converted to carboxyl by an acid, A, B, C, R, a and b are as defined above, the structural unit N is a structural unit derived from monomer copolymerizable with monomers constituting the structural units M1a-1, M2 and N2-1, provided that (M1a-1)+(M2)+(N2-1) is 100% by mole, a percent by mole ratio of ((M1a-1)+(N2-1))/(M2) is 70/30 to 30/70, and the structural units M1a-1, M2, N2-1 and N are contained in amounts of from 1 to 98% by mole, from 1 to 98% by mole, from 1 to 98% by mole and from 0 to 97% by mole, respectively.

Those polymers are preferred since a fine resist pattern having a high resolution can be formed in F2 lithography while maintaining a high sensitivity.

In the fluorine-containing polymer of the formula (14)-4, the proportion of (M1a-1)/(N2-1) is optionally selected within a range of 95/5 to 40/60% by mole, preferably 95/5 to 50/50% by mole, more preferably 90/10 to 50/50% by mole, further preferably 85/15 to 60/40% by mole.

If the proportion of (M1a-1) is too large, an un-exposed portion also becomes soluble and a resist pattern cannot be formed. Even if the un-exposed portion does not become soluble, a thickness of the un-exposed portion is decreased, a form of the resist pattern becomes round and resolution is lowered. If the proportion of (M1a-1) is too small, there arises a problem that since adhesion to undercoating becomes insufficient, peeling occurs at developing and a developing solution is repelled at developing, which makes it difficult to obtain uniform developing. Further if the proportion of (N2-1) is too small, swelling of the un-exposed portion easily occurs, inflation of a pattern form occurs and a residue of the resist polymer (un-dissolved portion) is apt to arise at an exposed portion, which are not preferred.

In the fluorine-containing copolymers of the formulae (14) and (14)-1 to (14)-4 of the present invention, it is necessary that the OH-containing copolymer obtained after the dissociation reaction by an acid or the fluorine-containing copolymer having both of OH group and COOH group has sufficient solubility in a developing solution. A content of acid-labile functional group necessary therefor (a total of a functional group converted to OH group by an acid and a COOH group when the both are present like the above-mentioned fluorine-containing polymers III or IV) varies depending on components (kinds of monomers) and molecular weight of the polymer. The content is preferably not less than 20% by mole, further not less than 30% by mole, more preferably not less than 40% by mole based on the whole structural units constituting the fluorine-containing copolymer.

As a result of studies on a resist composition prepared from a fluorine-containing polymer having an acid-labile functional group and studies on a resist pattern formation using the composition, the present inventors have found problems with poor adhesion of the fluorine-containing polymer to a silicon wafer substrate and occurrence of peeling of a resist at developing and cracking of a fine resist pattern.

Further there was found a problem that due to a high water repellency of a surface of a resist film, a developing solution was repelled at puddle-developing and did not extend over the resist film and thus uniform developing could not be obtained.

The present inventors have made intensive studies to solve those problems and have found that the above-mentioned two problems could be solved by dissociating a part of the acid-labile functional groups in the fluorine-containing copolymer of the present invention to OH groups (or dissociating into at least either of OH groups or COOH groups when COOH groups are present together with the groups converted to OH groups by an acid). Namely, it was found that when the fluorine-containing copolymer partly subjected to dissociation (or partly subjected to deprotection) is used, adhesion to the substrate is improved and repelling of the developing solution is improved, which makes it possible to obtain uniform developing.

In the fluorine-containing copolymer of the present invention, the proportion of OH group (or OH group and COOH group when COOH group is present together) being present by the dissociation (deprotection) of the acid-labile functional group varies depending on kind, components, etc. of the copolymer. It is preferable that OH group (or a total of OH group and COOH group when COOH group is present together) after the dissociation is present within a range of not less than 1.0% by mole and less than 15% by mole, more preferably from 1 to 10% by mole, further preferably from 2 to 5% by mole based on the whole structural units constituting the fluorine-containing copolymer. If the dissociation ratio (deprotection ratio) becomes too high and the content of OH group (or a total of OH group and COOH group when COOH group is present together) is too high, an un-exposed portion also becomes soluble at developing and a resist pattern cannot be formed.

If the dissociation ratio (deprotection ratio) becomes too low and the content of OH group (or a total of OH group and COOH group when COOH group is present together) is too low, an effect of exhibiting adhesion to a substrate and uniformity of developing becomes insufficient.

The molecular weight of the fluorine-containing polymer of the formulae (14) and (14)-1 to (14)-4 can be selected within a range of from 1,000 to 1,000,000 in a number average molecular weight depending on application, object and a form thereof in use, and is in a range of preferably from 3,000 to 700,000, more preferably from about 5,000 to about 500,000. If the molecular weight is too low, heat resistance and mechanical properties of the polymer coating film easily become insufficient, and if the molecular weight is too high, it is disadvantageous from the viewpoint of processability. Particularly when the polymer is used in the form of a coating material to form a thin coating film, a too high molecular weight becomes disadvantageous in forming a film. The molecular weight is preferably not more than 300,000, particularly preferably not more than 200,000.

Any of the fluorine-containing polymers having an acid-reactive group of the formulae (14) and (14)-1 to (14)-4 of the present invention are characterized by having an acid-reactive functional group (—OH, —COOH, —OQ$^1$, —COOQ$^1$). For introducing those functional groups to the fluorine-containing polymers, various methods can be used, and generally there can be used:

(i) a method of previously synthesizing a monomer having the above-mentioned functional group and then polymerizing the monomer, (ii) a method of synthesizing a polymer having other functional group and converting the above-mentioned functional group by high molecular reaction, thus introducing the functional group to the polymer, and the like method.

In the method (i), the fluorine-containing polymer can be obtained by (co)polymerizing, through known method, monomers corresponding to each structural unit, that is, the fluorine-containing norbornene monomer (M1a or the like) having functional group (—OH, —COOH, —OQ$^1$, —COOQ$^1$), the fluorine-containing ethylenic monomer (M2) and the monomer for the optional structural unit (N) when used as case demands. For the polymerization, radical polymerization method, anion polymerization method, cation polymerization method and the like can be employed. Among them, the radical polymerization method is preferably used since each monomer for obtaining the fluorine-containing polymer of the present invention has good radial polymerizability, control of composition and molecular weight is easy and production in an industrial scale is easy. Namely, in order to initiate the polymerization, means for initiation is not limited particularly as far as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like. The molecular weight is controlled by the contents of monomers to be used for the polymerization, the content of polymerization initiator, the content of chain transfer agent, temperature, etc. The components of the produced copolymer can be controlled by the starting monomer components.

Examples of the method (ii) of introducing an acid-labile or acid-decomposable functional group are a method of preparing a polymer having no functional group —$OQ^1$ or —$COOQ^1$ of the formula (14) or (14)-1 to (14)-4 in the same manner as in the method (i) and then reacting the OH group of the structural unit M1a or carboxyl of the structural unit N with vinyl ether such as ethyl vinyl ether or dihydropyran in the presence of an acid such as toluenesulfonic acid to introduce an acid-decomposable functional group (ketals); a method of reacting the fluorine-containing polymer having 1,2-diol with ketone to obtain an acid-decomposable functional group (cyclic acetal compound); and the like method.

The functional group $Q^2$ undergoing condensation reaction by an acid is concretely a functional group which causes self-condensation or poly-condensation due to action of an acid or cation or condensation reaction or poly-condensation reaction with a crosslinking agent due to action of an acid in the presence of the crosslinking agent, or a functional group which causes a change in polarity by rearrangement by an acid or cation (for example, pinacol rearrangement or carbinol rearrangement). Preferred is a functional group selected from —OH, —COOH, —CN, —$SO_3H$, epoxy group and the like.

The fluorine-containing polymer having the functional group $Q^2$ undergoing condensation reaction by an acid is used for a negative type photoresist. The functional group undergoing condensation reaction by an acid causes condensation or poly-condensation reaction or rearrangement reaction by an acid generated from the photoacid generator (B) by irradiation of energy rays, resulting in occurrence of self-crosslinking reaction, rearrangement reaction in a molecule and crosslinking reaction with a crosslinking agent in the composition containing the crosslinking agent. Thus the functional group has a function of making the fluorine-containing polymer (A) in-soluble or less-soluble in a developing solution (alkali or solvent) though the polymer before the reaction is soluble therein.

Further the functional group of the present invention undergoing condensation reaction is preferably one (for example, —COOH, —$SO_3H$, —OH, etc.) which can impart a function of making the polymer soluble in a developing solution such as alkali or a solvent before the reaction with an acid and may be one (—CN, epoxy, etc.) having only a function of making the polymer in-soluble in a developing solution by condensation reaction (crosslinking reaction) by an acid. In that case, the polymer can be used as a negative type photoresist by using the functional group in combination of other functional group having a function of making the polymer soluble in a developing solution or by making a backbone structure of the fluorine-containing polymer soluble in a developing solution In the fluorine-containing polymer (A) used for the chemically amplifying type resist composition of the present invention, when a norbornene derivative having a fluorine-containing alcohol structure is used as the structural unit M1a, the resist composition can be used as the above-mentioned negative type photoresist in combination of a crosslinking agent.

In that case, examples of preferred norbornene derivative are the same as those raised in the above-mentioned formulae (8) to (12).

The fluorine-containing polymer of the present invention having a norbornene backbone having a fluorine-containing alcohol structure is useful as a negative type photoresist because the polymer itself has a high solubility in an aqueous alkaline solution (developing solution for resist).

The fluorine-containing polymer can also be used as a negative type photoresist by introducing, to the structural unit N, the above-mentioned functional group $Q^2$ undergoing condensation reaction by an acid.

In the chemically amplifying type resist composition of the present invention, the photoacid generator (B) is a compound which generates an acid or cation by irradiating the compound itself or the resist composition containing the compound with radiation. The compounds can be used in a mixture of two or more thereof.

Examples of the photoacid generator (B) are, for instance, known compounds such as an organic halogen compound, sulfonic acid ester, onium salt, diazonium salt, disulfone compound and a mixture thereof.

Examples thereof are, for instance, haloalkyl group-containing s-triazine derivatives such as tris(trichloromethyl)-s-triazine, tris(tribromomethyl)-s-triazine, tris(dibromomethyl)-s-triazine and 2,4-bis(tribromomethyl)-6-p-methoxyphenyl-s-triazine, halogen-substituted paraffin hydrocarbons such as 1,2,3,4-tetrabromobutane, 1,1,2,2-tetrabromoethane, carbon tetrabromide and iodoform, halogen-substituted cycloparaffin hydrocarbons such as hexabromocyclohexane, hexachlorocyclohexane and hexabromocyclododecane, haloalkyl group-containing benzene derivatives such as bis(trichloromethyl)benzene and bis(tribromomethyl)benzene, haloalkyl group-containing sulfone compounds such as tribromomethylphenyl sulfone and trichloromethylphenyl sulfone, halogen-containing sulfolane compounds such as 2,3-dibromosulfolane, haloalkyl group-containing isocyanurates such as tris(2,3-dibromopropyl)isocyanurate, sulfonium salts such as triphenylsulfonium chloride, triphenylsulfoniummethane sulfonate, triphenylsulfoniumtrifluoromethane sulfonate, triphenylsulfonium-p-toluene sulfonate, triphenylsulfoniumtetrafluoro borate, triphenylsulfoniumhexafluoro arcenate and triphenylsulfoniumhexafluoro phosphonate, iodonium salts such as diphenyl-iodonium-trifluoromethane-sulfonate, diphenyl-iodonium-p-toluene-sulfonate, diphenyliodonium tetrafluoroborate, diphenyliodonium hexafluoroarcenate and diphenyliodonium hexafluorophosphonate, sulfonic acid esters such as methyl p-toluenesulfonate, ethyl p-toluenesulfonate, butyl p-toluenesulfonate, phenyl p-toluenesulfonate, 1,2,3-tris(p-toluenesulfonyloxy)benzene, p-toluenesulfonic acid benzoyl ester, methyl methanesulfonate, ethyl methanesulfonate, butyl methanesulfonate, 1,2,3-tris(methanesulfonyloxy)benzene, phenyl methanesulfonate, methane sulfonic acid benzoin ester, methyl trifluoromethanesulfonate, ethyl trifluoromethanesulfonate, butyl trifluoromethanesulfonate, 1,2,3-tris(trifluoromethanesulfonyloxy)benzene, phenyl trifluoromethanesulfonate and benzoin trifluoromethanesulfonate, disulfones such as diphenyldisulfone, sulfonediazides such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomehtane, cyclopentylsulfonyl-(2-methoxyphenylsulfonyl)diazomethane, cyclopentylsulfonyl-(3-methoxyphenylsulfonyl) diazomethane, cyclopentylsulfonyl- (4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl) diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl)diazomethane, cyclopentylsulfonyl-(3-chlorophenylsulfonyl) diazomethane, cyclopentylsulfonyl-(4-chlorophenylsulfonyl)diazomethane, cyclohexylsulfonyl-(2-trifluoromethyphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl) diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-triethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl- (2,3,4-triethylphenylsulfonyl)diazomethane, phenylsulfonyl-(2-methoxylphenylsulfonyl)diazomethane, phenylsulfonyl-(3-methoxylphenylsulfonyl)diazomethane, phenylsulfonyl-(4-methoxylphenylsulfonyl)diazomethane, bis(2-methoxylphenylsulfonyl)diazomethane, bis(3-methoxylphenylsulfonyl)diazomethane, bis(4-methoxylphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl) diazomethane, phenylsulfonyl-(2,3,4-triethylphenylsulfonyl)diazomethane, 2,4-dimethylphenylsulfonyl-(2,4,6-trimethylphenylsulfonyl)diazomethane, 2,4-dimethylphenylsulfonyl-(2,3,4-trimethylphenylsulfonyl) diazomethane, phenylsulfonyl-(2-fluorophenylsulfonyl) diazomethane, phenylsulfonyl-(3-fluorophenylsulfonyl) diazomethane and phenylsulfonyl-(4-fluorophenylsulfonyl) diazomethane, o-nitrobenzyl esters such as o-nitrobenzyl-p-toluenesulfonate, sulfone hydrazides such as N,N'-di(phenylsulfonyl)hydrazide and the like.

Examples of the preferable photoacid generator are compounds generating any of sulfonic acid, sulfenic acid or sulfinic acid. Examples thereof are onium sulfonates such as triphenylsulfonium-p-toluenesulfonate and diphenyliodonium-p-toluenesulfonate, sulfonic acid esters such as phenyl p-toluenesulfonate and 1,2,3-tris(p-toluenesulfonyloxy)benzene, disulfones such as diphenyldisulfone, sulfonediazides such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomehtane, cyclopentylsulfonyl-(2-methoxyphenylsulfonyl)diazomethane, cyclopentylsulfonyl-(3-methoxyphenylsulfonyl) diazomethane, cyclopentylsulfonyl-(4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl)diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl) diazomethane, cyclopentylsulfonyl-(3-chlorophenylsulfonyl) diazomethane, cyclopentylsulfonyl-(4-chlorophenylsulfonyl)diazomethane, cyclohexylsulfonyl-(2-trifluoromethylphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl) diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-triethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl-(2,3,4-triethylphenylsulfonyl)diazomethane, phenylsulfonyl-(2-methoxylphenylsulfonyl)diazomethane, phenylsulfonyl-(3-methoxylphenylsulfonyl)diazomethane, phenylsulfonyl-(4-methoxylphenylsulfonyl)diazomethane, bis(2-methoxylphenylsulfonyl)diazomethane, bis(3-methoxylphenylsulfonyl)diazomethane, bis(4-methoxylphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl)diazomethane, phenylsulfonyl-(2,3,4-triethylphenylsulfonyl)diazomethane, 2,4-dimethylphenylsulfonyl-(2,4,6-trimethylphenylsulfonyl)diazomethane, 2,4-dimethylphenylsulfonyl-(2,3,4-trimethylphenylsulfonyl)diazomethane, phenylsulfonyl-(2-fluorophenylsulfonyl)diazomethane, phenylsulfonyl-(3-fluorophenylsulfonyl)diazomethane and phenylsulfonyl-(4-fluorophenylsulfonyl)diazomethane, o-nitrobenzyl esters such as nitrobenzyl-p-toluenesulfonate, and the like. Particularly sulfonediazides are preferable.

Further in addition to the above-mentioned examples, a photoacid generator of onium salts having fluorine atom can be used. For example, there are preferably used a fluoroalkyl onium salt represented by the formula:

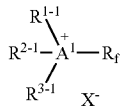

wherein $A^1$ is an element selected from iodine, sulfur, selenium, tellurium, nitrogen and phosphorus;

when $A^1$ is iodine, $R^{2-1}$ and $R^{3-1}$ are not present and $R^{1-1}$ is an alkyl group having 1 to 15 carbon atoms or an aryl group having 6 to 15 carbon atoms;

when $A^1$ is sulfur, selenium or tellurium, $R^{3-1}$ is not present and $R^{1-1}$ and $R^2$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms and $R^{1-1}$ and $R^{2-1}$ may be bonded to each other to form a ring;

when $A^1$ is nitrogen or phosphorus, $R^{1-1}$, $R^{2-1}$ and $R^{3-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms and $R^{1-1}$, $R^{2-1}$ and $R^{3-1}$ may be bonded to each other to form one or more rings, or $R^{3-1}$ may not be present and $R^{1-1}$ and $R^{2-1}$ may be bonded to each other to form an aromatic ring including $A^1$;

the above-mentioned alkyl group, an alkyl group of the dialkylamino group and an alkyl group of the alkylarylamino group may be substituted with an aryl group, halogen atom, oxygen atom, nitrogen atom, sulfur atom or silicon atom, may be branched or may form a ring, and the above-mentioned aryl group, an aryl group of the alkylarylamino group and an aryl group of the diarylamino group may be substituted with an alkyl group, haloalkyl group, halogen atom, alkoxyl group, aryloxy group, nitro group, amide group, cyano group, alkanoyl group, aroyl group, alkoxycarbonyl group, aryloxycarbonyl group or acyloxy group;

$R_f$ is a perfluoroalkyl group having 1 to 15 carbon atoms which may be branched or may form a ring, or is the perfluoroalkyl group in which a part of its fluorine atoms is substituted with hydrogen atoms; $X^-$ is a conjugated base of Brønsted acid, or a fluoroalkyl onium salt represented by the formula:

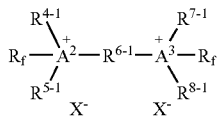

wherein $A^2$ and $A^3$ are the same or different and each is an element selected from iodine, sulfur, selenium, tellurium, nitrogen and phosphorus;

when $A^2$ or $A^3$ is iodine, $R^{4-1}$, $R^{5-1}$, $R^{7-1}$ and $R^{8-1}$ are not present;

when $A^2$ or $A^3$ is sulfur, selenium or tellurium, $R^{5-1}$ and $R^{8-1}$ are not present and $R^{4-1}$ and $R^{7-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms;

when $A^2$ or $A^3$ is nitrogen or phosphorus, $R^{4-1}$, $R^{5-1}$, $R^{7-1}$ and $R^{8-1}$ are independently an alkyl group having 1 to 15 carbon atoms, an aryl group having 6 to 20 carbon atoms, a dialkylamino group having 2 to 30 carbon atoms, an alkylarylamino group having 7 to 35 carbon atoms or a diarylamino group having 12 to 40 carbon atoms, and $R^{4-1}$ and $R^{5-1}$ or $R^{7-1}$ and $R^{8-1}$ may be bonded to each other, respectively to form a ring;

the above-mentioned alkyl group, an alkyl group of the dialkylamino group and an alkyl group of the alkylarylamino group may be substituted with an aryl group, halogen atom, oxygen atom, nitrogen atom, sulfur atom or silicon atom, may be branched or may form a ring, and the above-mentioned aryl group, an aryl group of the alkylarylamino group and an aryl group of the diarylamino group may be substituted with an alkyl group, haloalkyl group, halogen atom, alkoxyl group, aryloxy group, nitro group, amide group, cyano group, alkanoyl group, aroyl group, alkoxycarbonyl group, aryloxycarbonyl group or acyloxy group;

$R^{6-1}$ is an alkylene group having 1 to 15 carbon atoms which may be substituted with an aryl group, halogen atom, oxygen atom, nitrogen atom, sulfur atom or silicon atom, may be branched or may form a ring; $R_f$ is a perfluoroalkyl group having 1 to 15 carbon atoms which may be branched or may form a ring, or is the perfluoroalkyl group in which a part of its fluorine atoms is substituted with hydrogen atoms; $X^-$ is a conjugated base of Brønsted acid and the like.

Examples thereof are fluoroalkyl onium salts having iodine atom as its center element:

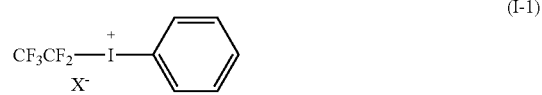

(I-1)

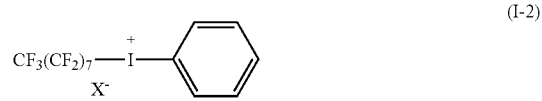

(I-2)

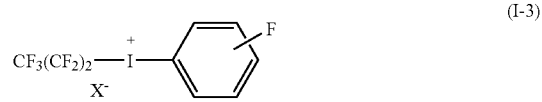

(I-3)

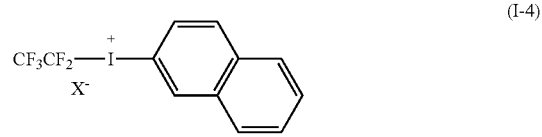

(I-4)

-continued
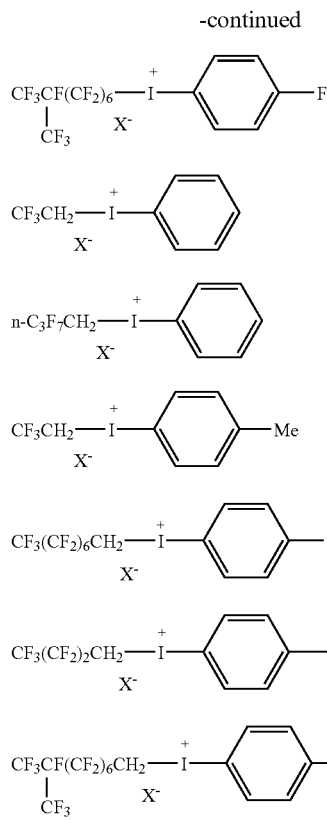
Fluoroalkyl onium salt having sulfur atom as its center element:
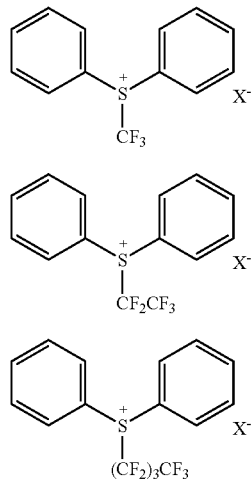
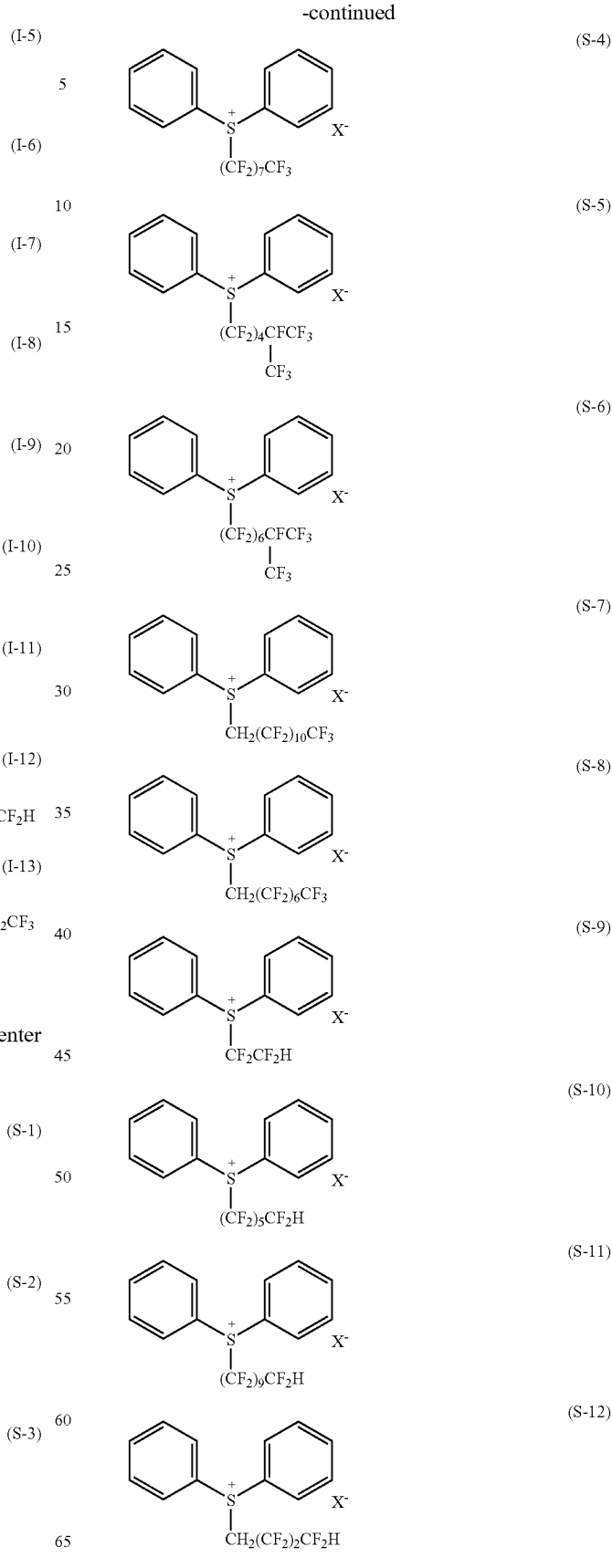

-continued
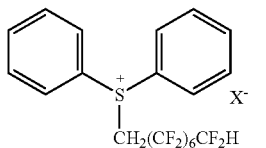 (S-13)
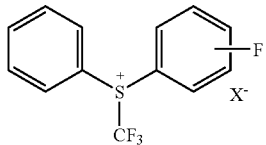 (S-14)
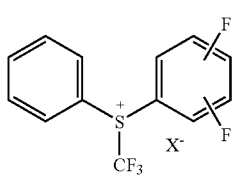 (S-15)
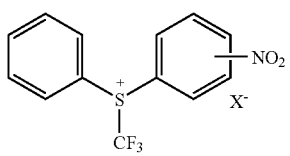 (S-16)
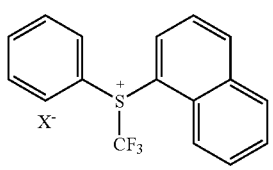 (S-17)
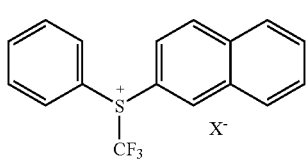 (S-18)
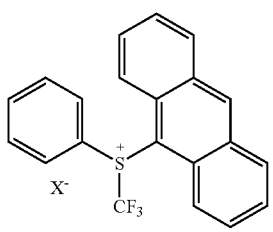 (S-19)
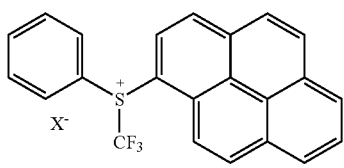 (S-20)
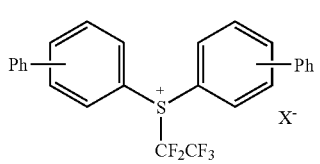 (S-21)
-continued
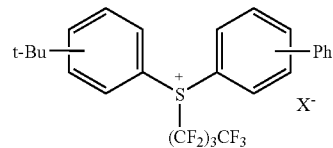 (S-22)
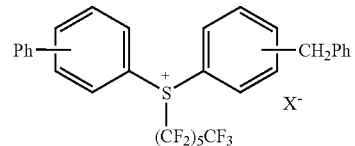 (S-23)
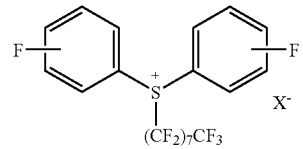 (S-24)
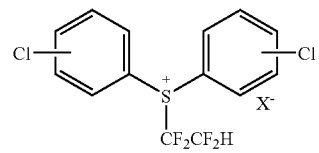 (S-25)
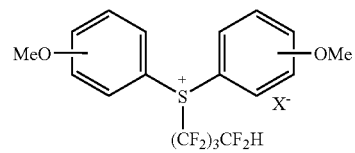 (S-26)
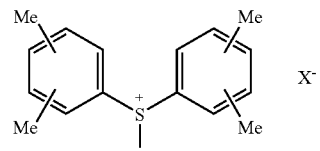 (S-27)
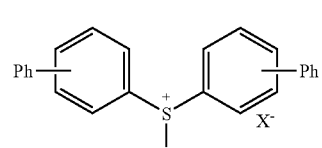 (S-28)
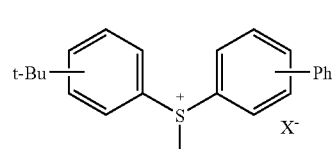 (S-29)
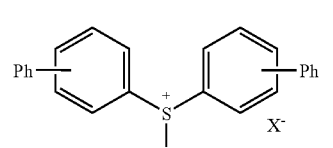 (S-30)
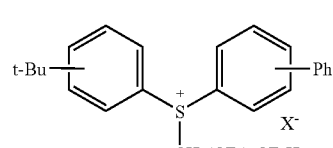 (S-31)

-continued
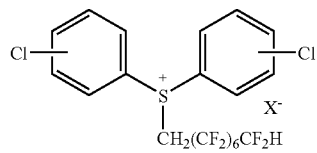 (S-32)
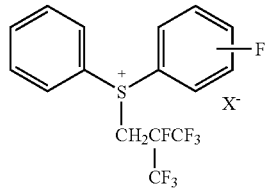 (S-33)
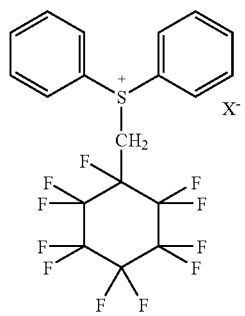 (S-34)
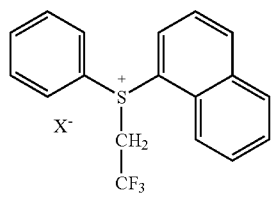 (S-35)
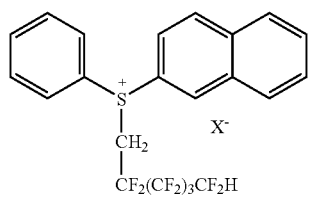 (S-36)
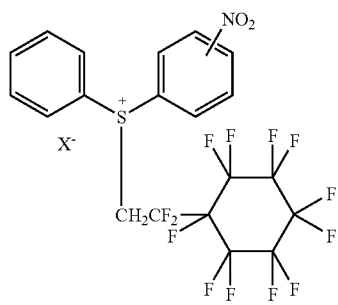 (S-37)
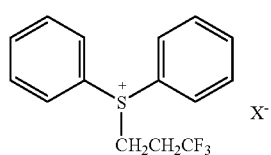 (S-38)
-continued
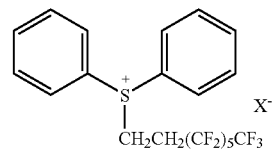 (S-39)
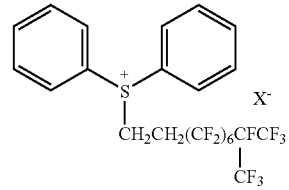 (S-40)
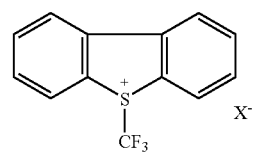 (S-41)
(S-42)
(S-43)
(S-44)
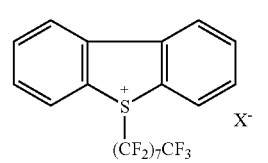 (S-45)
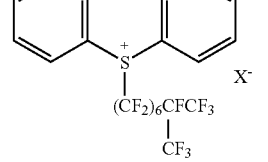 (S-46)
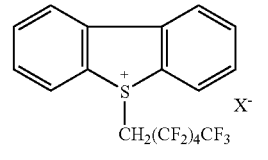 
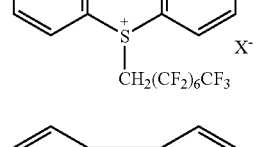 (S-47)

-continued
(S-48)
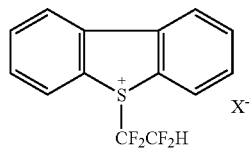
(S-49)
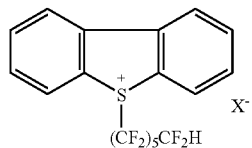
(S-50)
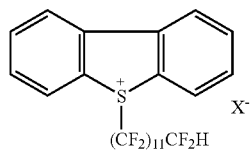
(S-51)
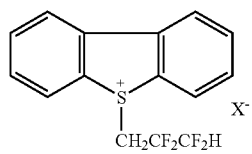
(S-52)
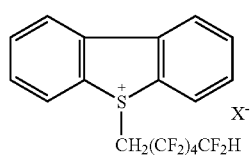
(S-53)
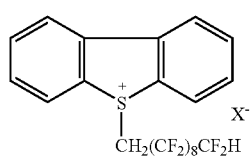
(S-54)
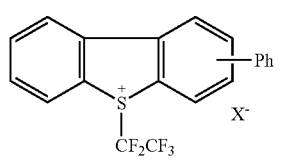
(S-55)
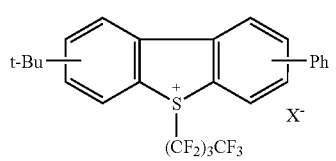
(S-56)
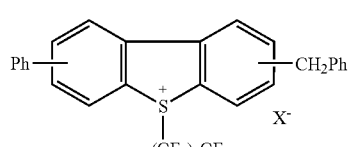
(S-57)
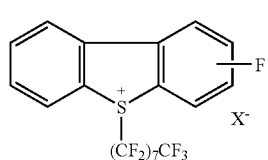
-continued
(S-58)
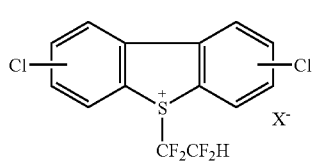
(S-59)
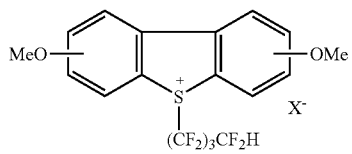
(S-60)
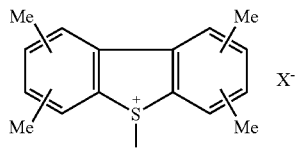
(S-61)
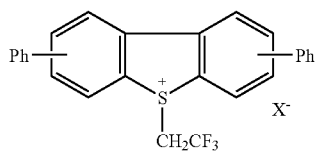
(S-62)
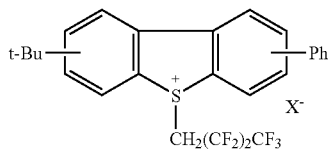
(S-63)
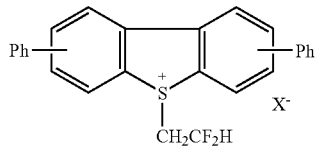
(S-64)
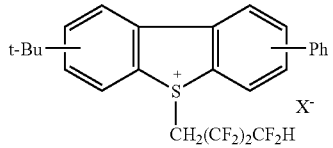
(S-65)
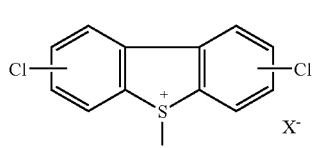
(S-66)
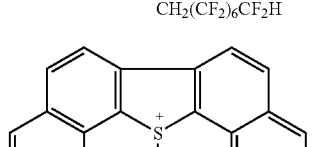
(S-67)
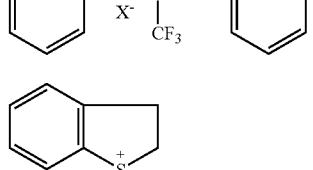

-continued
(S-68) 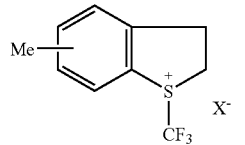
(S-69) 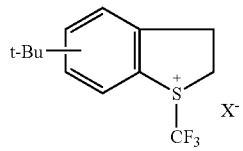
(S-70) 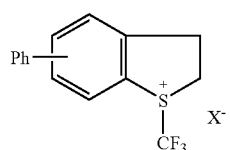
(S-71) 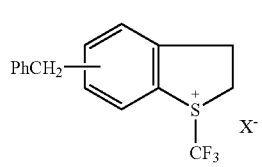
(S-72) 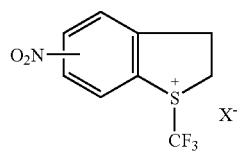
(S-73) 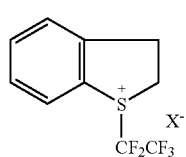
(S-74) 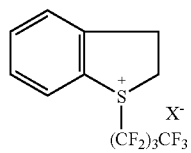
(S-75) 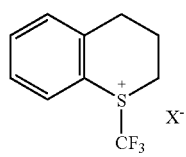
(S-76) 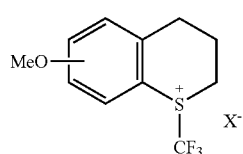
(S-77) 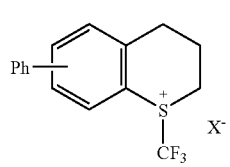
-continued
(S-78) 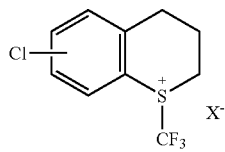
(S-79) 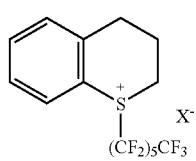
(S-80) 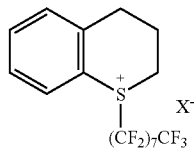
(S-81) 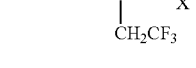
(S-82) 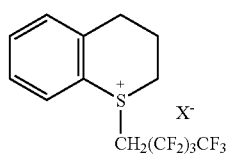
(S-83) 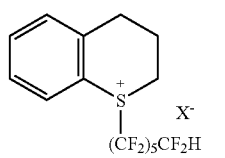
(S-84) 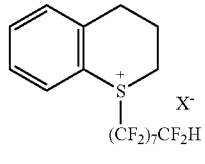
(S-85) 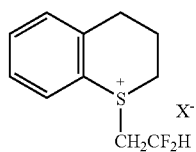
(S-86) 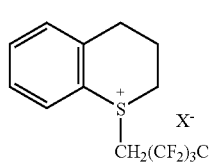

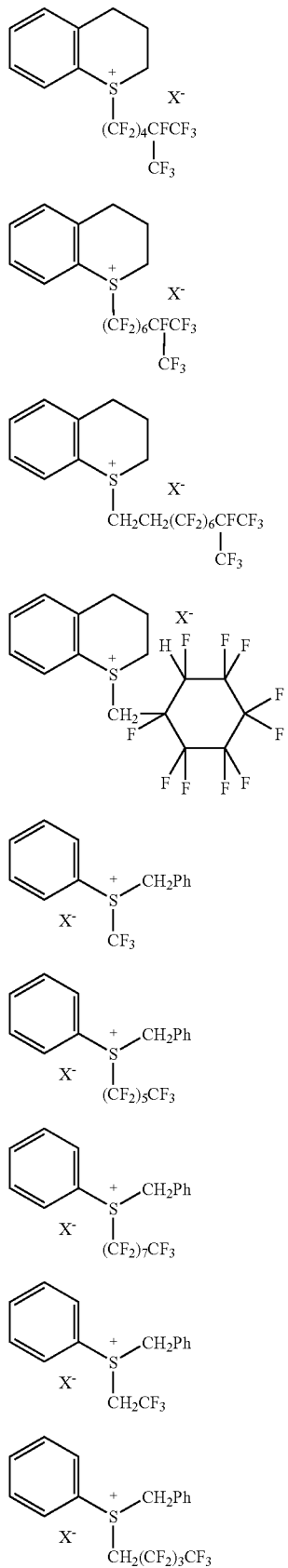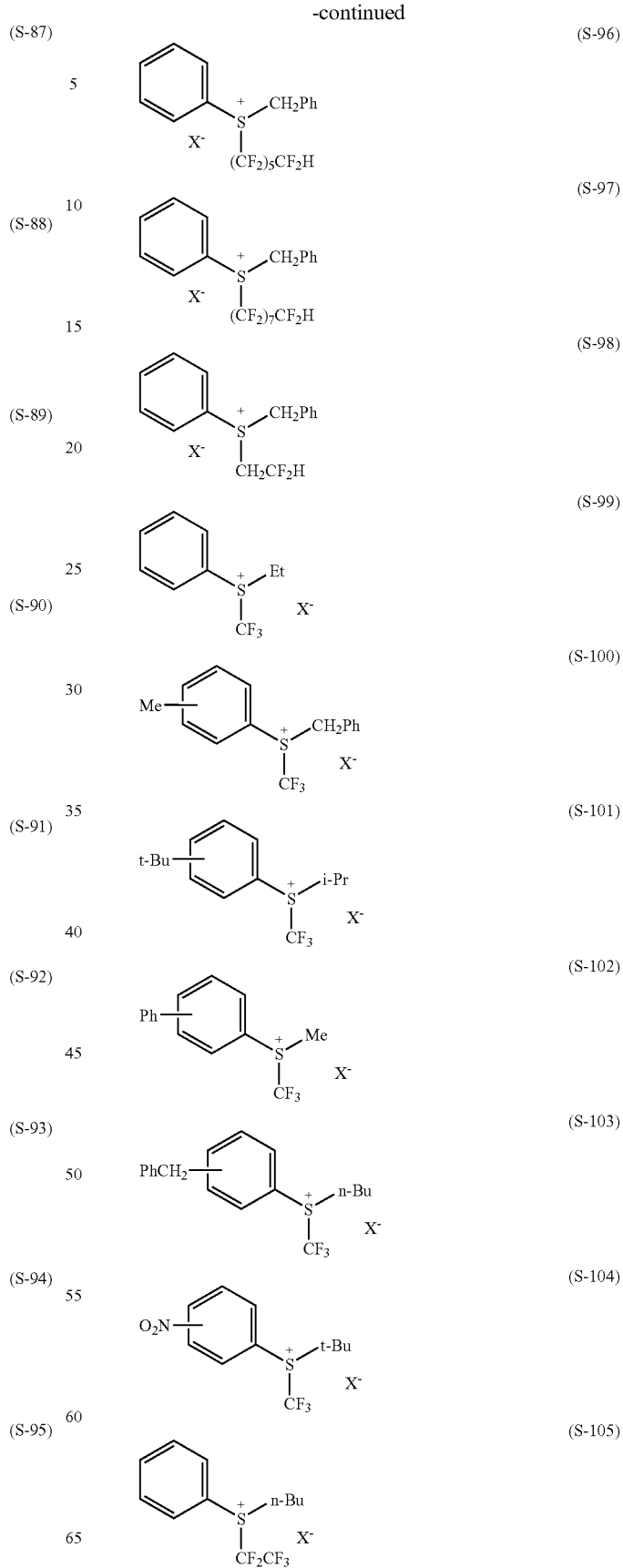

-continued
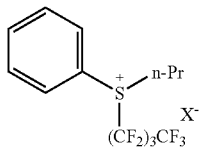 (S-106)
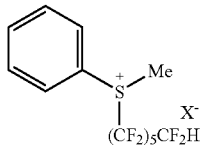 (S-107)
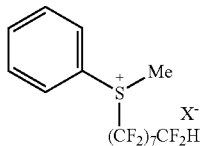 (S-108)
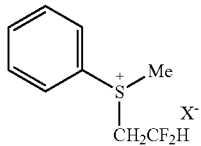 (S-109)
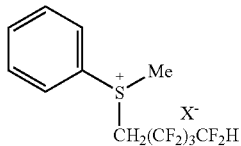 (S-110)
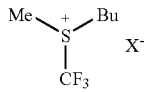 (S-111)
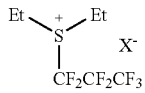 (S-112)
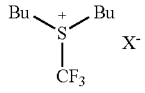 (S-113)
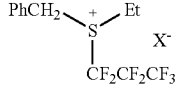 (S-114)
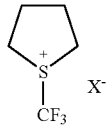 (S-115)
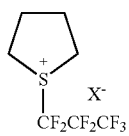 (S-116)
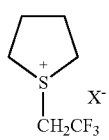 (S-117)
-continued
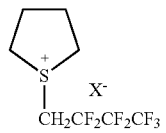 (S-118)
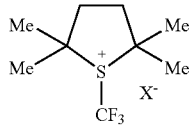 (S-119)
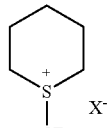 (S-120)
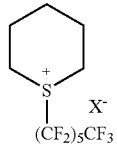 (S-121)
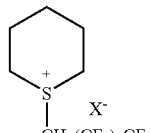 (S-122)
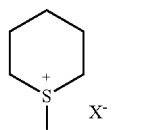 (S-123)
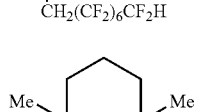 (S-124)
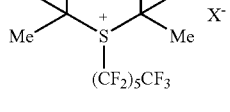 (S-125)
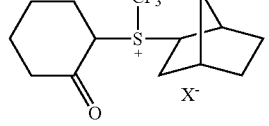 (S-126)
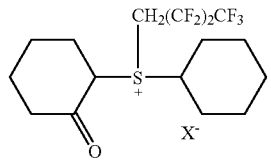 (S-127)

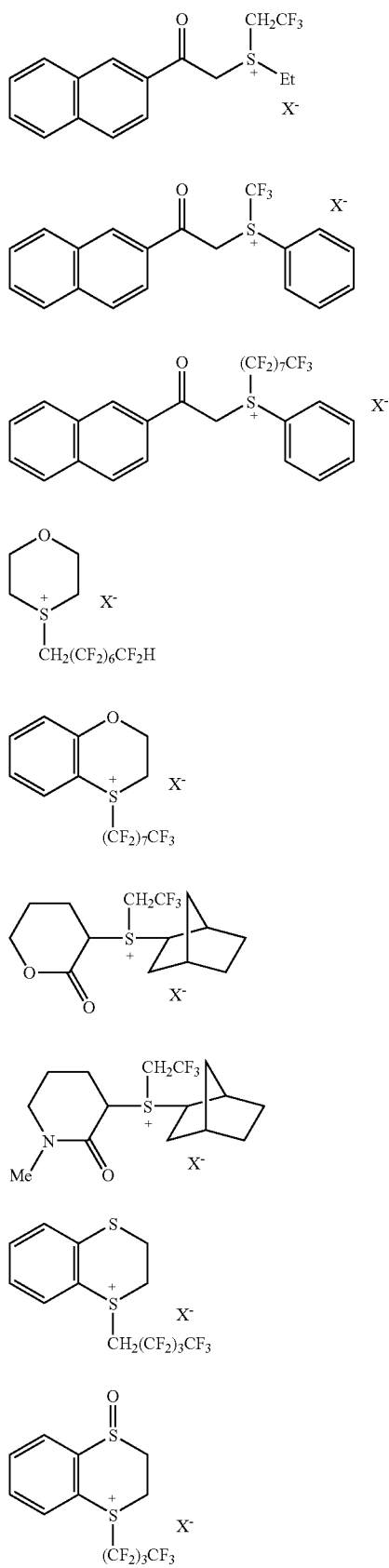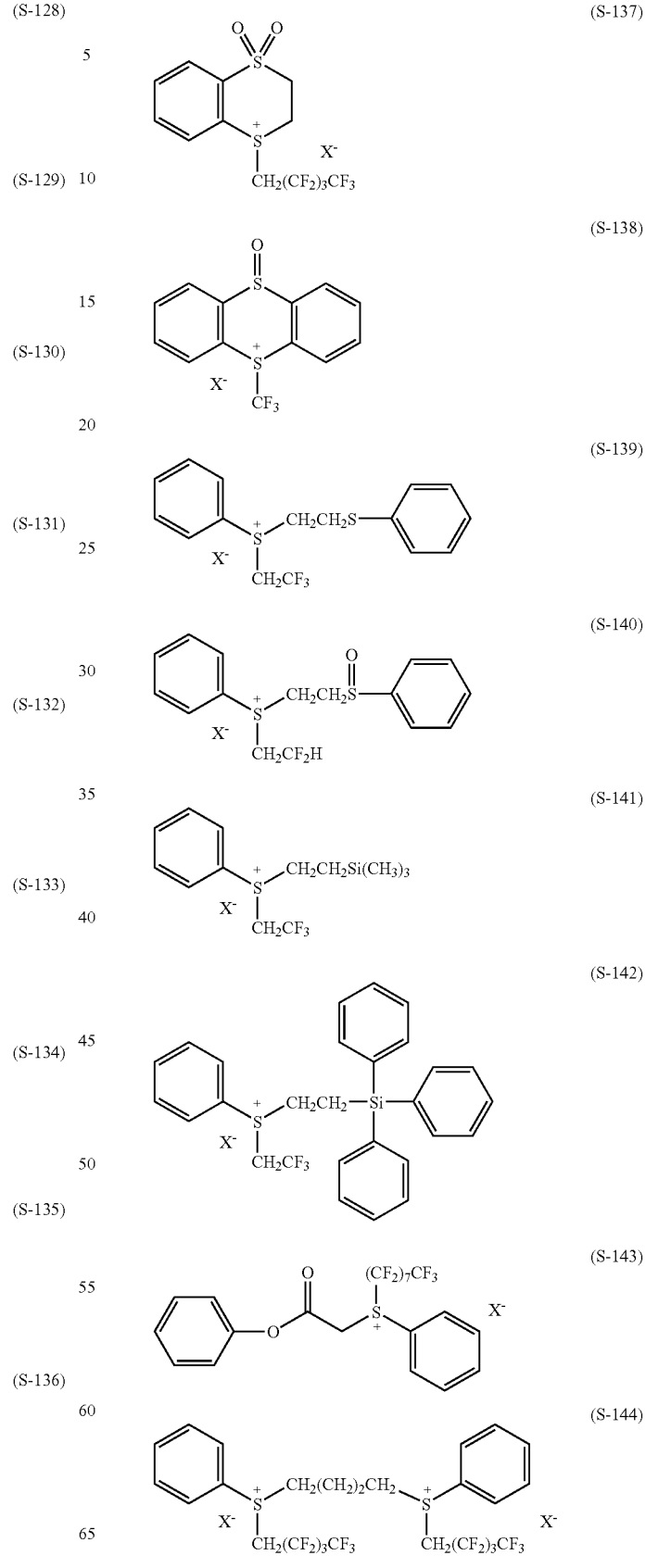

-continued
(S-145)
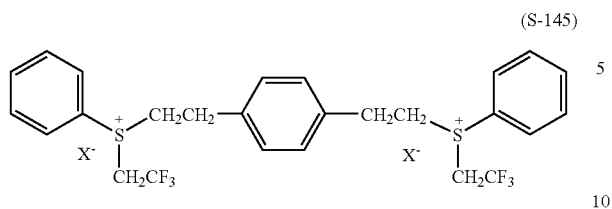
Fluoroalkyl onium salt having selenium atom as its center element:
(Se-1)
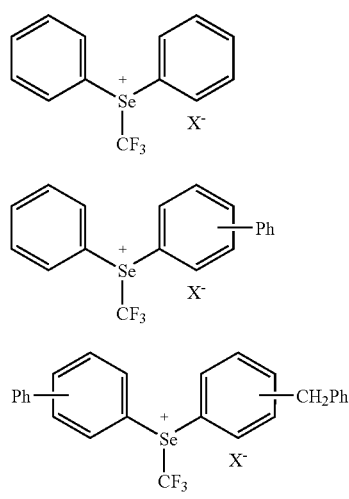
(Se-2)
(Se-3)
(Se-4)
(Se-5)
(Se-6)
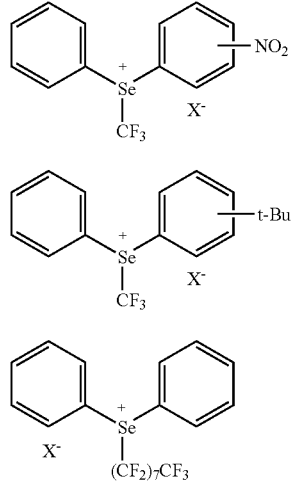
(Se-7)
(Se-8)
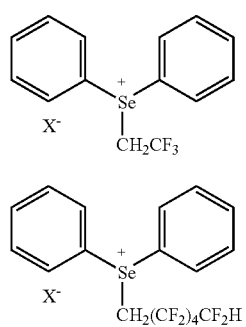
-continued
(Se-9)
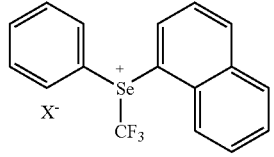
(Se-10)
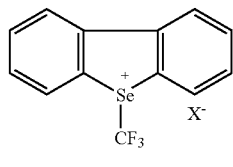
(Se-11)
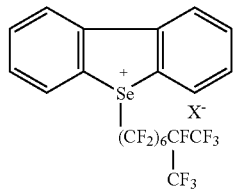
(Se-12)
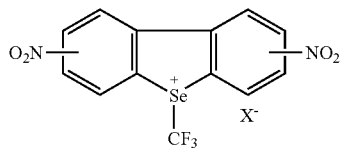
(Se-13)
(Se-14)
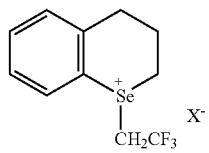
(Se-15)
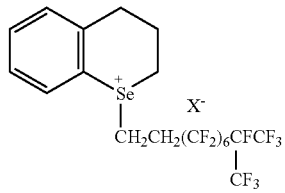
(Se-16)
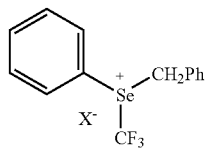
(Se-17)
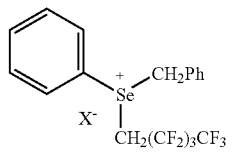

-continued
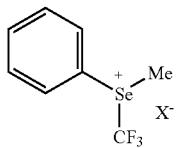 (Se-18)
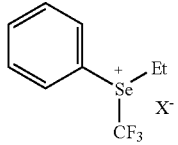 (Se-19)
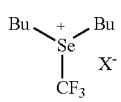 (Se-20)
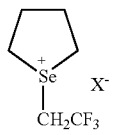 (Se-21)
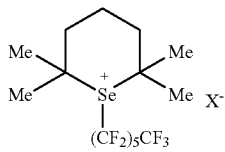 (Se-22)
Fluoroalkyl onium salt having tellurium atom as its center element:
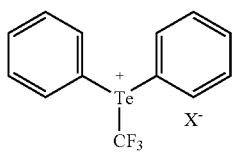 (Te-1)
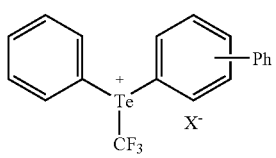 (Te-2)
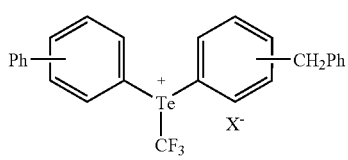 (Te-3)
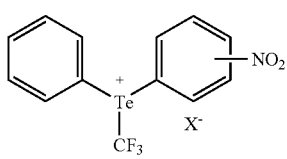 (Te-4)
-continued
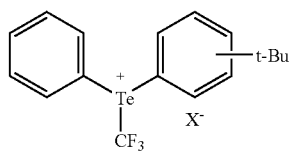 (Te-5)
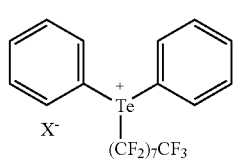 (Te-6)
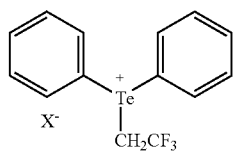 (Te-7)
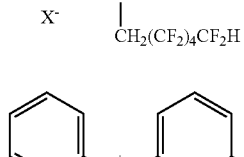 (Te-8)
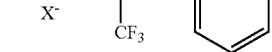 (Te-9)
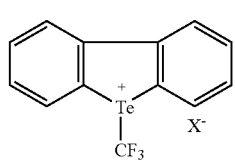 (Te-10)
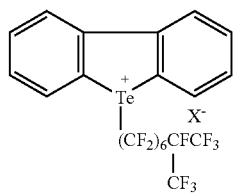 (Te-11)
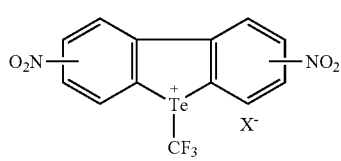 (Te-12)
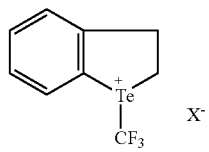 (Te-13)

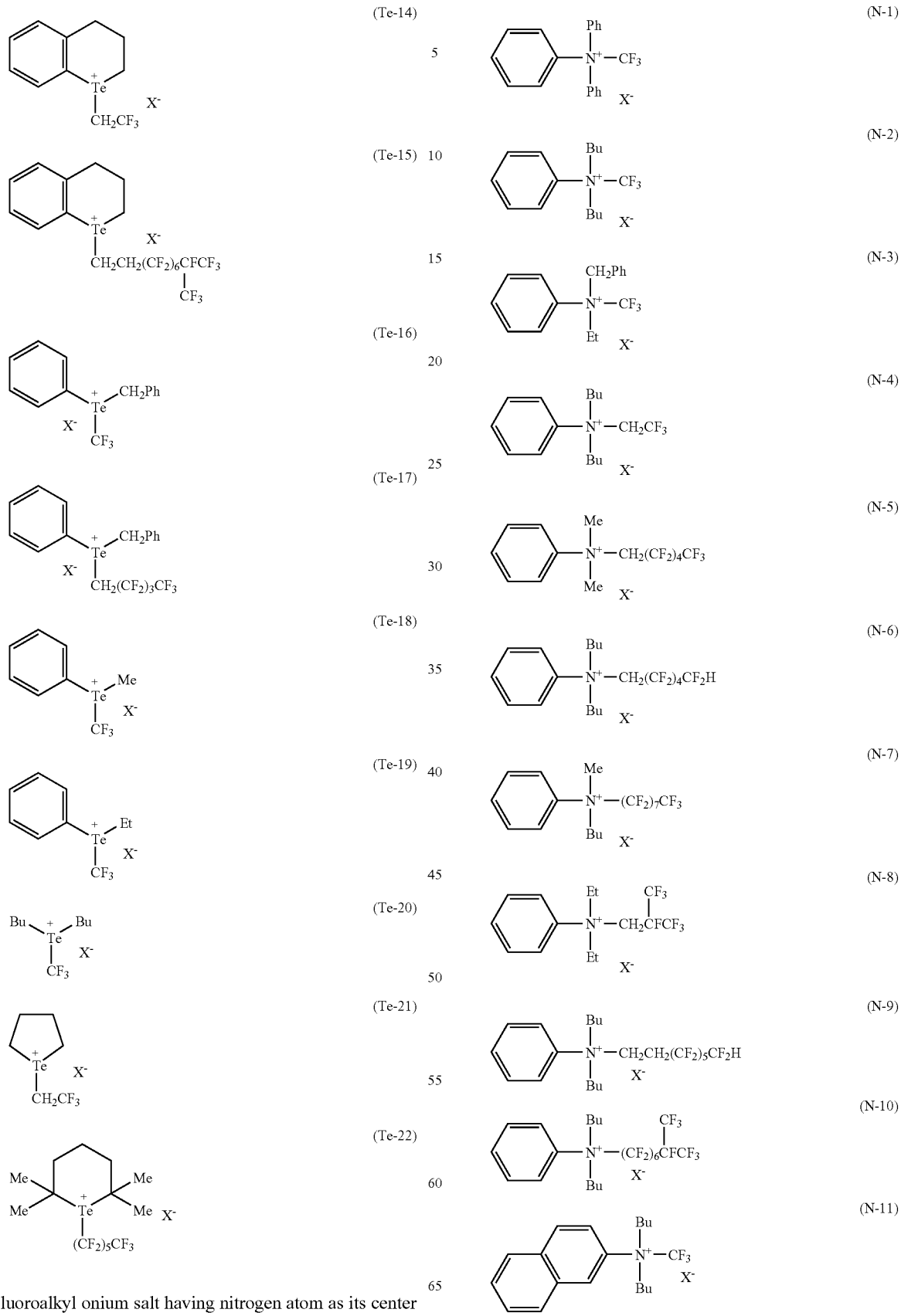
Fluoroalkyl onium salt having nitrogen atom as its center element:

-continued
(N-12) 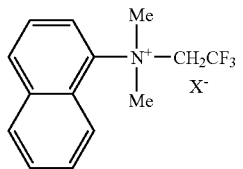
(N-13) 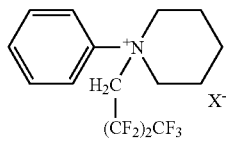
(N-14) 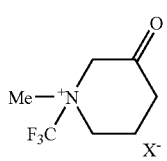
(N-15) 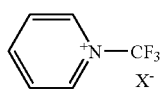
(N-16) 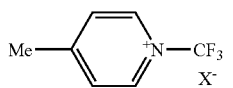
(N-17) 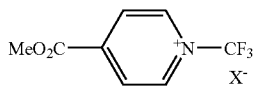
(N-18) 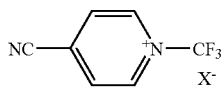
(N-19) 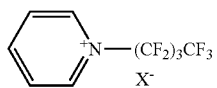
(N-20) 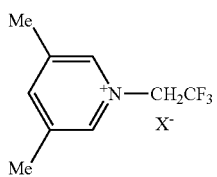
(N-21) 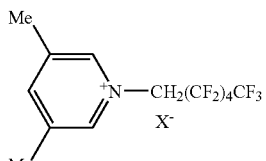
(N-22) 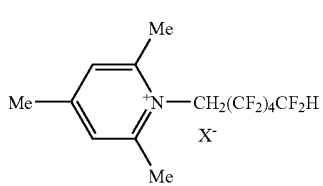
-continued
(N-23) 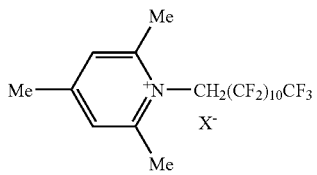
(N-24) 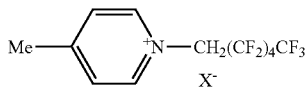
Fluoroalkyl onium salt having phosphorus atom as its center element:
(P-1) 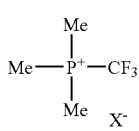
(P-2) 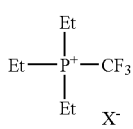
(P-3) 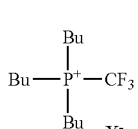
(P-4) 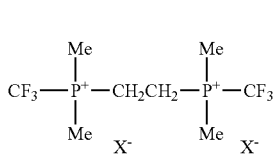
(P-5) 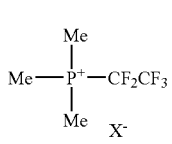
(P-6) 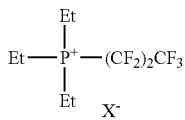
(P-7) 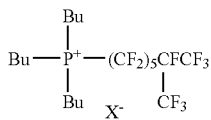
(P-8) 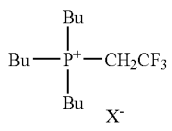

-continued
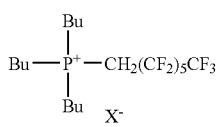
(P-9)
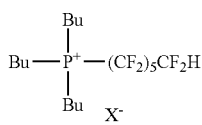
(P-10)
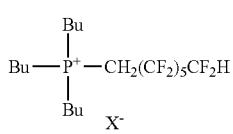
(P-11)
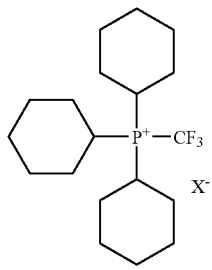
(P-12)
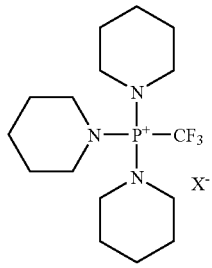
(P-13)
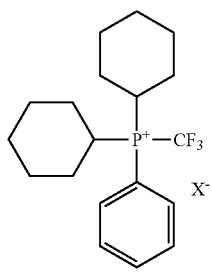
(P-14)
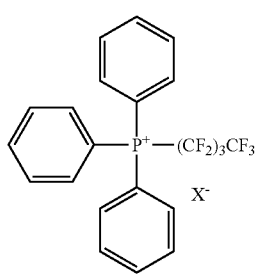
(P-15)
-continued
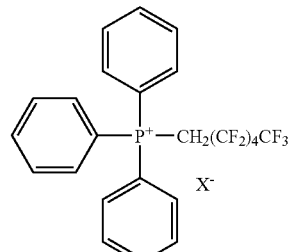
(P-16)
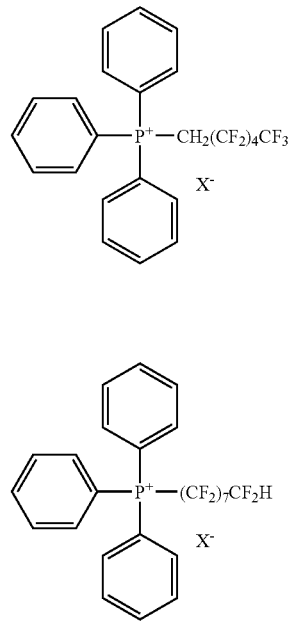
(P-17)
(P-18)
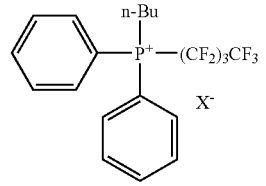
(P-19)
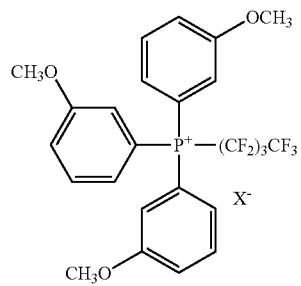
(P-20)
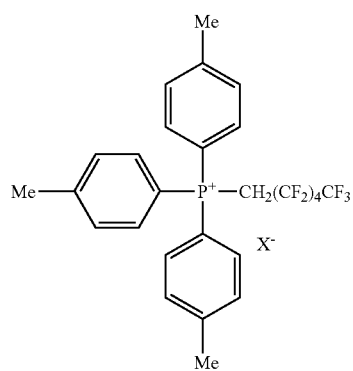

-continued (P-21) 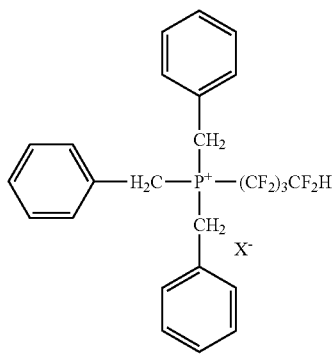

(P-22) 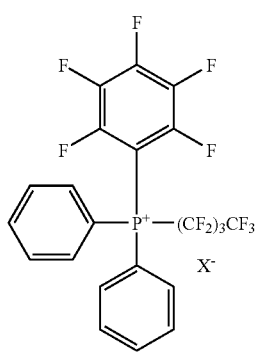

(P-23) 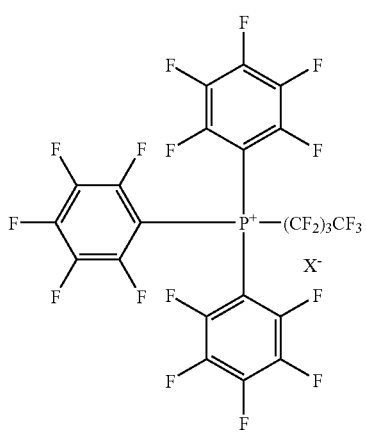

(P-24) 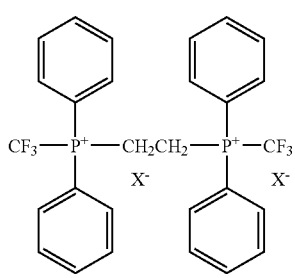

-continued (P-25) 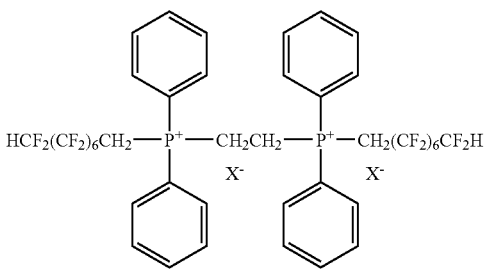

(P-26) 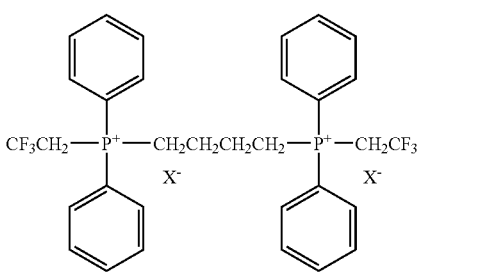

X⁻ in those exemplified fluoroalkyl onium salts is a conjugated base of Brønsted acid. Non-restricted examples of the Brønsted acid are fluoroalkylsulfonic acids such as trifluoromethanesulfonic acid, tetrafluoroethanesulfonic acid, perfluorobutanesulfonic acid, perfluoropentanesulfonic acid, perfluorohexanesulfonic acid, perfluorooctanesulfonic acid and difluoromethanesulfonic acid, methanesulfonic acid, trichloromethanesulfonic acid, benzenesulfonic acid, toluenesulfonic acid, sulfuric acid, fluorosulfonic acid, chlorosulfonic acid, $HBF_4$, $HSbF_6$, $HPF_6$, $HSbCl_5F$, $HSbCl_6$, $HAsF_6$, $HBCl_3F$, $HalCl_4$ and the like. Particularly fluoroalkylsulfonic acids which are strong acids are preferred because neither hydrogen fluoride nor hydrogen chloride is not generated.

Those onium salts having a fluorine-containing alkyl group are preferred because transparency thereof is high in a vacuum ultraviolet region and also because of good compatibility with the fluorine-containing polymer (A) having an acid-reactive group in the chemically amplifying type photoresist composition of the present invention.

The content of photoacid generator in the chemically amplifying type photoresist composition of the present invention is preferably from 0.1 to 30 parts by weight, more preferably from 0.2 to 20 parts by weight, most preferably from 0.5 to 10 parts by weight based on 100 parts by weight of the fluorine-containing polymer (A) having an acid-reactive group.

When the content of photoacid generator is less than 0.1 part by weight, sensitivity is lowered, and when the content is more than 30 parts by weight, an amount of light absorbed by the photoacid generator is increased and light does not reach a substrate sufficiently, thereby lowering resolution easily.

Also to the photoresist composition of the present invention may be added an organic base capable of acting, as a base, on an acid generated from the above-mentioned photoacid generator.

The purpose of adding the organic base is to prevent migration of the acid generated from the photoacid generator and to prevent a resist pattern from undergoing a dimensional change during an interval between the exposure and the PEB treatment. Therefore the organic base is not limited particularly as far as it is a compound capable of neutralizing the acid generated from the photoacid generator as mentioned above. The organic base is preferred because when an inorganic compound is used as a base, a very small amount of its residue remains after forming a pattern and eliminating the resist and has an adverse effect on the pattern formation. The organic base is an organic amine compound selected from nitrogen-containing compounds. Examples thereof are pyrimidine compounds such as pyrimidine, 2-aminopyrimidine, 4-aminopyrimidine, 5-aminopyrimidine, 2,4-diaminopyrimidine, 2,5-diaminopyrimidine, 4,5-diaminopyrimidine, 4,6-diaminopyrimidine, 2,4,5-triaminopyrimidine, 2,4,6-triaminopyrimidine, 4,5,6-triaminopyrimidine, 2,4,5,6-tetraaminopyrimidine, 2-hydroxypyrimidine, 4-hydroxypyrimidine, 5-hydroxypyrimidine, 2,4-dihydroxypyrimidine, 2,5-dihydroxypyrimidine, 4,5-dihydroxypyrimidine, 4,6-dihydroxypyrimidine, 2,4,5-trihydroxypyrimidine, 2,4,6-trihydroxypyrimidine, 4,5,6-trihydroxypyrimidine, 2,4,5,6-tetrahydroxypyrimidine, 2-amino-4-hydroxypyrimidine, 2-amino-5-hydroxypyrimidine, 2-amino-4,5-dihydroxypyrimidine, 2-amino-4,6-dihydroxypyrimidine, 4-amino-2,5-dihydroxypyrimidine, 4-amino-2,6-dihydroxypyrimidine, 2-amino-4-methylpyrimidine, 2-amino-5-methylpyrimidine, 2-amino-4,5-dimethylpyrimidine, 2-amino-4,6-dimethylpyrimidine, 4-amino-2,5-dimethylpyrimidine, 4-amino-2,6-dimethylpyrimidine, 2-amino-4-methoxypyrimidine, 2-amino-5-methoxypyrimidine, 2-amino-4,5-dimethoxypyrimidine, 2-amino-4,6-dimethoxypyrimidine, 4-amino-2,5-dimethoxypyrimidine, 4-amino-2,6-dimethoxypyrimidine, 2-hydroxy-4-methylpyrimidine, 2-hydroxy-5-methylpyrimidine, 2-hydroxy-4,5-dimethylpyrimidine, 2-hydroxy-4,6-dimethylpyrimidine, 4-hydroxy-2,5-dimethylpyrimidine, 4-hydroxy-2,6-dimethylpyrimidine, 2-hydroxy-4-methoxypyrimidine, 2-hydroxy-5-methoxypyrimidine, 2-hydroxy-4,5-dimethoxypyrimidine, 2-hydroxy-4,6-dimethoxypyrimidine, 4-hydroxy-2,5-dimethoxypyrimidine and 4-hydroxy-2,6-dimethoxypyrimidine, pyridine compounds such as pyridine, 4-dimethylaminopyridine and 2,6-dimethylpyridine, amines substituted with hydroxyalkyl group and having not less than 1 and not more than 4 carbon atoms such as diethanolamine, triethanolamine, triisopropanolamine, tris (hydroxymethyl)aminomethane and bis(2-hydroxyethyl) iminotris(hydroxymethyl)methane, aminophenols such as 2-aminophenol, 3-aminophenol and 4-aminophenol and the like. Preferable organic bases are pyrimidines, pyridines or amines having hydroxyl group, and particularly preferred are amines having hydroxyl group. Those organic bases may be used solely or in a mixture of two or more thereof. The content of organic base in the photoresist composition of the present invention is preferably from 0.1 to 100% by mole, more preferably from 1 to 50% by mole based on the content of photoacid generator. When the content of organic base is less than 0.1% by mole, resolution is lowered, and when the content of organic base is more than 100% by mole, sensitivity tends to be lowered.

In the chemically amplifying type photoresist composition of the present invention, when a negative resist composition is prepared using the fluorine-containing polymer (A) having a functional group undergoing condensation by an acid, a crosslinking agent may be used as case demands as mentioned above.

The crosslinking agent is not limited particularly and can be optionally selected from crosslinking agents which have been usually used for negative resists.

Examples of preferable crosslinking agent are, for instance, N-methylol melamine, N-alkoxymethylol melamine, urea compounds, epoxy compounds, isocyanate compounds and the like.

Those crosslinking agents may be used solely or in combination of two or more thereof. Among them, a combination of the melamine resin and the urea resin is advantageous.

The content of crosslinking agent in the photoresist (particularly negative type) composition of the present invention is from 3 to 70 parts by weight, preferably from 5 to 50 parts by weight, more preferably from 10 to 40 parts by weight based on 100 parts by weight of the fluorine-containing polymer (A) having an acid-reactive group. When the content is less than 3 parts by weight, a resist pattern is difficult to be formed, and the content of more than 70 parts by weight is not preferable because light transmittance is lowered, resolution is easily lowered and developing property is lowered.

The photoresist composition of the present invention may contain, as case demands, various additives which have been usually used in this field, such as dissolution inhibitor, sensitizer, dye, adhesion betterment material and water storage material. While the presence of water is necessary for generating an acid in a chemically amplifying type resist, the acid can be generated effectively in the presence of a small amount of water storage material such as polypropylene glycol.

When those additives are used, a total amount thereof is up to about 20% by weight based on the weight of the whole solids in the composition.

In the chemically amplifying type photoresist composition of the present invention, the solvent (C) is one which is capable of dissolving the fluorine-containing polymer (A) having an acid-reactive functional group, the photoacid generator (B) and the above-exemplified various additives. The solvent is not limited particularly as far as good coatability (surface smoothness, uniformity of coating thickness, etc.) can be obtained.

Examples of the preferable solvent (C) are, for instance, cellosolve solvents such as methyl cellosolve, ethyl cellosolve, methyl cellosolve acetate and ethyl cellosolve acetate, ester solvents such as diethyl oxalate, ethyl pyruvate, ethyl-2-hydroxybutyrate, ethyl acetoacetate, butyl acetate, amyl acetate, ethyl butyrate, butyl butyrate, methyl lactate, ethyl lactate, methyl 3-methoxypropionate, ethyl 3-methoxypropionate, methyl 2-hydroxyisobutyrate and ethyl 2-hydroxyisobutyrate, propylene glycol solvents such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate and dipropylene glycol dimethyl ether, ketone solvents such as 2-hexanone, cyclohexanone, methyl amino ketone and 2-heptanone, aromatic hydrocarbons such as toluene, xylene, chlorobenzene and chlorotoluene, a solvent mixture of two or more thereof and the like.

Also in order to enhance solubility of the fluorine-containing polymer (A), a fluorine-containing solvent may be used as case demands.

Examples thereof are, for instance, $CH_3CCl_2F$ (HCFC-141b), a mixture of $CF_3CF_2CHCl_2$ and $CClF_2CF_2CHCl$ (HCFC-225), perfluorohexane, perfluoro(2-butyltetrahydrofuran), methoxy-nonafluorobutane, 1,3-bistrifluoromethylbenzene, and in addition, fluorine-containing alcohols such as:

$H(CF_2CF_2)_{\overline{n}}CH_2OH$ (n: an integer of from 1 to 3) $F(CF_2)_{\overline{n}}CH_2OH$ (n: an integer of from 1 to 5) and $(CF_3)_{\overline{2}}CHOH$, benzotrifluoride, perfluorobenzene, perfluoro(tributylamine), $ClCF_2CFClCF_2CFCl_2$ and the like.

Those fluorine-containing solvents may be used solely, in a mixture of two or more thereof or in a mixture of one or more of the fluorine-containing solvents and non-fluorine-containing solvents.

The amount of the solvent (C) is selected depending on kind of solids to be dissolved, kind of a substrate to be coated, an intended coating thickness, etc. From the viewpoint of easiness of coating, the solvent is used in such an amount that the concentration of the whole solids of the resist composition becomes from 0.5 to 70% by weight, preferably from 1 to 50% by weight, particularly preferably from 5 to 30% by weight.

The chemically amplifying type resist composition of the present invention is subjected to resist pattern formation according to conventional photoresist technology. In order to form a pattern properly, first, a solution of the photoresist composition is applied on a substrate such as a silicon wafer by a spinner or the like, and is dried to form a photosensitive layer. A pattern is drawn by irradiating the layer with ultraviolet ray, deep-UV, excimer laser or X-ray by a reduction projection exposure system, etc. through a proper mask pattern or the pattern is drawn with an electron beam, and then heating follows. The layer is then subjected to developing treatment with a developing solution, for example, an aqueous alkali solution such as an aqueous solution of 1 to 10% by weight of tetramethyl ammonium hydroxide. Thus an image faithful to the mask pattern can be obtained by the above-mentioned pattern forming method.

It was found that by using the chemically amplifying type resist composition of the present invention, a resist film (photosensitive layer) having a high transparency even in a vacuum ultraviolet region could be formed. Therefore the resist composition of the present invention can be preferably used particularly for a photolithography process using a $F_2$ laser (wavelength of 157 nm) which is under development aiming at a technology node of 0.1 µm.

The present invention is then explained below by means of Examples and Preparation Examples, but is not limited to them.

In the following Examples and Preparation Examples, equipment and measuring conditions used for evaluation of physical properties are as follows.

(1) NMR: NMR analyzer is AC-300 available from BRUKER CO., LTD.
Measuring conditions of $^1$H-NMR: 300 MHz (tetramethylsilane=0 ppm)
Measuring conditions of $^{19}$F-NMR: 300 MHz (trichlorofluoromethane=0 ppm)

(2) IR analysis: Measuring is carried out at room temperature with a Fourier-transform infrared spectrophotometer 1760X available from Perkin Elmer Co., Ltd.

(3) GPC: A number average molecular weight is calculated from data measured by gel permeation chromatography (GPC) by using GPC HLC-8020 available from Toso Kabushiki Kaisha and columns available from Shodex Co., Ltd. (one GPC KF-801, one GPC KF-802 and two GPC KF-806M were connected in series) and flowing tetrahydrofuran (THF) as a solvent at a flowing rate of 1 ml/minute.

(4) GC-Mass: Measurement is carried out by using QP1000 available from Shimadzu Corporation. Detection is carried out by an impact ionization method at an ionization energy of 70 eV.

PREPARATION EXAMPLE 1

(Synthesis of Norbornene Having —COF Group)

A 500 ml four-necked glass flask equipped with a reflux condenser, thermometer, stirrer and dropping funnel was charged with 136 g of cyclopentadiene and 1.0 g of hydroquinone and was cooled to 0° to 5° C. Thereto was added dropwise 233 g of α-fluoroacrylic acid fluoride ($CH_2$=CFCOF) over three hours in nitrogen gas stream. After completion of the addition, stirring was carried out for three hours at room temperature.

The reaction mixture was subjected to distillation under reduced pressure to obtain 360 g of 5-norbornene-2-carboxylic acid fluoride:

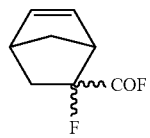

(melting point: 73° to 75° C./45 mmHg) which is a norbornene compound having —COF group (yield: 90%)

The above-mentioned structure of this compound was determined by GC-Mass, $^{19}$F-NMR and $^1$H-NMR analyses.

EXAMPLE 1

(Synthesis of (5-norbornene-2-yl)trifluoromethyl ketone)

A 100 ml three-necked flask equipped with a thermometer, cooling tube having a 3-way cock and dropping funnel was charged with 17 g (112 mmol) of 5-norbornene-2-carboxylic acid methyl ester (mixture of endo-form and exo-form) and 0.45 g (3 mmol) of cesium fluoride and was cooled in ice bath in nitrogen gas atmosphere. While maintaining the inside temperature of the flask at 3° to 10° C., 22 g (156 mmol) of $CF_3SiMe_3$ was added dropwise over two hours with stirring. After increasing the flask temperature to room temperature and stirring for three hours, 2 g (8 mmol) of tetrabutylammonium fluoride was added thereto and stirring was carried out for one hour. The reaction solution was poured into ice water, followed by extraction with diethylether. After drying an organic phase with calcium chloride, refining was carried out by distillation under reduced pressure and 12 g (yield: 56%, based on 5-norbornene-2-carboxylic acid methyl ester) of (5-norbornene-2-yl)trifluoromethyl ketone was obtained.

Physical properties of the obtained product were as follows.

$^{19}$F-NMR (solvent: $CDCl_3$): −78.0 (s, $CF_3$, exo-form), −78.3 (s, $CF_3$, endo-form)
MS: 190 ($M^+$), 121 ($M^+$—$CF_3$), 66 ($C_5H_6$)
IR: 1753 $cm^{-1}$ (C=O), 1574 $cm^{-1}$ (C=C)

EXAMPLE 2

(Synthesis of (5-norbornene-2-yl)-1,1,1,3,3,3-hexafluoro-2-propanol (NB-1))

A 100 ml three-necked flask equipped with a thermometer, cooling tube having a 3-way cock and dropping funnel was charged with 12 g (64 mmol) of (5-norbornene-2-yl)trifluoromethyl ketone (mixture of endo-form and exo-form), 11 g (79 mmol) of $CF_3SiMe_3$ and 20 ml of THF and was cooled in dry ice/acetone bath in nitrogen gas atmosphere. While maintaining the inside temperature of the flask at −70° C. or lower, 3 ml (3 mmol) of 1M THF solution of tetrabutylammonium fluoride was added gradually with stirring. After increasing the flask temperature to room temperature and stirring for three hours, 20 ml of 5% hydrochloric acid was added thereto and stirring was further carried out for three hours. After extracting with diethylether and washing with a saturated aqueous solution of sodium hydrogencarbonate, an organic phase was dried with calcium chloride. After distilling off the solvent, refining was carried out by distillation under reduced pressure and 11 g (yield: 65%, based on (5-norbornene-2-yl) trifluoromethyl ketone) of (5-norbornene-2-yl)-1,1,1,3,3,3-hexafluoro-2-propanol (NB-1) was obtained.

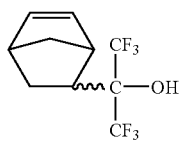

(NB-1)

Physical properties of NB-1 were as follows.
$^{19}$F-NMR (solvent: CDCl$_3$): −74.0 (q, CF$_3$, endo-form), −74.9 (q, CF$_3$, exo-form), −75.3 (q, CF$_3$, endo-form), −76.8 (q, CF$_3$, exo-form)
MS: 260 (M$^+$), 191 (M$^+$—CF$_3$), 125, 97, 66 (C$_5$H$_6$)
IR: 3510 cm$^{-1}$ (O—H), 1579 cm$^{-1}$ (C=C)

EXAMPLE 3

Synthesis of (5-norbornene-2-yl)-1,1,1,3,3,3-hexafluoro-2-propanol (NB-1) in One Pot)
A 100 ml three-necked flask equipped with a thermometer, cooling tube having a 3-way cock and dropping funnel was charged with 1.3 g (8.5 mmol) of 5-norbornene-2-carboxylic acid methyl ester (mixture of endo-form and exo-form), 6.1 g (43 mmol) of CF$_3$SiMe$_3$ and 15 ml of hexane and was cooled in ice bath in nitrogen gas atmosphere. While maintaining the inside temperature of the flask at 3° to 10° C., 2 ml (2 mmol) of 1M THF solution of tetrabutylammonium fluoride was added gradually over four hours or more with stirring. After increasing the flask temperature to room temperature and stirring for 24 hours, the reaction solution was analyzed. The product was one comprising 28% of 5-norbornene-2-carboxylic acid methyl ester, 52% of (5-norbornene-2-yl)trifluoromethyl ketone and 20% of (5-norbornene-2-yl)-1,1,1,3,3,3-hexafluoro-2-propanol (NB-1).

EXAMPLE 4

(Synthesis of (2-fluoro-5-norbornene-2-yl)-1,1,1,3,3,3-hexafluoro-2-propanol (NB-2) in One Pot)
A 100 ml three-necked flask equipped with a thermometer, cooling tube having a 3-way cock and dropping funnel was charged with 27.7 g (168 mmol) of 5-norbornene-2-carboxylic acid fluoride (mixture of endo-form and exo-form) synthesized in Preparation Example 1 and 28 g (482 mmol) of potassium fluoride and was cooled in ice bath in nitrogen gas atmosphere. While maintaining the inside temperature of the flask at 3° to 10° C., 62 g (436 mmol) of CF$_3$SiMe$_3$ was added over two hours with stirring. After increasing the flask temperature to room temperature, stirring was carried out overnight. Then the reaction solution was poured into ice water, followed by extracting with diethylether. After washing an organic phase with water, diluted hydrochloric acid and then saturated sodium bicarbonate solution, the organic phase was dried with calcium chloride. Then refining was carried out by distillation under reduced pressure and 50 g (yield: 80%) of (2-fluoro-5-norbornene-2-yl)-1,1,1,3,3,3-hexafluoro-2-propanol (NB-2) was obtained.

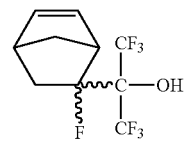

(NB-2)

Physical properties of NB-2 were as follows.
$^{19}$F-NMR (solvent: CDCl$_3$):
endo-form: −156.7 (m, F), −72.3 (m, CF$_3$), −72.0 (m, CF$_3$)
exo-form: −152.2 (m, F), −73.8 (m, CF$_3$), −72.5 (m, CF$_3$)
$^1$H-NMR (solvent: CDCl$_3$): 6.60-6.23 (1H, m, sp2CH), 6.10-5.86 (1H, m, sp2CH), 4.34-3.80 (1H, s broad, OH), 3.80-3.47 (m, 1H), 3.37-2.98 (1H, s), 2.98-2.54 (1H, s), 2.5-2.15 (1H, t), 2.10-1.61 (2H, m)
MS: 241 (M$^+$—FH$_2$O), 221, 201, 66 (C$_5$H$_6$)
IR: 3500 cm$^{-1}$ (O—H), 1590 cm$^{-1}$ (C=C)

EXAMPLE 5

(Introduction of Protective Group)
A 100 ml four-necked flask equipped with a reflux condenser, thermometer, stirrer and dropping funnel was charged with 3.5 g of sodium hydride (purity: 60%) and 10 ml of tetrahydrofuran, and while maintaining the inside temperature of the flask at 5° to 10° C., 2.1 g of norbornene (NB-2) having —C(CF$_3$)$_2$OH group prepared in Example 4 was added dropwise over one hour. After completion of the addition, stirring was carried out at room temperature for 1.5 hours. Then thereto was added dropwise 9.6 g of chloromethyl ethyl ether (ClCH$_2$OC$_2$H$_5$) over one hour. After completion of the addition, stirring was carried out at room temperature for five hours.
After terminating the reaction, water was added thereto, an organic substance was extracted with ether, and the ether layer was washed with saturated NaHCO$_3$ solution, followed by drying with anhydrous magnesium sulfate.
After the drying, ether was distilled off, and 20.5 g (yield: 77%) of norbornene compound (NB-2(1)):

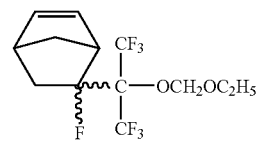

(NB-2(1))

(melting point: 58° to 60° C./1.5 mmHg) having a group:

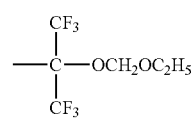

was obtained by distillation under reduced pressure.

PREPARATION EXAMPLE 2

(Synthesis of Norbornene (NBC-1) Having —COOC(CH$_3$)$_3$ Group

A 300 ml four-necked flask equipped with a reflux condenser, thermometer, stirrer and dropping funnel was charged with 61 g of cyclopentadiene, 26 g of t-butyl-α-fluoroacrylate, 50 ml of tetrahydrofuran and 0.1 g of hydroquinone, and the inside temperature of the flask was maintained at 25° C.

While stirring in nitrogen gas stream, 4.0 g of boron trifluoride-diethylether complex was added thereto dropwise, and after completion of the addition, stirring was carried out at room temperature for 48 hours for reaction.

After terminating the reaction, tetrahydrofuran was distilled off by distillation and a residue was removed. Then water was added thereto, an organic substance was extracted with methylene chloride, and after washing with 5% NaHCO$_3$ solution, methylene chloride layer was dried with anhydrous magnesium sulfate.

After the drying, an organic layer was separated and methylene chloride was distilled off, and 14 g of norbornene (NBC-1):

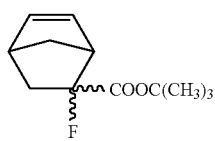

(NBC-1)

(melting point: 70° to 72° C./2 mmHg) having an acid-reactive group —COOC(CH$_3$)$_3$ was obtained by distillation under reduced pressure.

The above-mentioned structure of this compound was determined by GC-Mass, $^{19}$F-NMR and $^1$H-NMR analyses.

EXAMPLE 6

(Synthesis of Copolymer Comprising TFE and Fluorine-containing Norbornene (NB-2) Having OH Group)

A 300 ml autoclave equipped with a valve, pressure gauge and thermometer was charged with 20.7 g of fluorine-containing norbornene (NB-2) having OH group prepared in Example 4, 140 ml of HCFC-141b and 1.5 g of bis(4-t-butylcyclohexyl)peroxydicarbonate (TCP), and while cooling with dry ice/methanol solution, the inside of a system was sufficiently replaced with nitrogen gas. Then 30.0 g of TFE was introduced through the valve, followed by shaking at 40° C. for 12 hours for reaction. With the advance of the reaction, the gauge pressure was lowered from 0.96 MPaG (9.7 kgf/cm$^2$G) before the reaction to 0.91 MPaG (9.2 kgf/cm$^2$G).

After releasing the un-reacted monomer, polymerization solution was removed and after concentrating, was re-precipitated with hexane to separate a copolymer. Until a constant weight was reached, vacuum drying was carried out to obtain 4.1 g of a copolymer.

As a result of $^1$H-NMR and $^{19}$F-NMR analyses, the copolymer was a copolymer of TFE/fluorine-containing norbornene derivative (NB-2) having OH group in % by mole ratio of 50/50.

According to GPC analysis, a number average molecular weight thereof was 3,500.

EXAMPLE 7

(Synthesis of Copolymer Comprising TFE and Fluorine-containing Norbornene (NB-1) Having OH Group)

A reaction was carried out in the same manner as in Example 6 except that 19.3 g of the fluorine-containing norbornene (NB-1) having OH group prepared in Example 2 was used instead of the fluorine-containing norbornene derivative having OH group prepared in Example 4. With the advance of the reaction, the gauge pressure was lowered from 0.95 MPaG before the reaction to 0.92 MPaG.

After releasing the un-reacted monomer, polymerization solution was removed and after concentrating, was re-precipitated with hexane to separate a copolymer. Until a constant weight was reached, vacuum drying was carried out to obtain 3.7 g of a copolymer.

As a result of $^1$H-NMR and $^{19}$F-NMR analyses, the copolymer was a copolymer of TFE/fluorine-containing norbornene derivative (NB-1) having OH group in % by mole ratio of 50/50.

According to GPC analysis, a number average molecular weight thereof was 3,400.

EXAMPLE 8

Synthesis of Copolymer Comprising TFE and Fluorine-containing Norbornene Derivative (NB-2(1)) Having —OCH$_2$OC$_2$H$_5$ Group)

A reaction was carried out in the same manner as in Example 6 except that 26.2 g of the fluorine-containing norbornene (NB-2(1)) having —OCH$_2$OC$_2$H$_5$ group prepared in Example 5 was used instead of the fluorine-containing norbornene derivative having OH group prepared in Example 4. With the advance of the reaction, the gauge pressure was lowered from 0.94 MPaG (9.5 kgf/cm$^2$G) before the reaction to 0.91 MPaG (9.2 kgf/cm$^2$G). Then separation and refining were carried out in the same manner as in Example 6 and 3.9 g of a copolymer was obtained.

As a result of $^1$H-NMR and $^{19}$F-NMR analyses, the copolymer was a copolymer of TFE/fluorine-containing norbornene derivative (NB-2(1)) having —OCH$_2$OC$_2$H$_5$ group in % by mole ratio of 50/50.

According to GPC analysis, a number average molecular weight thereof was 2,600.

EXAMPLE 9

(Synthesis of Copolymer Comprising TFE, Fluorine-containing Norbornene Derivative (NB-2(1)) Having —OCH$_2$OC$_2$H$_5$ group and 2-norbornene)

A reaction was carried out in the same manner as in Example 6 except that 18.5 g of the fluorine-containing norbornene (NB-2(1)) having —OCH$_2$OC$_2$H$_5$ group prepared in Example 5 and 2.1 g of 2-norbornene were used instead of the fluorine-containing norbornene derivative having OH group prepared in Example 4. Then separation and refining were carried out in the same manner as in Example 6 and 4.3 g of a copolymer was obtained.

As a result of $^1$H-NMR and $^{19}$F-NMR analyses, the copolymer was a copolymer of TFE/fluorine-containing norbornene derivative (NB-2(1)) having —OCH$_2$OC$_2$H$_5$ group/2-norbornene in % by mole ratio of 56/31/13.

According to GPC analysis, a number average molecular weight thereof was 3,200.

EXAMPLE 10

(Synthesis of Copolymer Comprising TFE, Fluorine-containing Norbornene Derivative (NB-2) Having —OH Group and Fluorine-Containing Norbornene Derivative (NBC-1) Having —COOC($CH_3$)$_3$ Group)

A 500 ml autoclave equipped with a valve, pressure gauge, stirrer and thermometer was charged with 3.1 g of the fluorine-containing norbornene derivative (NB-2) having —OH group prepared in Example 4, 21.0 g of the fluorine-containing norbornene derivative (NBC-1) having —COOC($CH_3$)$_3$ group prepared in Preparation Example 2, 250 ml of HCFC-141b and 6.6 g of bis(4-t-butylcyclohexyl)peroxydicarbonate (TCP), and the inside of a system was sufficiently replaced with nitrogen gas. Then 44 g of TFE was introduced through the valve, followed by shaking at 40° C. for 12 hours for reaction.

After releasing the un-reacted monomer, polymerization solution was removed and after concentrating, was re-precipitated with hexane to separate a copolymer. Until a constant weight was reached, vacuum drying was carried out to obtain 6.9 g of a copolymer.

As a result of $^1$H-NMR and $^{19}$F-NMR analyses, the copolymer was a copolymer of TFE/fluorine-containing norbornene derivative (NB-2) having —OH group/fluorine-containing norbornene derivative (NBC-1) having —COOC($CH_3$)$_3$ group in % by mole ratio of 54/9.2/36.8.

According to GPC analysis, a number average molecular weight thereof was 2,800.

EXAMPLE 11

(Synthesis of Copolymer Comprising TFE, Fluorine-containing Norbornene Derivative (NB-2) Having —OH Group and Fluorine-Containing Norbornene Derivative (NBC-1) Having —COOC($CH_3$)$_3$ Group)

A reaction was carried out in the same manner as in Example 10 except that 9.2 g of the fluorine-containing norbornene derivative (NB-2) having OH group prepared in Example 4 and 16.3 g of the fluorine-containing norbornene derivative (NBC-1) having —COOC($CH_3$)$_3$ group prepared in Preparation Example 2 were used. Then separation and refining were carried out in the same manner as in Example 10 and 7.2 g of a copolymer was obtained.

As a result of $^1$H-NMR and $^{19}$F-NMR analyses, the copolymer was a copolymer of TFE/fluorine-containing norbornene derivative (NB-2) having —OH group/fluorine-containing norbornene derivative (NBC-1) having —COOC($CH_3$)$_3$ group in % by mole ratio of 52/29/19.

According to GPC analysis, a number average molecular weight thereof was 3,300.

EXAMPLE 12

(Measurement of Transparency at a Wavelength of 157 nm)

(1) Preparation of Coating Composition

The fluorine-containing polymers prepared in Examples 6 to 11 were dissolved in butyl acetate so that the concentration thereof became 3%, respectively. Thus coating compositions were prepared.

(2) Coating (i) Coating on a Substrate ($MgF_2$) for Measuring Transparency

Each coating composition was applied on a $MgF_2$ substrate at room temperature with a spin coater under the condition of 1,000 rpm. After the coating, the coating composition was baked at 100° C. for 15 minutes to form transparent coating films.

(ii) Measurement of Coating Thickness

Coating films were formed by applying the respective coating compositions under the same conditions as above except that a silicon wafer was used instead of the $MgF_2$ substrate.

The coating thickness was measured with a AFM device (SPI3800 available from SEIKO DENSHI KABUSHIKI KAISHA). The results are shown in Table 1.

(3) Measurement of Transparency in Vacuum Ultraviolet Region (i) Measuring Device Setani-Namioka type spectrometer (BL-7B available from HIGH ENERGY KENKYU KIKO)

Slit: 7/8-7/8

Detector: PMT

Grating (GII: Blaze wavelength 160 nm, 1,200 gratings/mm)

For an optical system, refer to Rev. Sic. Instrum., 60(7), 1917 (1989) by H. Namba, et al.

(ii) Measurement of Transmitting Spectrum

A transmitting spectrum at a wavelength of 200 to 100 nm in a coating film formed by applying each coating composition on the $MgF_2$ substrate by the method of (2)(i) was measured using the above-mentioned device. Further a molecular absorption coefficient was calculated from the transmittance at 157 nm and the coating thickness and is shown in Table 1.

EXAMPLE 13

(Evaluation of Dry Etching Resistivity)

10% butyl acetate solutions of fluorine-containing polymers prepared in Examples 6 to 11 were prepared and coated on a Si substrate with a spin coater so that the coating thickness became 200 nm. After the coating film was pre-baked at 120° C. for 2 minutes, the coating thickness was measured with an interference coating thickness meter. Then the coated substrate was put in a chamber of ICP (inductively-coupled plasma) etching equipment to carry out etching. A pressure of etching gas (Ar/$N_2$/$C_4F_8$ mixed gas) was 10 mTorr. Plasma etching was carried out at 13.56 MHz and 900 W for an upper electrode and at 400 kHz and 100 W for a lower electrode. An etching time was 60 seconds.

The coating thickness after the etching was measured with an interference coating thickness meter and an etching rate was calculated. For comparison, an etching rate was obtained similarly using a resist (TArF-6a-63 available from Tokyo Oka Kabushiki Kaisha) used for lithography for ArF laser. The etching rate was represented in comparison with the rate obtained for comparison. Namely, each etching rate is shown by a ratio to the etching rate of comparative polymer (the above-mentioned resist for ArF laser) provided that the latter etching rate is 1. The results are shown in Table 1.

EXAMPLE 14

Evaluation of Solubility in Developing Solution (1) Deprotection Reaction of Protective Group Each protective group contained in the fluorine-containing polymers of Examples 6 to 11 was subjected to deprotection by reacting the fluorine-containing polymers with trifluoroacetic acid by using dichloromethane solvent.

It was confirmed by $^1$H-NMR and IR analyses that not less than 85% of protective groups were deprotected and converted to OH group or COOH group (2) Coating 10% butyl acetate solutions of fluorine-containing polymers prepared in Examples 6 to 11 and deprotected fluorine-containing polymers obtained above were prepared and coated on a Si substrate with a spin coater so that a coating thickness became 200 nm, followed by drying.

(3) Determination of Solubility

The Si substrate after the drying was dipped in a 2.38% aqueous solution of tetramethylammonium hydroxide for 60 seconds. Then the substrate was removed and dried at room temperature, and whether or not there was a remaining film was checked with naked eyes.

When there remain no film, solubility is assumed to be ◯. The results are shown in Table 1

EXAMPLE 15

(1) Preparation of Coating Composition

The fluorine-containing polymers (A) prepared in Examples 8 to 11 and a photoacid generator (B) in an amount of 5% by weight based on the polymer (A) were dissolved in butyl acetate as the solvent (C) and a concentration of the polymer was diluted to 5% by weight.

As the photoacid generator, S-(trifluoromethyl)-dibenzothiopheniumtrifluoromethane sulfonate:

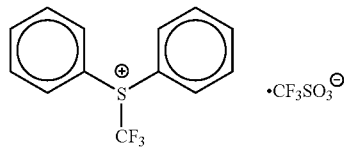

was used.

(2) Coating

Coating compositions were coated on a Si substrate with a spin coater so that a coating thickness became 200 nm, followed by drying.

(3) Measurement of Transparency in Vacuum Ultraviolet Region

Measurement was made in the same manner as in Example 12. A molecular absorption coefficient at 157 nm is shown in Table 1.

EXAMPLE 16

(Synthesis of Copolymer Comprising TFE and Fluorine-containing Norbornene (NB-2) Having OH Group)

A 500 ml autoclave equipped with a valve, pressure gauge, stirrer and thermometer was charged with 35.0 g of the fluorine-containing norbornene (NB-2) having OH group prepared in Example 4, 250 ml of HCFC-141b and 6.5 g of bis(4-t-butylcyclohexyl)peroxydicarbonate (TCP), and while cooling with dry ice/methanol solution, the inside of a system was sufficiently replaced with nitrogen gas. Then 52.0 g of TFE was introduced through the valve, followed by stirring at 40° C. for 12 hours for reaction. With the advance of the reaction, the gauge pressure was lowered from 0.96 MPaG (9.7 kgf/cm$^2$G) before the reaction to 0.91 MPaG (9.2 kgf/cm$^2$G).

After releasing the un-reacted monomer, the polymerization solution was removed and after concentrating, was re-precipitated with hexane to separate a copolymer. Until a constant weight was reached, vacuum drying was carried out to obtain 6.0 g of a copolymer.

As a result of $^1$H-NMR and $^{19}$F-NMR analyses, the copolymer was a copolymer of TFE/fluorine-containing norbornene derivative (NB-2) having OH group in % by mole ratio of 50/50.

According to GPC analysis, a number average molecular weight thereof was 5,500.

EXAMPLE 17

(Synthesis of Copolymer Comprising TFE and Fluorine-containing Norbornene Derivative (NB-2(1)) Having —OCH$_2$OC$_2$H$_5$ Group)

A reaction was carried out in the same manner as in Example 16 except that 40.0 g of the fluorine-containing norbornene derivative (NB-2(1)) having —OCH$_2$OC$_2$H$_5$ group prepared in Example 5 was used instead of the fluorine-containing norbornene derivative (NB-2) having OH group prepared in Example 4. With the advance of the reaction, the gauge pressure was lowered from 0.94 MPaG (9.5 kgf/cm$^2$G) before the reaction to 0.91 MPaG (9.2 kgf/cm$^2$G). Then separation and refining were carried out in the same manner as in Preparation Example 1 and 7.5 g of a copolymer was obtained.

As a result of $^1$H-NMR and $^{19}$F-NMR analyses, the copolymer was a copolymer of TFE/fluorine-containing norbornene derivative (NB-2(1)) having —OCH$_2$OC$_2$H$_5$ group in % by mole ratio of 50/50.

According to GPC analysis, a number average molecular weight thereof was 4,600.

TABLE 1

| Fluorine-containing polymer | Ex. 12 Absorption coefficient at 157 nm (µm$^{-1}$) | Ex. 13 Etching rate (to ArF resist) | Ex. 14 Solubility in developing solution | | Ex. 15 Absorption coefficient at 157 nm (µm$^{-1}$) |
|---|---|---|---|---|---|
| | | | Before deprotection | After deprotection | |
| Ex. 6 | 1.4 | 0.92 | ◯ | — | 1.6 |
| Ex. 7 | 1.8 | 0.96 | ◯ | — | 2.0 |
| Ex. 8 | 1.9 | 0.82 | X | ◯ | 2.2 |
| Ex. 9 | 2.0 | 0.86 | X | ◯ | 2.3 |
| Ex. 10 | 2.8 | 0.93 | X | ◯ | 3.0 |
| Ex. 11 | 2.3 | 0.90 | ◯ | ◯ | 2.5 |

EXAMPLE 18

(Synthesis of Copolymer Comprising TFE, Fluorine-containing) Norbornene Derivative (NB-2) Having —OH Group and Fluorine-Containing Norbornene Derivative (NB-2(1)) Having —OCH$_2$OC$_2$H$_5$ Group A 500 ml autoclave equipped with a valve, pressure gauge, stirrer and thermometer was charged with 18.3 g of the fluorine-containing norbornene derivative (NB-2) having —OH group prepared in Example 4, 14.8 g of the fluorine-containing norbornene derivative (NB-2(1)) having —OCH$_2$OC$_2$H$_5$ group prepared in Example 5, 250 ml of HCFC-141b and 6.6 g of bis(4-t-butylcyclohexyl)peroxydicarbonate (TCP), and the inside of a system was sufficiently replaced with nitrogen gas. Then 52.0 g of TFE was introduced through the valve, followed by stirring at 40° C. for 12 hours for reaction.

After releasing the un-reacted monomer, polymerization solution was removed and after concentrating, was re-precipitated with hexane to separate a copolymer. Until a constant weight was reached, vacuum drying was carried out to obtain 6.9 g of a copolymer.

As a result of $^1$H-NMR and $^{19}$F-NMR analyses, the copolymer was a copolymer of TFE/fluorine-containing norbornene derivative (NB-2) having —OH group/fluorine-containing norbornene derivative (NB-2(1)) having —OCH$_2$OC$_2$H$_5$ group in % by mole ratio of 50/19/31.

According to GPC analysis, a number average molecular weight thereof was 3,000.

EXAMPLE 19

(Synthesis of Copolymer Comprising TFE, Fluorine-Containing) Norbornene Derivative (NB-2) Having —OH Group and Fluorine-Containing Norbornene Derivative (NB-2(1)) Having —OCH$_2$OC$_2$H$_5$ Group Polymerization reaction, separation and refining of a polymer were carried out in the same manner as in Example 18 except that 24.5 g of the fluorine-containing norbornene derivative (NB-2) having —OH group, 7.4 g of the fluorine-containing norbornene derivative (NB-2(1)) having —OCH$_2$OC$_2$H$_5$ group, 52.5 g of TFE and 6.5 g of TCP were used. Thus 7.2 g of a copolymer was obtained.

As a result of $^1$H-NMR and $^{19}$F-NMR analyses, the copolymer was a copolymer of TFE/fluorine-containing norbornene derivative (NB-2) having —OH group/fluorine-containing norbornene derivative (NB-2(1)) having —OCH$_2$OC$_2$H$_5$ group in % by mole ratio of 50/40/10.

According to GPC analysis, a number average molecular weight thereof was 3,200.

EXAMPLE 20

(Synthesis of Copolymer Comprising TFE, Fluorine-containing Norbornene Derivative (NB-2) Having —OH Group and Fluorine-containing Norbornene Derivative (NB-2(1)) Having —OCH$_2$OC$_2$H$_5$ Group)

Polymerization reaction, separation and refining of a polymer were carried out in the same manner as in Example 18 except that 27.5 g of the fluorine-containing norbornene derivative (NB-2) having —OH group, 3.7 g of the fluorine-containing norbornene derivative (NB-2(1)) having —OCH$_2$OC$_2$H$_5$ group, 52.0 g of TFE and 6.5 g of TCP were used. Thus 7.6 g of a copolymer was obtained.

As a result of $^1$H-NMR and $^{19}$F-NMR analyses, the copolymer was a copolymer of TFE/fluorine-containing norbornene derivative (NB-2) having —OH group/fluorine-containing norbornene derivative (NB-2(1)) having —OCH$_2$OC$_2$H$_5$ group in % by mole ratio of 50/46/4.

According to GPC analysis, a number average molecular weight thereof was 3,500.

EXAMPLE 21

(Synthesis of Copolymer Comprising TFE, Fluorine-containing Norbornene Derivative (NB-2) Having —OH Group and Fluorine-containing Norbornene Derivative (NB-2(1) Having —COOC(CH$_3$)$_3$Group)

A 500 ml autoclave equipped with a valve, pressure gauge, stirrer and thermometer was charged with 24.5 g of the fluorine-containing norbornene derivative (NB-2) having —OH group prepared in Example 4, 4.7 g of the fluorine-containing norbornene derivative (NBC-1) having —COOC(CH$_3$)$_3$ group prepared in Preparation Example 2, 250 ml of HCFC-141b and 6.5 g of bis(4-t-butylcyclohexyl)peroxydicarbonate (TCP), and the inside of a system was sufficiently replaced with nitrogen gas. Then 52.0 g of TFE was introduced through the valve, followed by stirring at 40° C. for 12 hours for reaction.

After releasing the un-reacted monomer, polymerization solution was removed and after concentrating, was re-precipitated with hexane to separate a copolymer. Until a constant weight was reached, vacuum drying was carried out to obtain 6.9 g of a copolymer.

As a result of $^1$H-NMR and $^{19}$F-NMR analyses, the copolymer was a copolymer of TFE/fluorine-containing norbornene derivative (NB-2) having —OH group/fluorine-containing norbornene derivative (NBC-1) having —COOC(CH$_3$)$_3$ group in % by mole ratio of 50/40/10.

According to GPC analysis, a number average molecular weight thereof was 3,800.

EXAMPLE 22

(Synthesis of Copolymer Comprising TFE, Fluorine-containing Norbornene Derivative (NB-2) Having —OH Group and Fluorine-containing Norbornene Derivative (NB-2(1) Having —COOC(CH$_3$)$_3$Group)

Polymerization reaction, separation and refining of a polymer were carried out in the same manner as in Example 21 except that 27.5 g of the fluorine-containing norbornene derivative (NB-2) having —OH group, 2.3 g of the fluorine-containing norbornene derivative (NBC-1) having —COOC(CH$_3$)$_3$ group, 52.0 g of TFE and 6.5 g of TCP were used. Thereby 7.3 g of a copolymer was obtained.

As a result of $^1$H-NMR and $^{19}$F-NMR analyses, the copolymer was a copolymer of TFE/fluorine-containing norbornene derivative (NB-2) having —OH group/fluorine-containing norbornene derivative (NBC-1) having —COOC(CH$_3$)$_3$ group in % by mole ratio of 50/47/3.

According to GPC analysis, a number average molecular weight thereof was 4,000.

EXAMPLE 23

(Synthesis of Copolymer Comprising TFE and Fluorine-containing Norbornene Derivative (NB-1) Having OH Group)

Polymerization reaction, separation and refining of a polymer were carried out in the same manner as in Example 16 except that 32.5 g of the fluorine-containing norbornene (NB-1) having OH group prepared in Example 2 was used instead of the fluorine-containing norbornene (NB-2) having OH group. Thereby 4.5 g of a copolymer was obtained.

As a result of $^1$H-NMR and $^{19}$F-NMR analyses, the copolymer was a copolymer of TFE/fluorine-containing norbornene (NB-1) having —OH group in % by mole ratio of 50/50.

According to GPC analysis, a number average molecular weight thereof was 3,800.

EXAMPLE 24

(Measurement of Transparency at a Wavelength of 157 nm)

(1) Preparation of coating composition, (2) coating and (3) measurement of transparency in vacuum ultraviolet region were carried out in the same manner as in Example 12 by using the respective fluorine-containing polymers prepared in Examples 16 to 23. A molecular absorption coefficient at 157 nm is shown in Table 2.

EXAMPLE 25

Evaluation of Dry Etching Resistivity)

Dry etching resistivity was evaluated in the same manner as in Example 13 by using the respective fluorine-containing polymers prepared in Examples 16 to 23. The results are shown in Table 2.

EXAMPLE 26

(Evaluation of Solubility in Developing Solution)

(1) Deprotection reaction of a protective group, (2) coating and (3) determination of solubility were carried out in the same manner as in Example 14 by using the respective fluorine-containing polymers prepared in Examples 16 to 23. The results are shown in Table 2.

EXAMPLE 27

(1) Preparation of resist composition, (2) coating and (3) measurement of transparency in vacuum ultraviolet region were carried out in the same manner as in Example 15 by using the respective fluorine-containing polymers prepared in Examples 16 to 23. The results are shown in Table 2.

PREPARATION EXAMPLE 3

(Synthesis of Fluorine-Containing Norbornene Derivative (NBC-3) Having —COOC(CH$_3$)$_3$ Group)

After the inside of a 2-liter four-necked flask equipped with a magnetic stirrer, dropping funnel, 3-way cock and thermometer was replaced with nitrogen gas, the flask was charged with 117 ml (0.55 mol) of HN(Si(CH$_3$)$_3$)$_2$ and 200 ml of TFE. After cooling in dry ice/acetone bath, 328 ml (0.525 mol) of 1.6 N hexane solution of n-BuLi was added dropwise over 45 minutes so that the solution temperature did not exceed −50° C. Further after stirring for 30 minutes, thereto was added dropwise over 45 minutes a solution prepared by dissolving, in 200 ml of THF, 136 g (0.5 mol) of benzoic acid (1,1,1,3,3,3-hexafluoro-2-propyl) obtained by usual preparation process so that the solution temperature did not exceed 50° C., followed by 30-minute stirring. 300 Gram of ice and 150 ml of concentrated hydrochloric acid were put in a 3-liter beaker, followed by stirring, and to the obtained slurry was added the reaction solution gradually. Then an organic layer was separated in the dropping funnel and water layer was extracted two times with 300 ml of n-hexane. The organic layer obtained by two extractions was washed with saturated brine, followed by drying with MgSO$_4$, concentrating with an evaporator and refining by distillation under reduced pressure. Thereby 107.3 g of benzoic acid (1,1,1,3,3-pentafluoro-2-propenyl) was synthesized (boiling point: 71° to 73° C./24 mmHg).

A 500 ml autoclave made of SUS was charged with 65 g (0.257 mol) of benzoic acid (1,1,1,3,3-pentafluoro-2-propenyl), 22 g (0.167 mol) of dicyclopentadiene and 0.73 g (6.6 mmol) of p-hydroquinone, and was cooled in a dry ice/acetone bath, followed by replacing the inside of the autoclave with nitrogen gas. The solution was heated to 170° C. with a heater. After heating and stirring for five hours, the autoclave temperature was lowered to room temperature and a crude product was put in a 3-liter beaker and was dissolved in 0.6 ml of methanol. Stirring was carried out with a magnetic stirrer while cooling in an ice bath, and 0.2 liter of 4N NaOH was added gradually. After stirring for 30 minutes at room temperature, thereto was added 0.6 liter of water and an alkaline aqueous layer was washed with 300 ml of n-hexane. To the alkaline aqueous layer was added concentrated hydrochloric acid until pH thereof became 1, and a separated organic layer was removed and dried with MgSO$_4$. The obtained organic layer was subjected to refining by distillation under reduced

TABLE 2

| Fluorine-containing polymer | Ex. 24 Absorption coefficient at 157 nm ($\mu m^{-1}$) | Ex. 25 Etching rate (to ArF resist) | Ex. 26 Solubility in developing solution | | Ex. 27 Absorption coefficient at 157 nm ($\mu m^{-1}$) |
|---|---|---|---|---|---|
| | | | Before deprotection | After deprotection | |
| Ex. 16 | 1.1 | 1.19 | ○ | — | 1.3 |
| Ex. 17 | 1.2 | 1.15 | X | ○ | 1.4 |
| Ex. 18 | 1.1 | 1.15 | X | ○ | 1.4 |
| Ex. 19 | 0.8 | 1.18 | X | ○ | 1.1 |
| Ex. 20 | 1.0 | 1.13 | Δ* | ○ | 1.3 |
| Ex. 21 | 1.9 | 1.07 | X | ○ | 2.2 |
| Ex. 22 | 1.6 | 1.02 | Δ* | ○ | 1.8 |
| Ex. 23 | 1.6 | 1.00 | ○ | — | 1.8 |

*Δ represents that the polymer is partly dissolved.

pressure and 48.4 g of the intended norbornene derivative (NBC-3) was obtained (boiling point: 55° to 59° C./3 mmHg).

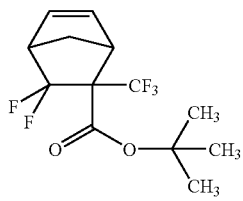

(NBC-3)

The above-mentioned monomer was determined by $^{19}$F-NMR, $^{1}$H-NMR, 13C-NMR and IR analyses.

EXAMPLE 28

(Synthesis of Norbornene Derivative (NB-2(2)))

A 500 ml beaker was charged with 180 ml of methylene chloride, 50 g (0.18 mol) of the norbornene derivative (NB-2) having OH group and 51.1 g (0.23 mol) of ((CH$_3$)$_3$OCOO)$_2$, followed by stirring at room temperature. Then thereto was added 1.1 g (5 mol) of dimethylaminopyridine. After starting the addition, gas was generated gradually and stirring was continued for about one hour until the gas disappeared. After completion of reaction, an organic layer was washed once with pure water and saturated brine in this order. The obtained organic layer was dried and concentrated with Na$_2$SO$_4$ overnight and was distilled to obtain norbornene derivative (NB-2(2)) (yield: 55 g, boiling point: 76° C./0.05 mmHg).

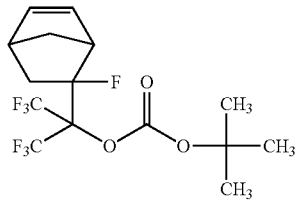

(NB-2(2))

The above-mentioned monomer was determined by $^{19}$F-NMR, $^{1}$H-NMR, $^{13}$C-NMR and IR analyses.

EXAMPLE 29

Synthesis of Norbornene Derivative (NB-3))

A 1-liter flask was evacuated and the inside thereof was replaced with nitrogen gas and then a still was charged with 115 g (1.76 mol) of zinc powder and 400 ml of dehydrated DMF. Then the dropping funnel was charged with 208 g (0.8 mol) of CF$_3$CFBr$_2$ and 100 ml of dehydrated DMF, followed by heating and stirring in nitrogen gas atmosphere. After that, while maintaining at 80° to 90° C., titration was continued over two hours, followed by heating and stirring at 90° to 95° C. for 4.5 hours.

Dimroth condenser was changed to dry ice/acetone condenser and while cooling the still, CF$_3$COCF$_3$ gas was introduced at room temperature. The introduction of CF$_3$COCF$_3$ was terminated at the time when it was determined that the refluxing did not stop and the reaction did not advance. An amount of the introduced gas was 92 g (0.55 mol). Then, after releasing the un-reacted CF$_3$COCF$_3$ by heating and evacuating, diethyl ether was added, followed by washing an organic layer with 1N hydrochloric acid and drying with CaCl$_2$.

As a result of refining by rectification using a rectification tower filled with a filler, 56.6 g of a mixture solution comprising 48.6% of 1,1-bistrifluoromethyl-2,3,3-trifluoro-2-propene-1-ol (CF$_2$=CFC(CF$_3$)$_2$OH) and 47.0% of diethyl ether in an area ratio by GC.

$^{19}$F-NMR (solvent: CDCl$_3$): −77.0 (6F, q), −91.6 (1F, dd), −106.8 (1F, m), −184.1 (1F, m)

MS: 248 (M$^+$), 209, 181, 179, 159, 109, 69 (CF$_3$), 31 (CF)

A 100 ml of autoclave equipped with a pressure gauge, safety valve and stirrer was charged with 45 g (150 mmol) of diethyl ether solution of 1,1-bistrifluoromethyl-2,3,3-trifluoro-2-propene-1-ol comprising the above-mentioned components, 9.9 g (75 mmol) of cyclopentadiene dimer and 0.5 g of hydroquinone, followed by heating and stirring at 170° C. for 24 hours.

A crude product was transferred to a 1-liter beaker, and while cooling in an ice bath, stirring was carried out with a magnetic stirrer and 0.1 liter of 2N aqueous solution of NaOH was added gradually. After stirring at room temperature for 30 minutes, 0.6 liter of water was added thereto and an alkaline solution layer was washed with 100 ml of n-hexane several times. Further this solution layer was treated under reduced pressure to remove ether in the system. To the obtained solution layer was added concentrated hydrochloric acid until pH thereof became 1 and an organic layer was separated. The obtained organic layer was dried with MgSO$_4$ and then was refined by distillation under reduced pressure to obtain 5.9 g of the intended norbornene derivative NB-3 (boiling point: 55° to 60° C./4 mmHg).

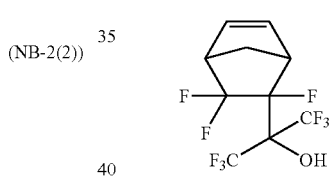

(NB-3)

The above-mentioned monomer was determined by $^{19}$F-NMR, $^{1}$H-NMR, $^{13}$C-NMR and IR analyses.

$^{19}$F-NMR (solvent: CDCl$_3$): −72.5 (6F, d), −73.0 (6F, d), −101.1 (1F, s), −102.0 (1F, s), −103.9 (1F, d), −104.7 (1F, d), −158.4 (1F, d), −161.1 (1F, d)

MS: 314 (M$^+$), 295 (M$^+$—F), 277, 257, 227, 207, 177, 127, 69 (CF$_3$), 66 (C$_5$H$_6$), 51 (CHF$_2$)

EXAMPLE 30

(Synthesis of Norbornene Derivative (NB-3(1)))

A 500 ml four-necked flask equipped with a magnetic stirrer, dropping funnel, 3-way cock and thermometer was charged with 10.6 g (0.26 mol) of NaH and then the inside of the flask was replaced with nitrogen gas and 110 ml of THF was added thereto. While cooling in ice bath, 60 ml of THF solution of 69.1 g (0.22 mol) of norbornene derivative NB-3 was added dropwise gradually. After adding dropwise over one hour, the flask temperature was increased to room temperature and stirring was further continued for two hours. After cooling in ice bath again, 26.0 g (0.28 mol) of ethoxymethyl chloride was added dropwise through the dropping funnel over 30 minutes. After that, stirring was continued overnight at room temperature. A crude product was put in about 500 g of ice water, followed by extraction with diethyl ether while stirring. Then an organic layer was separated in the dropping funnel and aqueous layer was extracted two times with 100 ml of diethyl ether. The organic layer obtained by two extractions was washed with sodium bicarbonate solution or saturated brine, followed by drying with MgSO$_4$, concentrating and refining by distillation under reduced pressure. Thereby 55.3 g of norbornene derivative (NB-3(1)) was obtained (boiling point: 62° to 67° C./1.5 mmHg).

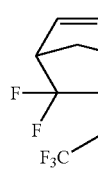

(NB-3(1))

The above-mentioned monomer was determined by $^{19}$F-NMR, $^1$H-NMR, $^{13}$C-NMR and IR analyses.

EXAMPLE 31

(Synthesis of Copolymer Comprising Tetrafluoroethylene, (NB-2) and (NBC-2))

A 500 ml autoclave equipped with a stirrer was subjected to sufficiently replacing with nitrogen gas and evacuating. Then the autoclave was charged with 250 ml of HCFC-141b solution containing 24.5 g of the fluorine-containing norbornene derivative (NB-2) having OH group prepared in Example 4 and 5.8 g of the fluorine-containing norbornene derivative (NBC-2) having —COOC(CH$_3$)$_3$ group.

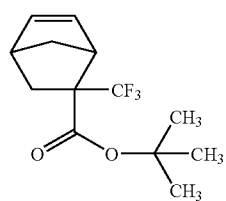

(NBC-2)

Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$G).

After releasing the un-reacted monomer, polymerization solution was removed and was re-precipitated with hexane to separate a copolymer. Until a constant weight was reached, vacuum drying was carried out to obtain 7.8 g of a copolymer.

As a result of $^1$H-NMR and $^{19}$F-NMR analyses, the copolymer was a copolymer of tetrafluoroethylene/fluorine-containing norbornene derivative (NB-2) having OH group/fluorine-containing norbornene derivative (NBC-2) having —COOC(CH$_3$)$_3$ group in % by mole ratio of 50/44/6.

According to GPC analysis, a number average molecular weight thereof was 3,800.

EXAMPLE 32

(Synthesis of Copolymer Comprising Tetrafluoroethylene, (NB-2) and (NBC-2))

A 500 ml autoclave equipped with a stirrer was subjected to sufficiently replacing with nitrogen gas and evacuating. Then the autoclave was charged with 250 ml of HCFC-141b solution containing 18.3 g of the fluorine-containing norbornene derivative (NB-2) having OH group prepared in Example 4 and 12.1 g of the fluorine-containing norbornene derivative (NBC-2) having —COOC(CH$_3$)$_3$ group. Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$ G).

After releasing the un-reacted monomer, polymerization solution was removed and was re-precipitated with hexane to separate a copolymer. Until a constant weight was reached, vacuum drying was carried out to obtain 8.0 g of a copolymer.

As a result of $^1$H-NMR and $^{19}$F-NMR analyses, the copolymer was a copolymer of tetrafluoroethylene/fluorine-containing norbornene derivative (NB-2) having OH group/fluorine-containing norbornene derivative (NBC-2) having —COOC(CH$_3$)$_3$ group in % by mole ratio of 50/38/12.

According to GPC analysis, a number average molecular weight thereof was 3,200.

EXAMPLE 33

(Synthesis of Copolymer Comprising Tetrafluoroethylene, (NB-2) and (NBC-3))

A 500 ml autoclave equipped with a stirrer was subjected to sufficiently replacing with nitrogen gas and evacuating. Then the autoclave was charged with 250 ml of HCFC-141b solution containing 25 g of the fluorine-containing norbornene derivative (NB-2) having OH group and 5.2 g of the fluorine-containing norbornene derivative (NBC-3) having —COOC(CH$_3$)$_3$ group prepared in Preparation Example 3. Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$G).

After releasing the un-reacted monomer, polymerization solution was removed and was re-precipitated with hexane to separate a copolymer. Until a constant weight was reached, vacuum drying was carried out to obtain 8.1 g of a copolymer.

As a result of $^1$H-NMR and $^{19}$F-NMR analyses, the copolymer was a copolymer of tetrafluoroethylene/fluorine-containing norbornene derivative (NB-2) having OH group/fluorine-containing norbornene derivative (NBC-3) having —COOC(CH$_3$)$_3$ group in % by mole ratio of 50/46/4.

According to GPC analysis, a number average molecular weight thereof was 2,600.

EXAMPLE 34

Synthesis of Copolymer Comprising Tetrafluoroethylene, (NB-2) and (NBC-3)

A 500 ml autoclave equipped with a stirrer was subjected to sufficiently replacing with nitrogen gas and evacuating. Then the autoclave was charged with 250 ml of HCFC-141b solution containing 15.3 g of the fluorine-containing norbornene derivative (NB-2) having OH group and 17.3 g of the fluorine-containing norbornene derivative (NBC-3) having —COOC(CH$_3$)$_3$ group prepared in Preparation Example 3. Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$G).

After releasing the un-reacted monomer, polymerization solution was removed and was re-precipitated with hexane to separate a copolymer. Until a constant weight was reached, vacuum drying was carried out to obtain 8.3 g of a copolymer.

As a result of $^1$H-NMR and $^{19}$F-NMR analyses, the copolymer was a copolymer of tetrafluoroethylene/fluorine-containing norbornene derivative (NB-2) having OH group/fluorine-containing norbornene derivative (NBC-3) having —COOC(CH$_3$)$_3$ group in % by mole ratio of 50/36/14.

According to GPC analysis, a number average molecular weight thereof was 2,600.

EXAMPLE 35

(Synthesis of Copolymer Comprising Tetrafluoroethylene, (NB-2) and (NB-2(2)))

A 500 ml autoclave equipped with a stirrer was subjected to sufficiently replacing with nitrogen gas and evacuating. Then the autoclave was charged with 250 ml of HCFC-141b solution containing 27.5 g of the fluorine-containing norbornene derivative (NB-2) having OH group and 4.2 g of the protected fluorine-containing norbornene derivative (NB-2(2)) prepared in Example 28. Then 52 g of tetrafluoroethylene was introduced thereto, followed by heating and stirring. After confirming that the solution temperature had reached 40° C., HCFC-141lb solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm $^2$G) before the reaction to 0.87 MPaG (8.8 kgf/cm $^2$G).

After releasing the un-reacted monomer, polymerization solution was removed and was re-precipitated with hexane to separate a copolymer. Until a constant weight was reached, vacuum drying was carried out to obtain 8.8 g of a copolymer.

As a result of $^1$H-NMR and $^{19}$F-NMR analyses, the copolymer was a copolymer of tetrafluoroethylene/fluorine-containing norbornene derivative (NB-2) having OH group/protected fluorine-containing norbornene derivative (NB-2(2)) in % by mole ratio of 50/46/4.

According to GPC analysis, a number average molecular weight thereof was 2,700.

EXAMPLE 36

(Synthesis of Copolymer Comprising Tetrafluoroethylene, (NB-2) and (NB-2(2)))

A 500 ml autoclave equipped with a stirrer was subjected to sufficiently replacing with nitrogen gas and evacuating. Then the autoclave was charged with 250 ml of HCFC-141b solution containing 21.5 g of the fluorine-containing norbornene derivative (NB-2) having OH group and 12.4 g of the protected fluorine-containing norbornene derivative (NB-2(2)). Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$G).

After releasing the un-reacted monomer, polymerization solution was removed and was re-precipitated with hexane to separate a copolymer. Until a constant weight was reached, vacuum drying was carried out to obtain 9.2 g of a copolymer.

As a result of $^1$H-NMR and $^{19}$F-NMR analyses, the copolymer was a copolymer of tetrafluoroethylene/fluorine-containing norbornene derivative (NB-2) having OH group/protected fluorine-containing norbornene derivative (NB-2(2)) in % by mole ratio of 50/39/11.

According to GPC analysis, a number average molecular weight thereof was 2,900.

EXAMPLE 37

(Synthesis of Copolymer Comprising Tetrafluoroethylene, (NB-3) and (NB-3(1)))

A 500 ml autoclave equipped with a stirrer was subjected to sufficiently replacing with nitrogen gas and evacuating. Then the autoclave was charged with 250 ml of HCFC-141b solution containing 31.1 g of the fluorine-containing norbornene derivative (NB-3) having OH group prepared in Example 29 and 4.1 g of the protected fluorine-containing norbornene derivative (NB-3(1)) prepared in Example 30. Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$G).

After releasing the un-reacted monomer, polymerization solution was removed and was re-precipitated with hexane to separate a copolymer. Until a constant weight was reached, vacuum drying was carried out to obtain 8.8 g of a copolymer.

As a result of $^1$H-NMR and $^{19}$F-NMR analyses, the copolymer was a copolymer of tetrafluoroethylene/fluorine-containing norbornene derivative (NB-3) having OH group/protected fluorine-containing norbornene derivative (NB-3(1)) in % by mole ratio of 50/46/4.

According to GPC analysis, a number average molecular weight thereof was 2,700.

EXAMPLE 38

(Synthesis of Copolymer Comprising Tetrafluoroethylene, (NB-3) and (NB-3(1)))

A 500 ml autoclave equipped with a stirrer was subjected to sufficiently replacing with nitrogen gas and evacuating. Then the autoclave was charged with 250 ml of HCFC-141b solution containing 20.7 g of the fluorine-containing norbornene derivative (NB-3) having OH group prepared in Example 29 and 16.4 g of the protected fluorine-containing norbornene derivative (NB-3(1)) prepared in Example 30. Then 52 g of tetrafluoroethylene was introduced thereto, followed by heating and stirring. After confirming that the solution temperature had reached 40° C., HCFC-141b solution containing 6.5 g of bis(4-t-butylcyclohexyl)peroxydicarbonate (TCP) was introduced under pressure, followed by reaction at 40° C. for six hours. With the advance of the reaction, the gauge pressure was lowered from 0.89 MPaG (9.0 kgf/cm$^2$G) before the reaction to 0.87 MPaG (8.8 kgf/cm$^2$G).

After releasing the un-reacted monomer, polymerization solution was removed and was re-precipitated with hexane to separate a copolymer. Until a constant weight was reached, vacuum drying was carried out to obtain 8.6 g of a copolymer.

As a result of $^1$H-NMR and $^{19}$F-NMR analyses, the copolymer was a copolymer of tetrafluoroethylene/fluorine-containing norbornene derivative (NB-3) having OH group/protected fluorine-containing norbornene derivative (NB-3(1)) in % by mole ratio of 50/32/18.

According to GPC analysis, a number average molecular weight thereof was 2,900.

EXAMPLE 39

(Synthesis of Copolymer Comprising Tetrafluoroethylene and (NB-3))

Reaction and separation and refining of a polymer were carried out in the same manner as in Example 16 except that 40.0 g of the fluorine-containing norbornene (NB-3) having OH group prepared in Example 29 was used instead of the fluorine-containing norbornene (NB-2) having OH group prepared in Example 4, and thereby 5.5 g of a copolymer was obtained.

As a result of $^1$H-NMR and $^{19}$F-NMR analyses, the copolymer was a copolymer of tetrafluoroethylene/fluorine-containing norbornene (NB-3) having OH group in % by mole ratio of 50/50.

According to GPC analysis, a number average molecular weight thereof was 3,500.

EXAMPLE 40

(Measurement of pKa of Various Fluorine-containing Norbornene Derivatives Having OH Group)

First mentioned below is a method of measuring pKa of the norbornene derivative (NB-1) having OH group.

In a solution of water/acetone of 10/15 ml was put 0.5864 g of the norbornene derivative (NB-1) having OH group prepared in Example 2, followed by stirring at room temperature. After it was confirmed that the solution became homogeneous, titration was carried out with an about 0.2 mol/liter NaOH solution. A titration curve was obtained by adding a NaOH solution dropwise in increments of 0.15 ml and recording a pH value at every addition. An equivalence point was determined by an inflection point (maximum differential value of titration curve=dpH/dml) of the titration curve. In this case, the equivalence point was 8.45 ml. A pH value at 4.23 ml which is a half of the equivalence point was read from the titration curve and was found to be 11.48. From a titration curve prepared from a water/acetone solution and aqueous solution which had been measured previously as a blank solution, a difference in a pH value derived from an electric potential difference between the solutions at titration of 4.23 ml was 1.46. Therefore from 11.48−1.46=10.02, a pKa value of this norbornene derivative (NB-1) was determined as 10.0.

In case of titration of 0.7235 g of the norbornene (NB-1) by the same procedures as above, an equivalence point was 11.2 ml and a half of equivalence point was 5.6 ml. A pH value at a half of the equivalence point was 11.76. A difference in a pH value between the both solutions at 5.6 ml was 1.38, and from 11.76−1.38=10.38, a pKa value of the norbornene derivative (NB-1) was determined as 10.4.

When titration of 1.1251 g of the norbornene derivative (NB-1) was carried out by the same procedures as above, an equivalence point was 16.8 ml and a half of equivalence point was 8.4 ml. A pH value at a half of the equivalence point was 11.37. A difference in a pH value between the both solutions at 8.4 ml was 1.21, and from 11.37−1.21=10.16, a pKa value of the norbornene derivative (NB-1) was determined as 10.2.

From those experiments carried out three times, a pKa value of the norbornene derivative (NB-1) was determined as 10.2.

With respect to the fluorine-containing norbornene derivative (NB-2) having OH group prepared in Example 4 and the fluorine-containing norbornene derivative (NB-3) having OH group prepared in Example 29, pKa values thereof were measured and determined in the same manner as above.

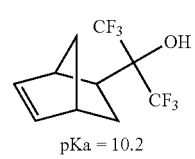

pKa = 10.2

NB-1

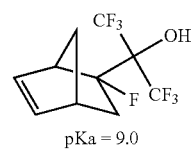

pKa = 9.0

NB-2

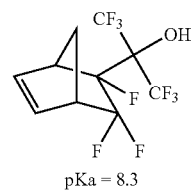

pKa = 8.3

NB-3

EXAMPLE 41

(Measurement of Transparency at a Wavelength of 157 nm)

(1) Preparation of coating composition, (2) coating and (3) measurement of transparency in a vacuum ultraviolet region were carried out in the same manner as in Example 12 by using the respective fluorine-containing polymers prepared in Examples 31 to 39. A molecular absorption coefficient at 157 nm is shown in Table 3.

EXAMPLE 42

(Evaluation of Solubility in Developing Solution)

(1) Deprotection reaction of protective group, (2) coating and (3) determination of solubility were carried out in the same manner as in Example 14 by using the respective fluorine-containing polymers prepared in Examples 31 to 39. The results are shown in Table 3.

EXAMPLE 43

(1) Preparation of resist composition, (2) coating and (3) measurement of transparency in vacuum ultraviolet region were carried out in the same manner as in Example 15 by using the respective fluorine-containing polymers (A) prepared in Examples 31 to 39. The results are shown in Table 3.

TABLE 3

| Fluorine-containing polymer | Ex. 41 Absorption coefficient at 157 nm ($\mu m^{-1}$) | Ex. 42 Solubility in developing solution | | Ex. 43 Absorption coefficient at 157 nm ($\mu m^{-1}$) |
|---|---|---|---|---|
| | | Before deprotection | After deprotection | |
| Ex. 31 | 1.8 | Δ* | ◯ | 2.0 |
| Ex. 32 | 2.3 | X | ◯ | 2.6 |
| Ex. 33 | 1.4 | Δ* | ◯ | 1.6 |
| Ex. 34 | 1.7 | X | ◯ | 2.0 |
| Ex. 35 | 1.8 | X | ◯ | 2.0 |
| Ex. 36 | 2.2 | X | ◯ | 2.5 |
| Ex. 37 | 0.6 | ◯ | ◯ | 0.8 |
| Ex. 38 | 0.7 | X | ◯ | 0.9 |
| Ex. 39 | 0.5 | ◯ | — | 0.7 |

*Δ represents that the polymer is partly dissolved.

PREPARATION EXAMPLE 4

(Synthesis of Norbornene Derivative (NBC-4) Having —COOH Group)

A 2-liter four-necked flask equipped with a thermometer, stirrer and dropping funnel was charged with 1.2 liter of 1.0 N aqueous solution of NaOH and was maintained at 10° C. or lower in an ice bath. Thereto was added dropwise gradually 158 g of the norbornene compound having —COF group prepared in Preparation Example 1. After one-hour stirring, thereto was added 10% hydrochloric acid solution to adjust a pH value of the mixture to 2 or lower. An organic substance was extracted with chloroform, and the chloroform layer was washed with water and then dried with anhydrous magnesium sulfate.

After the drying, the organic layer was separated and methylene chloride was distilled off, followed by distillation under reduced pressure. Thereby 125 g of a norbornene derivative (NBC-4) having —COOH group which is an acid-reactive group:

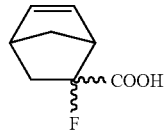
(NBC-4)

(melting point: 80° to 81° C./0.55 mmHg) was obtained.

The above-mentioned structure of this compound was determined by GC-Mass, $^{19}$F-NMR and $^{1}$H-NMR analyses.

EXAMPLE 44

(Synthesis of Copolymer Comprising TFE, Fluorine-containing Norbornene Derivative (NBC-4) Having —COOH Group and Fluorine-containing Norbornene Derivative (NB-2(1)) Having —OCH$_2$OC$_2$H$_5$ Group)

Polymerization reaction and separation and refining of a polymer were carried out in the same manner as in Example 18 except that 1.8 g of the fluorine-containing norbornene derivative (NBC-4) having —COOH group obtained in Preparation Example 4 was used instead of the fluorine-containing norbornene derivative (NB-2) having —OH group, and 33.3 g of the fluorine-containing norbornene derivative (NB-2(1)) having —OCH$_2$OC$_2$H$_5$ group, 52.5 g of TFE and 6.5 g of TCP were used. Thereby 4.0 g of a copolymer was obtained.

As a result of $^{1}$H-NMR and $^{19}$F-NMR analyses, the copolymer was a copolymer of TFE/fluorine-containing norbornene derivative (NBC-4) having —COOH group/fluorine-containing norbornene derivative (NB-2(1)) having —OCH$_2$OC$_2$H$_5$ group in % by mole ratio of 50/8/42.

According to GPC analysis, a number average molecular weight thereof was 2,800.

EXAMPLE 45

Synthesis of Copolymer Comprising TFE, Fluorine-Containing Norbornene Derivative (NBC-4) Having —COOH Group and Fluorine-Containing Norbornene Derivative (NB-2(1)) Having —OCH$_2$OC$_2$H$_5$ Group Polymerization reaction and separation and refining of a polymer were carried out in the same manner as in Example 44 except that 3.5 g of the fluorine-containing norbornene derivative (NBC-4) having —COOH group, 29.6 g of the fluorine-containing norbornene derivative (NB-2(1)) having —OCH$_2$OC$_2$H$_5$ group and 52.5 g of TFE were used. Thereby 5.0 g of a copolymer was obtained.

As a result of $^{1}$H-NMR and $^{19}$F-NMR analyses, the copolymer was a copolymer of TFE/fluorine-containing norbornene derivative (NBC-4) having —COOH group/fluorine-containing norbornene derivative (NB-2(1)) having —OCH$_2$OC$_2$H$_5$ group in % by mole ratio of 50/13/37.

According to GPC analysis, a number average molecular weight thereof was 3,000.

EXAMPLE 46

Synthesis of Copolymer Comprising Tetrafluoroethylene, (NB-3) and (NBC-1)

Polymerization reaction and separation and refining of a polymer were carried out in the same manner as in Example 37 except that 2.3 g of the fluorine-containing norbornene derivative (NBC-1) having —COOC(CH$_3$)$_3$ group was used instead of the fluorine-containing norbornene derivative (NB-3(1)) having —OCH$_2$OC$_2$H$_5$ group, and 31.1 g of the fluorine-containing norbornene derivative (NB-3) having —OH group, 52.5 g of TFE and 6.5 g of TCP were used. Thereby 4.2 g of a copolymer was obtained.

As a result of $^1$H-NMR and $^{19}$F-NMR analyses, the copolymer was a copolymer of TFE/fluorine-containing norbornene derivative (NB-3) having —OH group/fluorine-containing norbornene derivative (NBC-1) having —COOC(CH$_3$)$_3$ group in % by mole ratio of 50/40/10.

According to GPC analysis, a number average molecular weight thereof was 2,800.

EXAMPLE 47

Synthesis of Copolymer Comprising Tetrafluoroethylene, (NB-3) and (NBC-1))

Polymerization reaction and separation and refining of a polymer were carried out in the same manner as in Example 46 except that 2.3 g of the fluorine-containing norbornene derivative (NBC-1) having —COOC(CH$_3$)$_3$ group, 31.1 g of the fluorine-containing norbornene derivative (NB-3) having —OH group, 52.5 g of TFE and 6.5 g of TCP were used. Thereby 5.0 g of a copolymer was obtained.

As a result of $^1$H-NMR and $^{19}$F-NMR analyses, the copolymer was a copolymer of TFE/fluorine-containing norbornene derivative (NB-3) having —OH group/fluorine-containing norbornene derivative (NBC-1) having —COOC(CH$_3$)$_3$ group in % by mole ratio of 50/39/11.

According to GPC analysis, a number average molecular weight thereof was 2,500.

EXAMPLE 48

(Synthesis of Copolymer Comprising Tetrafluoroethylene, (NB-3) and (NBC-1))

Polymerization reaction and separation and refining of a polymer were carried out in the same manner as in Example 47 except that 24.2 g of the fluorine-containing norbornene derivative (NB-3) having —OH group, 7.0 g of the fluorine-containing norbornene derivative (NBC-1) having —COOC(CH$_3$)$_3$ group, 52.0 g of TFE and 6.6 g of TCP were used. Thereby 4.8 g of a copolymer was obtained.

As a result of $^1$H-NMR and $^{19}$F-NMR analyses, the copolymer was a copolymer of TFE/fluorine-containing norbornene derivative (NB-3) having —OH group/fluorine-containing norbornene derivative (NBC-1) having —COOC(CH$_3$)$_3$ group in % by mole ratio of 50/25/25.

According to GPC analysis, a number average molecular weight thereof was 3,200.

EXAMPLE 49

(Synthesis of Copolymer Comprising Tetrafluoroethylene, (NB-3) and (NBC-3))

Polymerization reaction and separation and refining of a polymer were carried out in the same manner as in Example 46 except that. 9.8 g of the fluorine-containing norbornene derivative (NBC-3) having —COOC(CH$_3$)$_3$ group was used instead of NBC-1, and 24.2 g of the fluorine-containing norbornene derivative (NB-3) having —OH group, 52.5 g of TFE and 6.5 g of TCP were used. Thereby 4.7 g of a copolymer was obtained.

As a result of $^1$H-NMR and $^{19}$F-NMR analyses, the copolymer was a copolymer of TFE/fluorine-containing norbornene derivative (NB-3) having —OH group/fluorine-containing norbornene derivative (NBC-3) having —COOC(CH$_3$)$_3$ group in % by mole ratio of 50/37/13.

According to GPC analysis, a number average molecular weight thereof was 2,500.

EXAMPLE 50

(Measurement of Transparency at a Wavelength of 157 nm)

(1) Preparation of coating composition, (2) coating and (3) measurement of transparency in a vacuum ultraviolet region were carried out in the same manner as in Example 12 by using the respective fluorine-containing polymers prepared in Examples 44 to 49. A molecular absorption coefficient at 157 nm is shown in Table 4.

EXAMPLE 51

(Evaluation of Solubility in Developing Solution)

(1) Deprotection reaction of protective group, (2) coating and (3) determination of solubility were carried out in the same manner as in Example 14 by using the respective fluorine-containing polymers prepared in Examples 44 to 49. The results are shown in Table 4.

EXAMPLE 52

(1) Preparation of resist composition, (2) coating and (3) measurement of transparency in a vacuum ultraviolet region were carried out in the same manner as in Example 15 by using the respective fluorine-containing polymers (A) prepared in Examples 44 to 49. The results are shown in Table 4.

TABLE 4

| Fluorine-containing polymer | Ex. 50 Absorption coefficient at 157 nm (μm$^{-1}$) | Ex. 51 Solubility in developing solution | | Ex. 52 Absorption coefficient at 157 nm (μm$^{-1}$) |
|---|---|---|---|---|
| | | Before deprotection | After deprotection | |
| Ex. 44 | 2 | X | ◯ | 2.2 |
| Ex. 45 | 2.3 | Δ* | ◯ | 2.6 |
| Ex. 46 | 1.2 | X | ◯ | 1.6 |
| Ex. 47 | 0.8 | X | ◯ | 2 |
| Ex. 48 | 2.5 | X | ◯ | 2.8 |
| Ex. 49 | 0.6 | X | ◯ | 0.8 |

*Δ represents that the polymer is partly dissolved.

EXAMPLE 53

After drying a 2-liter four-necked flask equipped with a thermometer, stirrer and dropping funnel, the flask was charged with 210 g (in 100 ml THF solution) of dimethyl ester derived from anhydrous 5-norbornene-2,3-dicarboxylic acid and methanol and 900 ml of tetrahydrofuran (THF) sufficiently dried and was then dipped in a water bath. Thereto was added dropwise 420 g of trimethyltrifluoromethylsilane over one hour. After three-hour stirring at room temperature, the reaction system was again cooled in an ice bath, and 50 ml of 1.0 M tetrahydrofuran (THF) solution of tetrabutyl ammonium fluoride was added thereto gradually. After one-hour stirring, an excessive amount of 10% hydrochloric acid solution was added thereto. An organic substance was extracted with methylene chloride and after washing with water, a methylene chloride layer was dried with anhydrous magnesium sulfate. After the drying, an organic layer was separated and methylene chloride was distilled off and then distillation under reduced pressure was carried out to obtain 150 g of an intermediate reaction product (melting point of 60° to 65° C./2.7 mmHg).

Subsequently a 1-liter four-necked flask equipped with a thermometer, stirrer and dropping funnel was charged with 143 g of the intermediate reaction product and 400 ml of THF and was dipped in a water bath of room temperature. Thereto was added dropwise 152 g of trimethyltrifluoromethylsilane over one hour. After three-hour stirring at room temperature, the reaction system was cooled again in ice bath and 25 ml of 1.0 M tetrahydrofuran (THF) solution of tetrabutylammonium fluoride was added thereto gradually. Then after one-hour stirring, an excessive amount of 10% hydrochloric acid solution was added thereto. After an organic substance was extracted with methylene chloride, a methylene chloride layer was washed with water and then dried with anhydrous magnesium sulfate. After the drying, the organic layer was separated and methylene chloride was distilled off, followed by fractional distillation under reduced pressure. Thereby 85 g of a norbornene derivative (NB-4) having —C(CF$_3$)$_2$OH group which is an acid-reactive group:

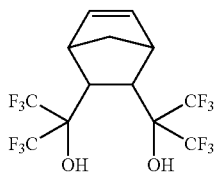

(melting point: 70° to 71° C./1.70 mmHg) was obtained.

The above-mentioned structure of this compound was analyzed and determined by GC-Mass, $^{19}$F-NMR and $^1$H-NMR analyses.

EXAMPLE 54

A 500 ml four-necked flask equipped with a thermometer, stirrer and dropping funnel was charged with 1.3 g of sodium hydride, followed by drying. Thereto was added 150 ml of sufficiently dried tetrahydrofuran (THF), followed by cooling in an ice bath. Then thereto was added dropwise a solution of 22 g of the bifunctional norbornene derivative (NB-4) prepared in Example 53 and 150 ml of THF gradually over one hour. After completion of the addition, stirring was carried out at room temperature for three hours and then the reaction system was again cooled in an ice bath, followed by gradually adding ethoxymethyl chloride. After stirring for one hour and then further stirring at room temperature overnight, an excessive amount of 10% hydrochloric acid solution was added. An organic substance was extracted with methylene chloride, and the methylene chloride layer was washed with water and then dried with anhydrous magnesium sulfate. After the drying, the organic layer was separated and methylene chloride was distilled off, followed by distillation under reduced pressure. Thereby 15 g of a norbornene derivative (NB-5) having —OCH$_2$OC$_2$H$_5$ group which is an acid-reactive group:

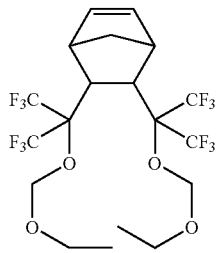

(melting point: 79° to 81° C./0.50 mmHg) was obtained.

The above-mentioned structure of this compound was analyzed and determined by GC-Mass, $^{19}$F-NMR and $^1$H-NMR analyses.

EXAMPLE 55

(Synthesis of Copolymer Comprising Tetrafluoroethylene and (NB-4))

Polymerization reaction and separation and refining of a polymer were carried out in the same manner as in Example 46 except that 46.9 g of the fluorine-containing norbornene derivative (NB-4) having —OH group prepared in Example 53 was used instead of the fluorine-containing norbornene derivative (NB-3) having —OH group, and 52.5 g of TFE and 6.5 g of TCP were used. Thereby 5.3 g of a copolymer was obtained.

As a result of $^1$H-NMR and $^{19}$F-NMR analyses, the copolymer was a copolymer of TFE/fluorine-containing norbornene derivative (NB-4) having —OH group in % by mole ratio of 50/50.

According to GPC analysis, a number average molecular weight thereof was 2,400.

EXAMPLE 56

(Synthesis of Copolymer Comprising Tetrafluoroethylene and (NB-5))

Polymerization reaction and separation and refining of a polymer were carried out in the same manner as in Example 46 except that 59.6 g of the fluorine-containing norbornene derivative (NB-5) having —OCH$_2$OC$_2$H$_5$ group prepared in Example 54 was used instead of the fluorine-containing norbornene derivative (NB-3) having —OH group, and 52.5 g of TFE and 6.5 g of TCP were used. Thereby 5.0 g of a copolymer was obtained.

As a result of $^1$H-NMR and $^{19}$F-NMR analyses, the copolymer was a copolymer of TFE/fluorine-containing norbornene derivative (NB-5) having —OCH$_2$OC$_2$H$_5$ group in % by mole ratio of 50/50.

According to GPC analysis, a number average molecular weight thereof was 2,200.

The fluorine-containing polymer obtained by using the novel norbornene derivative of the present invention as a copolymerizable component is excellent in transparency, possesses improved dry etching resistivity and is useful as a material for chemically amplifying type photoresist for F$_2$ laser.

What is claimed is:

1. A fluorine-containing polymer having a number average molecular weight of from 500 to 1,000,000 which has a ring structure in the polymer trunk chain and is represented by the formula (13):

-(M1)-(M2)-(N)-  (13)

wherein M1, in its monomeric form, is at least one monomer selected from the fluorine-containing norbornene compounds represented by the formulae (5) to (12):

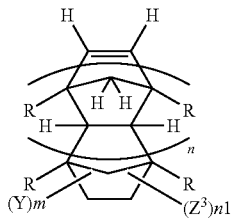
(5)

wherein $Z^3$ the same or different and each is:

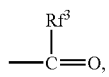

wherein, $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

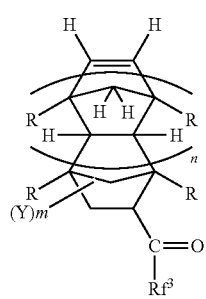
(6)

wherein, $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is 5;

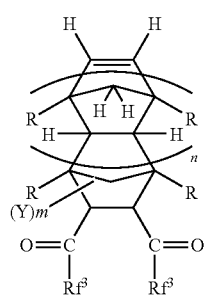
(7)

wherein, $Rf^3$ is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is 4;

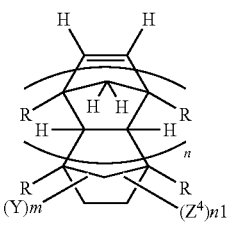
(8)

wherein $Z^4$ is the same or different and each is:

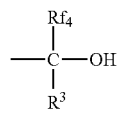

wherein, $Rf^4$ is the same or different and each is a fluorine-containing alkyl group having 1 to 10 carbon atoms or a fluorine-containing alkyl group which has 1 to 10 carbon atoms and ether bond; $R^3$ is H or a hydrocarbon group having 1 to 10 carbon atoms; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

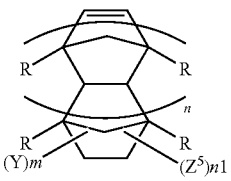
(9)

wherein $Z^5$ is the same or different and each is:

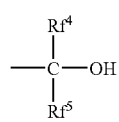

wherein, $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

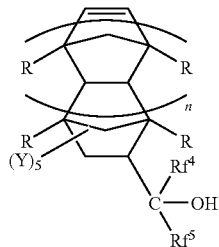
(10)

wherein, $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5;

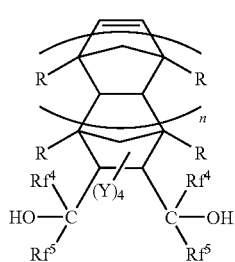
(11)

wherein, $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; and

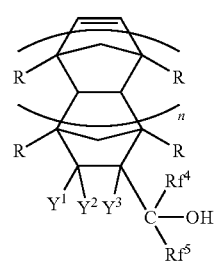
(12)

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; at least one of $Y^1$, $Y^2$ and $Y^3$ is F or a fluorine-containing alkyl group which has 1 to 10 carbon atoms and may have ether bond;

M2, in its monomeric form, is a fluorine-containing ethylenic monomer having 2 or 3 carbon atoms and at least one fluorine atom; and N, in its monomeric form, is an ethylenically unsaturated monomer copolymerizable with M1 and M2, and the structural units M1, M2 and N are contained in amounts of from 1 to 99% by mole, from 1 to 99% by mole and from 0 to 98% by mole, respectively.

2. The fluorine-containing polymer of claim 1, wherein in the formula (13), provided that (M1)+(M2) is 100% by mole, a percent by mole ratio of M1/M2 is 30/70 to 70/30.

3. A fluorine-containing polymer having a number average molecular weight of from 500 to 1,000,000 which has a ring structure in the polymer trunk chain and is represented by the formula (13)-1:

-(M1-1)-(M1-2)-(M2)-(N)- (13)-1 wherein

M1-1, in its monomeric form, is at least one monomer selected from the norbornene compounds having a fluorine-containing alcohol structure represented by the formulae (8) to (12);

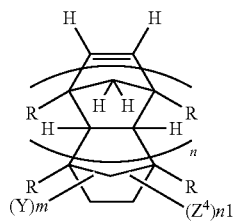
(8)

wherein $Z^4$ is the same or different and each is:

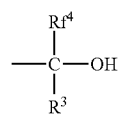

wherein, $Rf^4$ is the same or different and each is a fluorine-containing alkyl group having 1 to 10 carbon atoms or a fluorine-containing alkyl group which has 1 to 10 carbon atoms and ether bond; $R^3$ is H or a hydrocarbon group having 1 to 10 carbon atoms; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1to 5; m+n1=6;

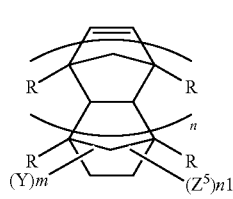
(9)

wherein $Z^5$ is the same or different and each is:

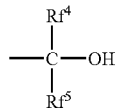

(5)

wherein, $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

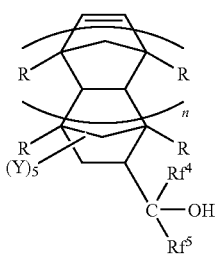

(10)

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5;

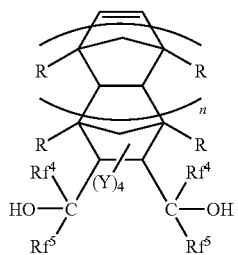

(11)

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; and

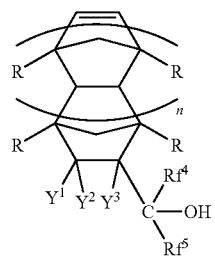

(12)

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; at least one of $Y^1$, $Y^2$ and $Y^3$ is F or a fluorine-containing alkyl group which has 1 to 10 carbon atoms and may have ether bond;

M1-2, in its monomeric form, is at least one monomer selected from the norbornene compounds having a fluorine-containing alcohol structure which are represented by the formulae (8) to (12) and which have a protective acid-reactive functional group protecting hydroxyl thereof;

M2, in its monomeric form, is a fluorine-containing ethylenic monomer having 2 or 3 carbon atoms and at least one fluorine atom; and N, in its monomeric form, is an ethylenically unsaturated monomer copolymerizable with M1-1, M1-2 and M2, provided that (M1-1)+(M1-2)+M2 is 100% by mole, a percent by mole ratio of ((M1-1)+(M1-2))/M2 is 30/70 to 70/30, and structural units M1-2, M1-2, M2 and N are contained in amounts of from 1 to 98% by mole, from 1 to 98% by mole, from 1 to 98% by mole and from 0 to 97% by mole, respectively.

4. The fluorine-containing polymer of claim 3, wherein provided that (M1-1)+(M1-2) is 100% by mole, a percent by mole ratio of (M1-1)/(M1-2) is 90/10 to 50/50.

5. A fluorine-containing polymer represented by the formula (13)-2:

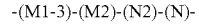

-(M1-3)-(M2)-(N2)-(N)-    (13)-2

M2, in its monomeric form, is a fluorine-containing ethylenic monomer having 2 or 3 carbon atoms and at least one fluorine atom, M1-3, in its monomeric form, is at least one selected from the norbornene compounds represented by the formulae (8) to (12),

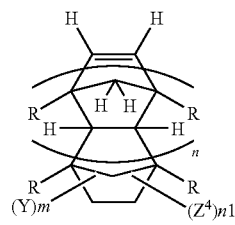

(8)

wherein $Z^4$ is the same or different and each is:

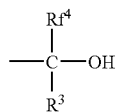

wherein, $Rf^4$ is the same or different and each is a fluorine-containing alkyl group having 1 to 10 carbon atoms or a fluorine-containing alkyl group which has 1 to 10 carbon atoms and ether bond; $R^3$ is H or a hydrocarbon group having 1 to 10 carbon atoms; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

(9)

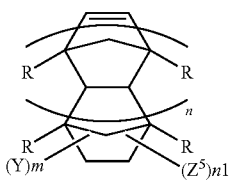

wherein $Z^5$ is the same or different and each is:

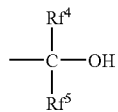

wherein, $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

(10)

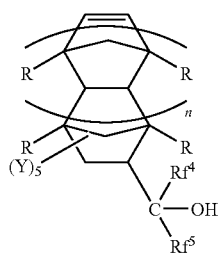

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5;

(11)

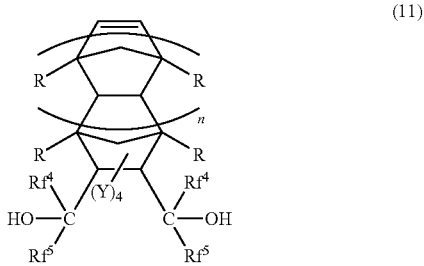

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; and (12)

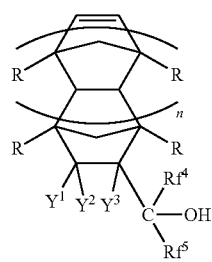

wherein $Rf^4$ and $Rf^5$ are the same or different and each is a fluorine-containing alkyl group having 1 to 10 carbon atoms or a fluorine-containing alkyl group which has 1 to 10 carbon atoms 1 2 3 and ether bond; $Y^1$, $Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; at least one of $Y^1$, $Y^2$ and $Y^3$ is F or a fluorine-containing alkyl group which has 1 to 10 carbon atoms and may have ether bond;

N2, in its monomeric form, is a cyclic aliphatic unsaturated hydrocarbon which is copolymerizable with monomers constituting structural units M1-3, M2 and N and has COOH group or an acid-labile functional group which can be converted to carboxyl due to action of an acid; and N, in its monomeric form, is an ethylenically unsaturated monomer copolymerizable with M1-3, M2 and N2, provided that (M1-3)+M2+N2 is 100% by mole, a percent by mole ratio of ((M1-3)+N2)/M2 is 70/30 to 30/70, and structural units M1-3, M2, N2 and N are contained in amounts of from 1 to 98% by mole, from 1 to 98% by mole, from 1 to 98% by mole and from 0 to 97% by mole, respectively.

6. The fluorine-containing polymer of claim 5, wherein in the fluorine-containing polymer of the formula (13)-2, N2 is a structural unit comprising a norbornene compound having COOH group or an acid-labile functional group which can be converted to carboxyl due to action of an acid.

7. The fluorine-containing polymer of claim 6, wherein the norbornene compound having COOH group or an acid-labile functional group which can be converted to carboxyl due to action of an acid is represented by the formula:

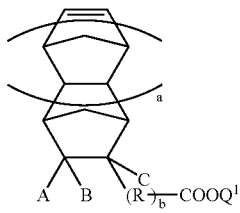

wherein A, B and C are H, F, alkyl groups having 1 to 10 carbon atoms or fluorine-containing alkyl groups having 1 to 10 carbon atoms, R is a divalent hydrocarbon group having 1 to 20 carbon atoms, a fluorine-containing alkylene group having 1 to 20 carbon atoms or a fluorine-containing alkylene group having 2 to 100 carbon atoms and ether bond, a is 0 or an integer of from 1 to 3, b is 0 or 1, $COOQ^1$ is COOH group or an acid-labile functional group which can be converted to carboxyl due to action of an acid, provided that b is 0 or R does not have fluorine atom, any one of A, B and C is fluorine atom or a fluorine-containing alkyl group.

8. A fluorine-containing polymer represented by the formula (13)-3:

wherein M1-1, in its monomeric form, is at least one selected from the norbornene compounds having a fluorine-containing alcohol structure represented by the formulae (8) to (12)

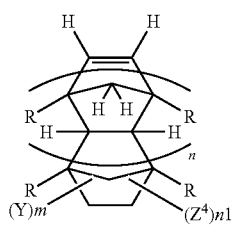

wherein $Z^4$ is the same or different and each is:

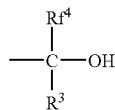

wherein, $Rf^4$ is the same or different and each is a fluorine-containing alkyl group having 1 to 10 carbon atoms or a fluorine-containing alkyl group which has 1 to 10 carbon atoms and ether bond; $R^3$ is H or a hydrocarbon group having 1 to 10 carbon atoms; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

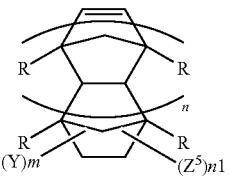

wherein $Z^5$ is the same or different and each is:

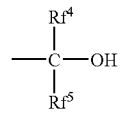

wherein, $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; m is an integer of from 1 to 5; n1 is an integer of from 1 to 5; m+n1=6;

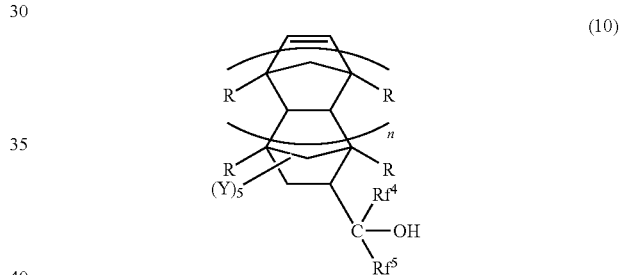

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5;

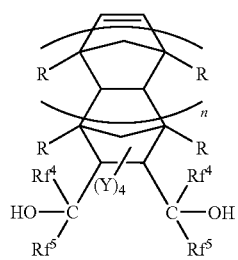

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; Y is the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; and

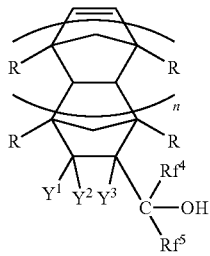

(12)

wherein $Rf^4$ and $Rf^5$ are the same or different and each is a fluorine-containing alkyl group having 1 to 10 carbon atoms or a fluorine-containing alkyl group which has 1 to 10 carbon atoms and ether bond; $Y^1, Y^2$ and $Y^3$ are the same or different and each is H, F, Cl, an alkyl group having 1 to 10 carbon atoms or a fluorine-containing alkyl group which has 1 to 10 carbon atoms and may have ether bond; R is the same or different and each is H or an alkyl group having 1 to 10 carbon atoms; n is 0 or an integer of from 1 to 5; at least one of $Y^1, Y^2$ and $Y^3$ is F or a fluorine-containing alkyl group which has 1 to 10 carbon atoms and may have ether bond;

M2, in its monomeric form, is a fluorine-containing ethylenic monomer having 2 or 3 carbon atoms and at least one fluorine atom;

N2-1, in its monomeric form, is at least one monomer selected from the norbornene compounds represented by the formula:

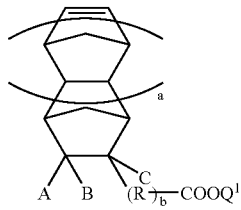

wherein $COOQ^1$ is COOH group or an acid-labile functional group which can be converted to carboxyl due to action of an acid, A, B and C are H, F, alkyl groups having 1 to 10 carbon atoms or fluorine-containing alkyl groups having 1 to 10 carbon atoms, R is a divalent hydrocarbon group having 1 to 20 carbon atoms, a fluorine-containing alkylene group having 1 to 20 carbon atoms or a fluorine-containing alkylene group having 2 to 100 carbon atoms and ether bond, a is 0 or an integer of from 1 to 3, b is 0 or 1, provided that b is 0 or R does not fluorine atom, any one of A, B and C is fluorine atom or a fluorine-containing alkyl group;

N, in its monomeric form, is an ethylenically unsaturated monomer copolymerizable with M1-1, M2 and N2-1, provided that (M1-1)+(M2)+(N2-1) is 100% by mole, a percent by mole ratio of ((M1-1)+N2-1))/(M2) is 70/30 to 30/70, and provided that (M1-1)+(N2-1) is 100% by mole, a percent by mole ratio of(M1-1)/(N2-1) is 95/5 to 50/50, and structural units M1-1, M2, N2-1 and N are contained in amounts of from 1 to 98% by mole, from 1 to 98% by mole, from 1 to 98% by mole and from 0 to 97% by mole, respectively.

9. The fluorine-containing polymer of claim 1, wherein M2, in its monomeric form, is a structural unit comprising tetrafluoroethylene or chlorotrifluoroethylene.

10. The fluorine-containing polymer of claim 3, wherein M2, in its monomeric form, is a structural unit comprising tetrafluoroethylene or chlorotrifluoroethylene.

11. The fluorine-containing polymer of claim 5, wherein M2, in its monomeric form, is a structural unit comprising tetrafluoroethylene or chlorotrifluoroethylene.

12. The fluorine-containing polymer of claim 8, wherein M2, in its monomeric form is a structural unit comprising tetrafluoroethylene or chlorotrifluoroethylene.

* * * * *